(12) United States Patent
Phillips

(10) Patent No.: US 10,519,327 B2
(45) Date of Patent: Dec. 31, 2019

(54) METHODS AND COATINGS FOR PROTECTING SURFACES FROM BIO-FOULING SPECIES

(71) Applicant: REDJAK, L.L.C., Larchmont, NY (US)

(72) Inventor: Reed E. Phillips, Glen Cove, NY (US)

(73) Assignee: REDJAK, L.L.C., Larchmont, NY (US)

( * ) Notice: Subject to any disclaimer, the term of this patent is extended or adjusted under 35 U.S.C. 154(b) by 0 days.

(21) Appl. No.: 16/285,676

(22) Filed: Feb. 26, 2019

(65) Prior Publication Data

US 2019/0322876 A1 Oct. 24, 2019

Related U.S. Application Data

(63) Continuation-in-part of application No. 15/958,575, filed on Apr. 20, 2018.

(51) Int. Cl.
| | | |
|---|---|---|
| C09J 11/08 | (2006.01) | |
| C09D 5/16 | (2006.01) | |
| A01N 55/02 | (2006.01) | |
| B63B 59/04 | (2006.01) | |

(52) U.S. Cl.
CPC ........... *C09D 5/1693* (2013.01); *A01N 55/02* (2013.01); *B63B 59/04* (2013.01)

(58) Field of Classification Search
CPC .... C09D 5/008; C09D 5/1625; C09D 5/1668; C09D 7/63; C09D 7/70; C09D 5/1675; C09D 5/1693; D06M 16/003; B63B 59/04
See application file for complete search history.

(56) References Cited

U.S. PATENT DOCUMENTS

| | | |
|---|---|---|
| 3,241,512 A | 3/1966 | Green |
| 4,157,358 A | 6/1979 | Field et al. |
| 5,143,011 A | 9/1992 | Rabbette et al. |
| 5,226,380 A | 7/1993 | Fischer |
| 5,397,385 A | 3/1995 | Watts |
| 5,492,696 A | 2/1996 | Price et al. |
| 5,663,215 A * | 9/1997 | Milligan ............ C09D 5/1675 427/386 |
| 5,912,286 A | 6/1999 | Griffith et al. |
| 5,945,171 A | 8/1999 | Cook |
| 5,998,200 A | 12/1999 | Bonaventura et al. |
| 6,280,759 B1 | 8/2001 | Price et al. |
| 6,538,031 B1 | 3/2003 | Schmid |
| 7,544,367 B2 | 6/2009 | Mohseni et al. |
| 8,129,460 B2 | 3/2012 | Geisler et al. |

(Continued)

FOREIGN PATENT DOCUMENTS

| | | |
|---|---|---|
| CN | 1364056 A | 8/2002 |
| EP | 0093497 A2 | 11/1983 |

(Continued)

*Primary Examiner* — Michael B Nelson
(74) *Attorney, Agent, or Firm* — Tutunjian & Bitetto, P.C.

(57) ABSTRACT

Multi-layer anti-fouling coatings include a first biocidal layer formed on a surface. The first biocidal layer includes at least one biocidal biocide that kills a biofouling organism on contact with the first biocidal layer. A first biostatic layer is formed between the first biocidal layer and an external environment. The first biostatic layer includes at least one biostatic biocide that inhibits a biofouling organism from attaching to the first biostatic layer.

16 Claims, 27 Drawing Sheets

(56) References Cited

U.S. PATENT DOCUMENTS

| | | |
|---|---|---|
| 8,372,418 B2 | 2/2013 | Dujardin et al. |
| 8,840,910 B2 | 9/2014 | Masuda et al. |
| 9,968,093 B1 | 5/2018 | Ribot Barroso et al. |
| 9,968,094 B1 | 5/2018 | Ribot Barroso et al. |
| 9,968,095 B1 | 5/2018 | Ribot Barroso et al. |
| 2005/0136087 A1 | 6/2005 | Freehauf |
| 2006/0089342 A1 | 4/2006 | Gavin et al. |
| 2010/0144888 A1 | 6/2010 | Bessette |
| 2010/0210745 A1* | 8/2010 | McDaniel ............... C09D 5/008 521/55 |
| 2014/0141263 A1* | 5/2014 | Jones ................... C09D 5/1625 428/447 |
| 2015/0086719 A1 | 3/2015 | Van der Flaas et al. |

FOREIGN PATENT DOCUMENTS

| | | |
|---|---|---|
| EP | 1175255 A1 | 1/2002 |
| EP | 1189504 B1 | 12/2012 |
| EP | 2037914 B1 | 10/2013 |
| EP | 3078715 A1 | 10/2016 |
| JP | S5998200 | 6/1984 |
| TW | 200618892 A | 6/2006 |
| WO | 2008104851 A2 | 9/2008 |
| WO | 2009150437 A2 | 12/2009 |
| WO | 2012001668 A1 | 1/2012 |
| WO | 2012085630 A1 | 6/2012 |
| WO | 2015011177 A1 | 1/2015 |
| WO | 2015011178 A1 | 1/2015 |
| WO | 2015082397 A1 | 6/2015 |
| WO | 201618249 A1 | 11/2016 |

\* cited by examiner

| Key Pesticide – Insecticide Water Solubility Table: < 20 mg/L: | | | |
|---|---|---|---|
| Insecticide | Water Solubility mg/L | Aquatic Toxicity* | $K_{OC}$ |
| Abamectin | 5 | high | 5,000 |
| Bifenthrin | 0.0001 | very high | 237,000 |
| Chlorpyrifos | 1.18 | extremely high | 9,930 |
| Cyfluthrin | 0.02 | extremely high | 100,000 |
| Cypermethrin | 0.004 | very high | 61,000 |
| Diflubenzuron | 0.08 | very low | 8,700 |
| Dislfoton | 12 | high | 600 |
| Endosulfan | 0.32 | very high | 12,400 |
| Esfenvalerate | 0.0002 | very high | 5,300 |
| Fenpropathrin | 0.014 | very high | 5,000 |
| Fipronil | 2 | very high | 838 |
| Lamda-cyhalothrin | 0.005 | very high | 180,000 |
| Lufenuron | 0.06 | low | ? |
| Ivermectin | 4 | high | 15,700 |
| Permethrin | 0.006 | very high | 100,000 |
| Phosmet | 20 | very high | 668 |
| Spinosad | 89 | very low | 16,420 |
| Tebufenozide | 0.83 | very low | 389 |
| Thiodicarb | 19.1 | high | 351 |
| Talomethrin | 0.001 | very high | 100,000 |

FIG. 21A

| Key Pesticide – Miticide Water Solubility Table: < 20 mg/L: | | | |
|---|---|---|---|
| Mitocide | Water Solubility mg/L | Aquatic Toxicity* | |
| Avermectin | 5 | high | 5,000 |
| Bifenazate | 4 | moderate | 4,600 |
| Clofentezine | 0.0025 | high | 45,300 |
| Dicofol | 0.08 | high | 6,064 |
| Fenbutatin oxide | 0.0127 | very high | 2,721 |
| Heythiazox | 0.6 | moderate | 6,200 |
| Ivermectin | 5 | high | 15,700 |
| Propargite | 0.6 | high | 41,000 |
| Pyridaben | 0.012 | very high | 110,000 |

FIG. 21B

Key Pesticide – Herbicide Water Solubility Table:

| Herbicide | Water Solubility Mg/L | Aquatic Toxicity* | $K_{CO}$ |
|---|---|---|---|
| Benefin | 0.01 | high | 9,000 |
| Bensulide | 6 | high | 1,000 |
| Dcpa | 0.5 | moderate | 5,600 |
| Diclofop | 0.8 | high | 16,000 |
| Dithiopyr | 1 | high | 800 |
| Fenoxaprop ethyl | 0.9 | high | 9,490 |
| Fluaxifop-p-butyl | 2 | high | 5,700 |
| Isoxaben | 1 | high | 1,400 |
| Mcpa | 5 | high | 1,000 |
| Oryzalin | 2 | high | 600 |
| Oxadiazon | 0.7 | very high | 3,200 |
| Oxyfluorfen | 0.1 | high | 100,000 |
| Pendimethalin | 0.3 | very high | 5,000 |
| Prodiamine | 0.01 | high | 13,000 |
| Propyzamide | 15 | high | 200 |
| Pyrithione Zinc | 12 | low | ? |
| Simazine | 6 | high | 130 |
| Thiazopyr | 2 | moderate | 400 |
| Trifluralin | 0.3 | very high | 7,200 |

FIG. 21C

Natural Plant Alkaloid Families Possessing Insecticidal Properties:

pinenes
terpinenes
anise
bitter orange peel
basil
sage extracts
pulegone
evening primrose
grapefruit extracts
lime extract
pimento leaf, berry
mustards
terpenoids
tangerine extract
turmeric
thunder god vine camphols
cinnamon extracts
anise extracts
cedar
canaga oil
clove extracts
vanillins
fennel
jasmine
mandarin extracts
pine extracts
nutmeg extract
sesame extracts
thyme extracts
white cedar cintronellins
achillea
pepper extracts
carnation
capsaicin
coriander
eucalyptus extracts
geranium extracts
lavender extracts
menthols
rose
sage extracts
soybean extracts
tomato extracts
lemongrass terpenes
salicylates
basile
camphor
citronella extracts
lemon, limonenes
eugenols
ginger
juniper berry
mints
rosemary
sandlewood
teas, tannins
thyme
chrysanthemum

FIG. 21D

METHODS AND COATINGS FOR PROTECTING SURFACES FROM BIO-FOULING SPECIES

BACKGROUND OF THE INVENTION

Technical Field

The present invention relates to anti-fouling coatings and processes to prevent bio-fouling of mechanisms and surfaces and, more particularly, to multi-layer anti-fouling coatings that include combinations of biostatic and biocidal substances that prevent attachment of bio-fouling organisms and, for any such organisms that penetrate a biostatic layer, that kill such bio-fouling organisms.

Description of the Related Art

Biofouling or biological fouling is the accumulation of microorganisms, plants, fungi, algae, or animals on surfaces. Antifouling is the ability of materials or coatings to remove or prevent biofouling by the huge number of organisms that are capable of colonizing and growing on wetted surfaces. While the most problematic of these organisms include shell-forming, invertebrate calcareous (hard calcium and shell forming) animals such as barnacles, mussels, and shipworms (marine wood borers), with photosynthetic algae also being of concern, up to 4000 different organisms comprising over 1700 different species that include fungi, bacteria, bryozoans can develop sufficient biomass on involved structures to constitute significant biofouling. More recently a new class of invertebrate organisms that are non-shell forming, the tunicates, have become a major environmental problem approaching that of calcareous animals. The proliferative ability of these organisms is remarkable and has reached a recorded high for barnacles of 343 kg/m2 in the South China Sea. Large masses of invasive biological species interfere with the function of every known device, structure, and surface submerged in either marine or fresh water.

Because biofouling can occur almost anywhere that water is a present, biofouling poses risk to a wide variety of objects such as underwater construction, submerged structures, desalination plants, hydroelectric dam and power installations, navigational and instrumented buoys, ocean wave energy converters, and recreational boating and commercial shipping. With respect to boats and vessels moving and being submerged in water, not only are the boat hulls subject to this phenomenon, but also engines, internal cooling and piping systems, propellers and other boat appendages such as struts, shafts, lights, and other structures can have their function compromised and can even be destroyed by heavy infestations of unwanted organisms. Fish nets, lobster and crab traps, electrical and support cables, and heat exchangers are further examples of devices that can be compromised with biofouling. The function of navigational and instrumented scientific buoys can be hampered because of destruction of instrumentation, and in some cases buoys can even sink from excessive weight gain from the attached weight of the invasive biofouling biomass. Wave energy harvesting generators can freeze up, lose function, be destroyed, and sink from attached biomasses of invertebrates.

Biofouling is a serious problem as related to the shipping industry, in particular the world shipping industry, and produces several serious issues via barnacle infestations greatly affecting both the economics of shipping, the performance of vessels being propelled through the water by various means, and the release of unwanted carbon emissions on the health of the planet. For instance, the hull structure and associated appendages can be damaged through corrosion and sea water seepage into the metal, even if the metal is a stainless steel alloy normally resistant to seawater corrosion. Engine structures can be destroyed through overheating by non-functional cooling systems, caused by liquid flow blockage by invasive organisms and corrosion damage. The accumulation of biofouling on hulls for a heavy infestation can increase drag and hydrodynamic friction by up to 60%, translating to a speed decrease of 10% for a given rate of fuel consumption. To compensate for this drag, up to a 40% increase in this fuel consumption can be needed.

While these problems are also plaguing the leisure boating industry, from mussel infestations in freshwater and from barnacle infestations in saltwater, the barnacle infestations are more responsive for negative planet-wide effects. With fuel typically comprising up to half of marine transport costs, antifouling methods are estimated to be able to save the worldwide shipping industry around $60 billion per year if completely effective solutions were implemented. Furthermore, barnacle biofouling has significant impact on global warming and weather changes due to increased fuel use, and it contributes to adverse environmental effects because of increased emissions of carbon dioxide and sulfur dioxide.

Marine fouling is typically described as following four stages of ecosystem development. The chemistry of biofilm formation describes the initial steps prior to colonization. 1) Within the first minute, the van der Waals interaction causes the submerged surface to be covered with a conditioning film of organic polymers. 2) In the next 24 hours, this layer allows the process of bacterial adhesion to occur, with both diatoms and bacteria (e.g. *vibrio alginolyticus, pseudomonas putrefaciens*, etc.) attaching, initiating the formation of a biofilm. 3) By the end of the first week, the rich nutrients and ease of attachment into the biofilm allow secondary colonizers of spores of macroalgae (e.g. enteromorpha intestinalis, ulothrix) and protozoans (e.g. vorticella, *Zoothamnium* sp.) to attach themselves. 4) Within 2 to 3 weeks, the tertiary colonizers—the macro-foulers—have attached. These include tunicates, mollusks and sessile Cnidarians, and the organisms include barnacles and shipworms in bodies of salt water, and invasive *quagga* and zebra mussels in fresh water bodies including rivers, lakes, and estuaries, along with Mediterranean mussels in Asia. Finally, non-calcifying invasive tunicate organisms including Sea Grapes and Golden Heart tunicates have invaded much of the Canadian and US Atlantic and Pacific Coasts.

Once attached, the larval forms of these macro-fouling organisms develop quickly, and in the case of the barnacle larva, cyprids, once they complete the process of metamorphosis into the juvenile form, an event that takes only 6 to 24 hours to complete after attachment, they immediately begin using their nascent shell formative process to begin burrowing into the attached surface, eventually developing into a destructive biomass that reaches maturity in one to five years. The process is similar for invasive mussel species, *quagga* and zebra mussels, where the two invasive species of mussels overrun the entire sea bottoms and shores of huge lakes like Lake Mead, Lake Powell, and the Great Lakes in the US. These invasive animals having spread, along with barnacles in sea water from the area of the Caspian Sea, across Europe, to the US, and to the rest of the world by their larval forms carried in ship plumbing and ballast tanks, as well as adult forms on the hull and other boat structures. According to the National Parks Service, US Department of the Interior, there have been no known effective methods of prevention or treatment for eradication of invasive mussels and tunicates that are environmentally practical or safe, and the treatment and prevention of barnacle infestations are highly unsatisfactory.

The destructive mechanisms by which calcium-forming invertebrates take their toll on even the toughest coatings and substrates can be illustrated by the actions of barnacles on 316L stainless steel. This alloy is totally impervious and not corrosive in freshwater, and virtually so in salt water as this alloy requires for protection, especially from the chloride ion in salt water, a passivated thin surface layer of chromium oxide 100 angstroms thick. The layer is maintained by constant renewal of the oxide from oxygen dissolved in the water. The mechanism of barnacle destruction of stainless steel can even reduce this 316L alloy to rust via barnacle induced bio-corrosion, pitting and crevice corrosion.

A barnacle larva settles on the stainless steel surface by penetrating the biofilm and metamorphoses to a juvenile adult in 6 to 24 hours, followed by repeated molting cycles secreting its adhesive barnacle cement to spread to fill the gap between the base plate of the enlarging barnacle and the substrate, curing in over a period of a few hours, and repeating the process with the shell enlarging each time. The cement reacts with the protective chromium oxide layer thereby disrupting it, especially at the exposed grain boundaries of the metal, creating channels for corrosive seawater to flow inside the crevice formed by the barnacle which, in turn, starts attacking the steel metal grains. Severe rusting and the formation of pits occur destroying the steel. The cycle is repeated with every enlargement of the juvenile barnacle until adulthood is reached, and by that time severe damage has been sustained over an area of the diameter of the barnacle base, multiplied by the great number of barnacles, and the stainless steel surface is destroyed. A very similar process occurs with invasive mussels, though the bio-corrosion is less, for instance on stainless steel leisure boat propellers, because no chloride ion is present.

Many solutions to biofouling have been deployed over the millennia. Copper sheathing were once used, but the rise of iron and steel ship siding led to an end to this practice because of the galvanic action and corrosion resulting from the interaction of copper and iron. Copper oxide-based paints have also been used, but had limited lifespan due to leeching into the water and because of the chemical conversion of the cuprous oxide into less toxic salts which accumulated as a crust which would inhibit the further biocide action of the copper.

Self-polishing, tin-based biotoxic paints have been used as well, but were so toxic that they have been banned worldwide. While modern adhesives permit application of copper alloys to steel hulls without creating galvanic corrosion, copper alone is not impervious to diatom and algae fouling. Furthermore, some studies indicate that copper may also present an unacceptable environmental impact, as the fact that cuprous oxide and other copper salts such as copper thiocyanate are converted into copper oxychloride, which while bio-toxic for biofouling animal species, is also highly toxic to desirable aquatic species, leading to it being banned from use in several jurisdictions.

BRIEF SUMMARY OF THE INVENTION

A multi-layer anti-fouling coating includes a first biocidal layer formed on a surface. The first biocidal layer includes at least one biocidal biocide that kills a biofouling organism on contact with the first biocidal layer. A first biostatic layer is formed between the first biocidal layer and an external environment. The first biostatic layer includes at least one biostatic biocide that inhibits a biofouling organism from attaching to the first bio static layer.

BRIEF DESCRIPTION OF THE DRAWINGS

FIG. 21A gives a table of low water solubility insecticides effective against invasive invertebrate biofouling organisms;

FIG. 21B gives a table of low water solubility miticides effective against invasive invertebrate biofouling organisms;

FIG. 21C gives a table of low water solubility herbicides effective against invasive plant biofouling organisms; and FIG. 21D gives a table of natural plant alkaloids that are known to be natural pesticides of organisms belonging to the phylum Arthropoda.

DETAILED DESCRIPTION

Figure 1A:
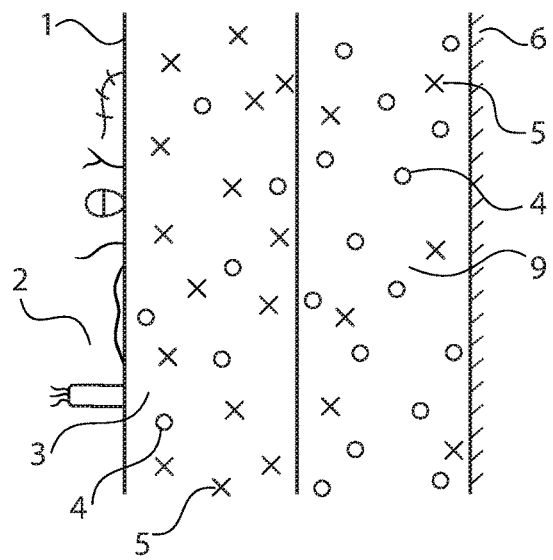
FIG. 1A depicts a cross section of an anti-fouling coating with an outer biostatic polymer layer and an inner biocidal polymer layer.

Embodiments of the present invention place environmentally safe antifouling formulations, specifically optimized for any given appropriate application, onto any stationary or moving structure or material surface in contact with or submerged within either marine or fresh bodies of water. The present embodiments prevent and control biofouling of structural surfaces submerged in still or moving saltwater or freshwater by invasive, invertebrate, calcium-forming biofouling species such as mussels, barnacles, and shipworms. These embodiments may include a multi-layer polymer coating structure of variable thickness polymer layers impregnated with biocides whose composition within the coating varies with depth from the surface of the water. The composition of biocides impregnating an outer portion of the antifouling coating produce a primarily biostatic antifouling effect, preventing and inhibiting all larval forms of invertebrate organisms from attaching and inhibiting their permanent implantation on the protected surface, and the composition of biocides impregnating an inner portion of the antifouling coating produce a primarily biocidal effect by killing on contact all invasive organisms that have metamorphosed to the juvenile form and that have managed to penetrate the outer biostatic polymer layer secondary to partial resistance to the biocides in that layer. The outer biostatic polymer layer acts to shield the inner biocidal polymer layer, which has the more potent biocidal biocides, from contact with the water, reducing any chance for undesirable effects on the aquatic environment and its beneficial lifeforms. Complex differing multi-biocide compositions within the two polymer layers are chosen to employ polychemotherapeutic principles of human cancer chemotherapy and human infection antibiotic therapy, producing more effective attachment inhibition, lethality, cessation of reproduction, less chance of developing resistant biofouling strains, and finally stopping the proliferation and spread of these organisms.

Because attachment of algae encourages biofouling organism implantation and is of cosmetic concern to the leisure boating industry, a phytotoxic algaecide may also be impregnated into the outer polymer layer. While the present embodiments prevent and eradicate hard biofouling invertebrate agents, with a modification of adding one additional biocide, an algaecide such as pyrithione salt mixture that is also relatively insoluble in water and thus again will not release undesirable heavy metal ions into the surrounding water, some embodiments can be biocidal to algae, bacteria, and fungi, and biofilm. Buildup of biofilm is the precursor for the invasion of soft algae biofouling organisms and its associated unpleasant cosmetic effects, and is also the precursor for the invasion of hard invertebrate biofouling organisms and their associated destructive effects.

Furthermore, it was determined through field testing that combinations of algaecides with either the biostatic biocides or biocidal biocides are also extremely active and effective against the invasive biofouling tunicate species that include Golden Heart Tunicates and Sea Grape Tunicates. These biocides present effective methods of prevention and treatment of these non-shell forming invertebrate organisms that previously have been resistant to all treatments. These invading tunicates are so invasive and virulent that they will grow on an invasive biofouling biomass of barnacles or on masses of invasive as well as commercial mussels to smother and kill these organisms to become the dominant biofoulers.

The present embodiments provide biocidal coatings that are safe to the aquatic environment and the benign and beneficial organisms that reside, that cause minimal effect on both the animal and human food chains, that are safe with respect to human exposure and human carcinogenicity, and that are cost effective, economical, and available in commercially large quantities. As a result, many of biocides that are most suitable for the purposes of the present embodiments are naturally derived plant compounds, and the few artificially constructed molecules as well as metal derived biocides are chosen to not only provide anti-fouling function but also to be completely safe for the aquatic environment and the benign and beneficial organisms that reside in that environment.

Defining Basic Terms:

Biofouling organisms: Organisms which have the ability to attach to, colonize on, proliferate on, and then penetrate the surface of objects or the protective surface of such objects that are exposed to or submerged in aquatic environments including salt water, fresh water, and brackish water, resulting in the cosmetic defacement, corrosion, decomposition, and destruction of such surfaces, and if the surfaces involve structures moving within the aquatic medium, interference with such motion through increase frictional resistance; "Soft" biofouling organisms include: bacteria, mold and fungi, freshwater and marine green, blue green algae, gold algae (diatoms), and marine and freshwater seaweeds as well as invasive tunicates (Phylum: Chordata, Subphylum Tunicata, Class: Ascidia) including in particular Sea Grapes (Mogula manhattensis), Golden Heart (Botryllus schlosseri), and numerous other species; "Hard" biofouling organisms include calcareous calcium, chitin, and shell Forming Organisms that include (but are not limited to) the following classes of biofoulers:

Barnacles—Kingdom: Animalia, Phylum: Arthropoda, Subphylum: Crustacea, Class:

Maxillopoda, Subclass: Cirripedia, Family: Theoctraca, Genus: *Balanus*, Species: *B. Grandula* (common acorn barnacle), *B.Crenatus* (Crenate Barnacle), *B. nubilus* (Giant Barnacle), *B. perforates, B. Amphibalanus improvisus* (Bay Barnacle), *Megabalanus coccopoma* (Titan Acorn Barnacle, Georgia), B, *Balunus, B. Amphitrite*, and *Polliceipes polymerus* (Gooseneck Barnacles), and approximately 50 others; they are chitin and calcium forming;

Mussels—Kingdom: Animalia, Phylum: Mollusca, Class: Bivalvia, Order: Veneroida, Family Dreissenidae, Genus: *Dreissena*; they are calcium and chitin forming organisms that include:

Zebra Mussel—Species: *Dreissena polymorpha*,

Quagga Mussel—species: *Dreissena bugensis*

Mediterranean Mussel—Order: Mytiloida Family: Mytilidae Species Mytilus galloprovincialis (Invasive in Asia only);

Marine Shipworms (Marine Woodborers)—Kingdom: Animalia, Phylum: Mollusca, Class: Bivalvia, Order: Myoida, Family—Teredinidae, Genus: *Teredo, T. Navalis* (most prevalent), *Xylophaga dorsalis, Psiloteredo megotara, Nototeredo norvagica*; Crustacea Family—Limnoria lignorum ("gribble"); they are chitin and calcium forming organisms;

Bryozoans—Chitin and calcium forming species—many.

Invasive non-barnacle crabs and shrimps—Kingdom: Animalia, Phylum Arthropoda, Subphylum: Crustacea, various Genus and species; *Glabrophihummus seminudus* (Pilumnid crab—native to central Pacific and invasive to Hawaii via ships from Guam), *Carup tenuipes* (portunid crab—native to the Atlantic and invasive via the Suez Canal to the Mediterranean Sea spreading by ships to New Zealand and Hawaii), *Gonodactylaceus randalli* and *Gonodactylaceus falcatus* (mantis shrimps via US navy ships from their native Phillipines to Hawaii) and others; they are chitin and calcium forming organisms.

Polymer—refers to a member of a class of chemical compounds or mixture of chemical compounds formed by the process of polymerization where two or more molecules combine to form larger molecules that contain molecular chains of repeating structural units. The pertinent classes of polymers relevant to this invention which can comprise either one or two part liquid polymers for coatings or solid polymers for comprising three dimensional structures include as representative examples, plastics, and non-plastic polymers:

Plastics:

Member sub-classes of this class of compounds with representative examples include:

Poly vinyl chlorides—Plasticized, un-plasticized, and high impact, chlorinated PVC, and others;

Polystyrenes—High impact, general purpose, ABS (acrylonitrile-butadiene-styrene copolymer), Styrene-Acrylonitrile copolymer, Styrene-butadiene-styrene co-polymer, Styrene-Butadiene, and others;

Celluloses—Cellulose acetate, cellulose acetate-butyrate, cellulose acetate-propionate, Cellulose Propionate, and others;

Polyethylenes—Low density Polyethylene, Medium Density Polyethylene, very low density Polyethylene, chlorinated polyethylene, polypropylene homo-polymer and copolymer, High density polyethylene, ultra-high molecular weight polyethylene, and others;

Acrylics—Polymethylmethacrylate, Polyphenylene oxide, Polycarbonate, ethylene-vinyl acetate, ethylene-methyl acrylate and others;

Nylons—Polyamides of many types;

Polysulphones—of many types;

Liquid crystal polymers—many types

Fluoropolymers—polytetrafluoroethylene (PTFE), polyfluoroethylenevinyl ether (PEVE), (also known as fluoroethylenevinyl either (FEVE)), poly-flourourethanes, perfluorosulfonic acid, Perfluoropolyethelyne either, and many others;

Resins: acrylic resins, epoxy resins, phenolic resins, polyurethane resins, polyester resins, and others;

Non-Plastic Polymers:

Silicon Based Polymers—silicones (polysiloxanes), silanes, silicone Rubber—liquid and gel, fluorosilicones, and others;

Rubbers—natural rubber (latex, isoprene, cis poly-isoprene), neoprene (poly-chlorprene), BUNA-S (butadiene-styrene co-polymer), BUNA-N (nitrile rubber), butyl rubber, Ethylene-propylene-diene-monomer (EPDM), acrylic rubber, fluoroelastomers (Viton), and others.

Pure Carbon Polymers—graphite, activated carbon, graphene, graphene nano-platelets, graphene oxide, graphene fluoride.

Primer—or undercoat, is a preparatory coating put on materials before painting of a coating or topcoat, so as to ensure better adhesion of the paint or coating to the underlying surface, that in addition increases durability of the applied coating or paint, provides for uniformity in the coating's thickness, prevents bleed through of impurities from the surface being painted, and provides additional protection, by building up the primer thickness with repeated coats, for the material being painted. A primer's composition may include varying amounts of resins of the categories defined above under resin polymers, solvents, pigments, particulates to reinforce the primer such as Kevlar, silica, fluorspar, carbon fiber, boron and other carbides including silicon and metal carbides, cubic boron nitride, industrial grade diamond, and stainless steel fragments, as well as other chemicals and particulate additives.

Examples of primers include:

Self-Etching Primers including acid and zinc chromate, zinc phosphate primers; epoxy primers, zinc rich epoxy primers, polyester primers, latex primers, poly-vinyl acetate primers, aluminum-rich epoxy primers, acrylic primers, and urethane primers. The zinc rich-epoxy polymer primer has excellent antifouling properties because of the zinc powder component, which may be as high as 90% (by weight) of the primer.

For the purposes of the present embodiments, there are four structural classes of polymers that compose the structure of the antifouling coating. They are designated as follows:

Polymer-O, an outer, biostatic polymer topcoat exposed to the water environment, that covers a second biocidal inner polymer that may also be a polymer primer layer;

Polymer-I, an inner, biocidal polymer undercoat that is not exposed to the water environment and covers either the surface to be protected itself or covers a primer polymer that covers the surface to be protected;

Primer-O, an outer polymer primer that, if used, would be used between the outer Polymer-O layer and the inner Polymer-I layer;

Primer-I, an inner polymer primer or non-polymer primer that, if used, would lie between the inner Polymer-I layer and the surface to be protected.

A pesticide, or biocide is defined as any substance toxic to undesirable plant and animal life and may include any chemical agent (including metals, alloys, or inorganic salts of metals or alloys), organic chemical, or metallo-organic chemical capable of preventing unwanted or invasive biological organisms, including animals (insecticides, herbicides, ascaricides, mitocides) or plants (herbicides, algaecides, fungicides, bactericides), from proliferating either through direct killing of their cells by interference with cellular metabolic processes (a biocidal biocide), or by creating an unfavorable environment so that, while they are not killed, they will not colonize an area and proliferate (a biostatic biocide).

Of particular relevance is the subclass of pesticides that have low water solubility, low leachability, low aquatic toxicity, and low human toxicity. This subclass may be divided into two further subclasses, organic pesticides and the metal-derived pesticides, with a small number of organometallic pesticides that have characteristics of both. The pertinent classes of pesticides include members of the chemical classes of compounds listed below that possess a low water solubility requirement of <100 mg/ml, (100 mcg/microliter) but preferably <20 mg/ml (20 mcg/microliter).

Exemplary insecticides that can be used in the present embodiments include insecticides listed in FIG. 21A; mitocides listed in FIG. 21B; Herbicides listed in FIG. 21C; Natural plant alkaloids such as capsaicin listed in FIG. 21D as well as other Chinese herbal insecticides in particular for instance, the extract of *Triptergium wilfordii* (thunder god vine) which contains three potent insecticides—celastrol, triptolide, and wilforine with favorably extreme water solubilities of <1 mg/L, 0.017 mg/L, and <1 mg/L respectively; Organic hydrocarbon anti-helminthics such as ivermectin but also including a large number of chemical analogues known as macrocyclic lactones, natural products originally derived from soil fungi and bacterial organisms and their chemical derivatives, a family of drugs known as the avermectins (Abamectin, Aversectin C, Doramectin, Emamectin, Eprinomectin, Ivermectin, Selamectin, Milbemectin, Mibemycin, Moxidectin, Lepimectin, Neamdectin, Spinosad, and Spinetoram, and others), as well as other anti-helminthics such as albendazole and its chemical analogs with low water solubility (<1 mg/L) as well as lufenuron with an extremely low water solubility of <0.06 mg/L; inorganic and metallo-organic pesticides—only Cupronickel (90% Cu, range 66-33%; 10% Ni, range 9-30%; 1% Fe, 1% Mn) and its closely related alloys cuprozinc and cuprosilver, are relevant as useful to the present embodiments, as the others—copper metal, copper oxide, copper thiocyanate, zinc metal, zinc oxide, and most certainly tributyltin (TBT) are considered too toxic to the aquatic environment to be desirable for the present embodiments, even though a feature of the present embodiments allows these metal biocides to be safely used by prevention of chemical leaching into the surrounding water. Nevertheless, TBT is expected to be permanently banned, and in some jurisdictions, copper salts are also being banned. Further examples include miscellaneous agents such as amitriptyline, imitriptyline and other chemical analogs of the tricyclic human anti-depressant medications; Pyrethrins and Pyrethrinoids including: Bifenthrin, Cyfluthrins, Cypermethrins, Cyphenothrin, Deltamethrin, d-phenothrin, Esfenvalerate, Etofenprox, Fenpropathrin, Flumethrin, cyhalothrins, Imiprothrin, Momfluorothrin, Prallethrin, Permethrin, Pyrethrins, Fluvalinate, Tefluthrin, Tetramethrin, and others.

The ideal biocide for the purposes of the present embodiments has the following characteristics: 1) a large molecule with a high molecular volume, allowing it to be better trapped within a polymer molecule matrix; 2) a high adsorption coefficient (KOC) as defined approximately as the ratio of the concentration of the biocide in the aqueous solution above a matrix to the concentration of that biocide in that matrix which may be soil or for the purposes of this invention, a polymer molecular matrix, where a high KOC indicates a high affinity for the matrix and a low affinity for the solution above the matrix; 3) low water solubility, which is related to factors 1) and 2); 4) low chemical leaching rate which is related to factors 1), 2), and 3); 5) Low environmental hazard to benign and beneficial organisms in the aquatic environment which is related to factors 1), 2), 3) and 4) as well as the biocide's intrinsic toxicity to such organisms; 5) no chlorine atoms or metal atoms, such as tin, incorporated into the biocide's organic molecular structure as chlorinated hydrocarbons and compounds such as TBT are quite toxic to environmental animal life relative to other; 6) biocides not having affinity for the food chain of higher organisms such as fish and humans leading to toxic effects in those species, including human carcinogenicity; 7) The ability for the biocide to biologically or spontaneously be degraded in the environment such as by UV light; 8) Low toxicity to commercial crustaceans, mollusks, and other beneficial organisms; 9) Absence of delayed toxicity, including carcinogenic, teratogenic, and mutagenic effects; 10) Wide spectrum of organism activity; 11) Simultaneous effects on settlement, adhesion, attachment, and causation of significant lethality before extensive growth and maturation followed by proliferation has occurred; 12) High potency allowing small loading factor concentration in the polymer matrix and long effective life; 13) Relatively safe for humans to apply as a biofouling coating; 14) Multi-year protection; and 15) Having a low diffusion constant, making the biocide more difficult to leach out into the water.

In general, a very high KOC is associated with a very low water solubility. For example, with respect to soil and water runoff, ivermectin has a very high KOC of 12660 to 15700 and a low water solubility of 4 mg/L; pyrethrins have a very high KOC of >100,000 and water solubilities as low as <0.1 mg/L, while spinosad D, another macrocyclic lactone derived from a fermentation bacteria, has a KOC of 34,600 and a water solubility of only 0.5 mg/L. Exceptions do occur, and a high KOC may characterize a compound with a high water solubility, indicating that it dissolves well in water while at the same time being attached to the matrix underneath—these compounds are not suitable for biocides for the purpose of the present embodiments as they are considered too toxic. However, if the adsorption coefficient is quite high, a somewhat higher water solubility of the biocide can be tolerated for this invention, such as commercial mixtures of 5:1 of spinosad A and D with a water solubility of 89 mg/L and 0.5 mg/L respectively but with a KOC 34,600 would still be useful as a biocide. It is specifically contemplated that biocides with a water solubility of <20 mg/L, and a KOC of at least 10,000 will be used with the present embodiments, but a water solubility of up to 100 mg/L and a KOC as low as approximately 500 may be used instead.

Although chlorination of an organic molecule is generally associated with high water solubility, high toxicity to benign and beneficial organisms in the aquatic environment, and a low KOC, if the molecule has many fluoride atoms as well, a high level of fluoridation of the molecule will make it highly water insoluble because of the hydrophobicity of the multiple carbon fluorine bonds, making acceptable for use with this invention. For instance, lufenuron has 2 chlorine atoms but 8 fluorine atoms, resulting in an exceptionally low water solubility of <0.06 mg/L.

Low water solubility does not guarantee a lack of aquatic toxicity, as various organo-tin compounds such as TBT have water solubilities ranging from 1.0 to 20 mg/L but are nevertheless far too toxic for use. TBT toxicity is not just based on its water solubility but also on the fact that the ablative paint that is impregnated with it disintegrates as well into the water with time, leaving toxic residues in the ocean sediment that persist for decades. Whatever the water solubility of the biocide is, no matter how low, if the resulting concentration of the biocide in the aquatic environment is still above the toxic range, as is the case with TBT, it would generally be too toxic for use in the present embodiments. However, even in this case, one particular embodiment of this invention can make even the use of TBT safe for the environment.

Water solubility is related to the chemical leaching rate of the biocide, which not only affects the toxicity of the biocide to desirable aquatic life but also affects the longevity of the effectiveness of the biocide. It has been shown by the paint industry, with measurements on organo-tin and copper paints, that the release rate of the biocide steadily drops for the first 14 days and then stays approximately constant until the end of the useable life of the biocide coating, at which point about 30% of the remaining biocide stays within the coating and is never released and about 70% has been released. Thus the effective operational life of the coating is dependent on the concentration by weight and therefore total amount of biocide in the coating. How long it takes that 70% to be released depends on the release rate over a given time. The lower the release (leaching) rate, the lower the biocide's aquatic toxicity and the longer the period of time that the biocide is effective for a given amount of biocide originally present in the coating. The present embodiments therefore make this release rate as low as possible.

The Higuchi Model of release (leaching) rates of a compound into an aquatic medium informs the selection of biocides forming the compositional embodiments of this invention. The equation that governs the release rate is $$RR = \sqrt{2DSe(A - 0.5Se)t} = \sqrt{K_h t}$$

where RR is the release rate or amount of drug released in a time period t for the area exposed to water, usually expressed in µg/cm2/day or ng/cm2/day, D is the diffusion coefficient characteristic of the biocide that gives an indication of how rapidly a chemical compound will diffused from a region of high concentration to a region of low concentration and which is inversely related to the molecular weight and volume of the molecule, S is the aquatic solubility of the biocide, e is the porosity of the matrix (polymer in the present invention), A is the concentration by weight of the biocide expressed as a biocide density or weight of the biocide per cc3 of matrix, also known as the loading factor, e is the porosity of the matrix, and Kh is the Higuchi release rate constant of the Higuchi Model.

The leaching rate is proportional to the product of the Kh factor and the square root of the time exposure. For the purpose of this invention, the water solubility of the biocide, S, should be as low as possible (<20 mg/L), the diffusion constant, D, should be as small as possible, which correlates with as high a KOC as possible, which in turn correlates with as high a molecular weight and molecular volume as possible, with such a preferred biocide being much less likely to diffuse out of the matrix (the polymer coating in this invention). Also the porosity of the matrix, e, should be as low as possible which, for a polymer coating (and especially for flourourethanes) would be extremely low, and a loading factor concentration of the biocide within the matrix, A, should be as low as possible. The more potent a biocide is, the lower the loading factor concentration in the polymer matrix can be for a given effective lifetime, which also is of economic advantage as well as the fact that, if A is too high, the mechanical, chemical, and curing properties of the polymer could be adversely affected. The lower Kh is, the better the biocide is for the purposes of the present embodiments.

As an example, a low solubility biocide such as ivermectin results in a release rate between about 0.7 and about 3.0 ng/cm2/day (depending upon if the ivermectin was dissolved in an organic solvent or not, respectively) as compared to the release rate for copper in copper-based bottom paints of several µg/cm/cm2/day—roughly 30,000 times greater. With copper based bottom paints, the copper biocide is released over large areas the size of the ship's hull, whereas the ivermectin concentration in the outer biostatic polymer layer is very low, so while the relative concentration of ivermectin in the inner biostatic polymer layer is high, that inner biocidal polymer layer is shielded from the aquatic environment and the ivermectin leaching rate into the aquatic is virtually nil, at least millions of times less than with copper-based painted hulls. Furthermore, if a biostatic biocide like cupro-nickel is used in the outer polymer layer, where the measured aquatic concentration of copper ions is less than the limits of detection of 50 ppb (0.05 mg/L), under this circumstance, the Higuchi Model Release Rate goes essentially to zero. In fact, with the choice of such low water solubility biocides, low porosity polymer layers, high KOC adsorption coefficients (low diffusion constants), in all the embodiments of the present invention to be described the Higuchi Model Release Rate goes essentially to zero, so that the operating effective life time of the anti-fouling coating of the present embodiments is greatly prolonged not only by the very high durability of the polymer coatings, but also the extremely low release rate of the biocides into the aquatic environment, which also greatly diminishes the chances for undesirable effects on that environment.

With respect to undesirable effects on the aquatic environment and the benign and beneficial organisms that reside there, the outer biostatic layer is less potentially hazardous both for the chemical and physical reasons mentioned above and shields the water from contact with the more potentially hazardous inner biocidal layer. Also, when an occasional barnacle or mussel larva penetrates the outer layer and touches the inner layer as a juvenile, it is killed quickly and outright on contact. It has been experimentally observed that, when a polymer impregnated with a biocidal biocide such as ivermectin is exposed to barnacle or mussel larvae, and there is no outer biostatic attachment inhibiting polymer layer present, that larvae do attach regardless and grow on the surface of the polymer layer. The organisms with their tiny shells can be seen with a magnifying glass. However, no adult barnacle or mussel adults are seen weeks or months later, because the young juveniles are killed quickly as soon as the juveniles pierce the outer surface of the biocide impregnated polymer. With the present embodiments, the area of the puncture site of the inner layer is microscopic and thus nothing leaks out of the inner layer into the surrounding water.

The effective diffusion coefficient, D, of the biocidal biocides as well as the leaching area, S, of the inner biocidal layer are essentially zero, showing that the Higuchi Model Release Rate of the biocides in the inner layer is essentially zero. Thus, even TBT can be used within the inner polymer layer. There is no release of potentially hazardous inner-layer biocide other than through tiny microscopic pits with diameters of about 0.1 mm (the size of the juvenile barnacle or mussel that produced that pit) in the outer biostatic polymer layer. The area of that exposure of the inner biocidal polymer layer to the aquatic environment for a defect 0.1 mm in diameter is 0.00157 mm2 or $1.57 \times 10^{-5}$ cm2 per barnacle or mussel for the few organisms that manage to attach and pierce the outer biostatic polymer layer and reach the surface of the inner biocidal polymer layer. Compared to the typical biocides of today's soft ablative or hard leaching paints that leach their biocides, copper and otherwise, into the aquatic environment over an area as large as the boat's hull, the beneficial effects of the present embodiments on the aquatic environment are significantly improved.

One further benefit of the present embodiments, namely the shielding effect of the more potent biocidal laden biocidal Polymer-I inner layer by the outer biostatic Polymer-O layer, can be discussed in terms of the Higuchi Model. The model can be applied to each layer in turn. The description so far of the model corresponds to the situation for the outer bio static Polymer-O layer. The Higuchi Release Rate Constant Kh for each layer is for a given impregnated biocide in that layer and is strongly dependent on D, the diffusion constant of the biocide. Applying the Higuchi Model to the outer biostatic polymer-O layer, for each biocide in the outer biostatic polymer layer, the effective life of that biocide can be estimated to be the length of time it takes for 70% of the biocide leaches out, which determines the useable life of the of the outer coating to effectively repel barnacle and mussel larvae and prevent them from settling and attaching. For a given solubility of the biocide, S, loading biocide concentration, A, and porosity, e, of the polymer matrix, the period of antifouling effectiveness of the outer biostatic polymer-O layer will depend upon the diffusion constant, D, of the biocide. The effect of all the biocides present in the outer layer is a weighted average of these factors for all the biocides in the layer, including the average diffusion constant of each biocide. The average D of all the biocides in that layer should be as low as possible, both for the benefit of the environment, and for extending the effective operating life of the coating as long as possible. Hence the need for biocide molecules of high molecular weight, preferentially above 200 Daltons (molecular weight) and large molecular volume with complex molecular structure.

Applying the Higuchi Model to the more potent and potentially more environmentally unfriendly inner biocidal Polymer-I layer, because that layer is effectively shielded from the aquatic environment, these more potent biocides cannot leach out into the water. The average diffusion constant for all the biocides in the inner layer is essentially zero because they are blocked from leaching out by the outer layer. Thus even for the most toxic biocide known, TBT, if the Polymer-I layer were impregnated with this compound, the diffusion constant will still be effectively zero, the Higuchi Release Rate Factor would be essentially zero, and the environment would remain completely protected. Furthermore, a second beneficial effect occurs that, after several years, when all of the biocides in the Polymer-O layer finally have leached out, and larval forms can no longer be prevented from attaching and settling, the Polymer-I layer will still be intact capable of killing the juvenile biofouling organisms on contact as soon as they pierced the boundary between the Polymer-O and Polymer-I layers. An additional period of useable antifouling time thus elapses before the Polymer-I will fail, not because of leaching out of the biocides in that layer, but rather because the continued dying of juvenile forms on that layer will eventually cause a mass of dead juveniles on the surface of the coating in the form of a layer that will make it impossible for further arriving biofouling juveniles to get into contact with the biocides of the Polymer-I layer, such that a biofouling mass will begin to grow as these later arriving larval forms are allowed to settle, progress into juveniles, and adult animals, thus causing coating failure. The structure is stripped and repainted to avoid permanent irreversible corrosion and other damage to its surface.

The term capsaicin, as used herein, indicates any of the alternative capsaicin-related compounds. The term ivermectin, as used herein, indicates any of the alternative ivermectin-type compounds. The terms pyrethrin and pyrethrinoid indicate any of the alternative pyrethrin or pyrethrinoid type of compounds. Metal pyrithione salts are a representative member of the group of alternative algaecides (herbicides) listed in the table of FIG. 21C. The term biocidal biocide indicates any biocidal insecticides or miticides listed in the tables of FIG. 21A and FIG. 21B or the natural plant alkaloid biocides listed in the table of FIG. 21D, as well as any other insecticide, anti-helminthic, cupro-nickel and related metal alloys, and any human drug such as the tricyclic anti-depressants or any veterinary drug such as medetomidine that have shown anti-invertebrate anti-biofouling effects either with barnacles, invasive mussels, or shipworms and other calcareous bio-foulers, may be used as a component biocide in this invention, that referring to a polymer indicates that any plastic or non-plastic polymer in the previously defined list of polymers may be used as a component polymer in this invention, and that referring to a polymer primer indicates that any polymer primer in the previously defined list of polymer primer list may be used as a component polymer primer in this invention, with the specific exclusion of the non-polymer compound, zinc chromate, which is being excluded from use as a primer compound from this invention because of its human toxicity and carcinogenicity. The distinguishing features of the present embodiments are not determined solely by the specific biocide used in the invention, but rather it is the specific process of sequestering various biocides of a plurality of one or more of such biocides within a molecular and mechanical structure of multiple specific polymer layers that comprise a multi-layer polymer anti-fouling coating possessing a different biocidal concentration and composition as a function of depth and location within the anti-fouling coating so as to firstly, inhibit the growth and proliferation of biofouling organisms by inhibiting the settlement, adhesion, and attachment by multiple simultaneous biostatic and biocidal means of fouling organism larval forms by an outer first polymer layer of biostatic nature located in the outer layer of the anti-fouling coating adjacent to the water touching that coating and containing a first biocide composition, and then sequentially, and secondly, inhibiting the growth and reproduction by effecting a killing on contact of these organisms at the juvenile stage by multiple simultaneous biostatic and biocidal means of a second type of composition within an inner polymer layer of biocidal nature in the inner portion of the anti-fouling coating adjacent to the surface being protected, as well as allowing for the use of an inner polymer primer, if necessary, to enhance the adhesion of the inner polymer layer to the protected surface as well as an outer polymer primer, to enhance the adhesion, if necessary, of the inner polymer layer to the outer polymer layer. The need to use either an outer or inner primer polymer layers will depend the need to increase the adhesion between the inner biocidal and outer biostatic polymer layers or between the inner polymer layer and the surface being protected, which in turn will depend upon the properties and surface compatibilities of the polymers being used, the properties of the surface that is being protected, the nature of the surrounding water and its turbulence, and whether the surface is relatively still or moving at a high velocity relative to the water.

The taxonomy of hard biofouling organisms, when analyzed for similarities and differences, can predict certain commonalities that will allow a poly-pharmotherapeutic approach to their prevention, control, and eradication. Because barnacles are both members of the arthropod phylum and the crustacean subphylum, certain classes of chemicals that include insecticides and anti-helminthics will kill them as they would insects, and parasitic worm infestations in humans and animals. However, because they are also crustaceans, such chemicals, if they can kill barnacles, they can potentially kill desirable crustaceans in the aquatic environment such as lobsters, crabs, crayfish, and shrimp. Hence, the existence of the need for any insecticide or anti-helminthic that can control barnacles or mussels must be virtually water insoluble so that only the barnacles and mussels and no other organisms in the aquatic environment away from the application of the biocide at the site of barnacle infestation are harmed as well. One such biocide representative of compounds that can fulfill these requirements is the anti-helminthic Ivermectin which permanently paralyzes the nervous system of the barnacle by activation of certain membrane ion channels and it acts as a neuromuscular blocker like atropine poisoning which induces hyperpolarization of these animals' nerve cells. Ivermectin is a large molecule macrocyclic lactone derived from *Streptomyces avermitilis* with anti-parasitic activity. It has two structurally related compounds, ivermectin B1A and ivermectin B1B that are present in a 4:1 ratio mixture that is sometimes referred to as avermectin. Ivermectin exerts its anthelmintic effect via activating glutamate-gated chloride channels expressed on nematode neurons and pharyngeal muscle cells. Distinct from the channel opening induced by the glutamate nerve transmitter, ivermectin-activated channels open very slowly but essentially irreversibly.

As a result, neurons or muscle cell membranes remain in a hyperpolarized state that does not allow the transmission of nerve electrical impulses, thereby resulting in paralysis and death of the parasites. Neuromuscular blockade has been effective against virtually all species of the Phylum Arthropoda, Subphylum Crustacea, which includes all barnacle and invasive shrimp and crab species as well as species of the Phylum Mollusca, Class Bivalvia, which includes *quagga* mussels, zebra mussels, Mediterranean mussels, and shipworms. Ivermectin, because of its the low water solubility and the predictions of the Higuchi Model, protects benign and commercially beneficial crustacean and mollusk populations located away from the protected surface. Ivermectin does not readily pass the mammal blood-brain barrier to the central nervous system where glutamate-gated chloride channels are located. As a result, the parasitic hosts are relatively resistant to the effects of this agent. This pharmaceutical agent has been found to be effective against shell forming biofouling organisms, as well as a broad class of parasitic worms and larvae in humans and animals, lice and mites in various environments, and it is virtually water insoluble. The various molecules that make up the ivermectin class of drugs (Avermectin, Abamectin, Moxidectin, Selamectin, etc.) do not contain any chlorine atoms, as they were originally derived from a soil bacteria, and thus do not possess any of the toxicity presented to the aquatic environment generally associated with chlorinated hydrocarbons. These molecules also break down quickly due to the effect of ultraviolet light from sunlight permeating the water.

Another pharmaceutical agent that takes advantage of the common trends found in different taxonomic groups of biofouling organisms is the anti-fungal agent, lufenuron. It is an agent that deactivates an important enzyme, chitin synthetase, responsible for the production of chitin in insects, mites, lice. Furthermore, the since the protein matrix upon which calcium is laid down to form shells in *quagga* and zebra mussels, and barnacles, as well as the calcium exoskeletons of shipworms (marine wood borers), attaching calcareous bryozoans, and invasive shrimp and crab species is the same chitin that forms the exoskeleton of insect and arachnid arthropods, all of these animals will be beneficially destroyed by lufenuron. These hard fouling organisms are all killed by lufenuron because they cannot form and/or enlarge their shells and calcium exoskeletons because they cannot form the chitin framework of these shells to allow calcium deposition, and they die of exposure or by other mechanisms.

Beneficial crustaceans also contain chitin, including lobsters, shrimps, crabs, and cray fish among others, and can find the use of an anti-chitin, anti-fungal in the aquatic environment highly toxic. However, lufenuron, is water insoluble, and thus it renders its toxic reaction only to a susceptible organism directly in contact with it, rather than to other animals in the aquatic environment, because it cannot leech out, dissolve, and be transported away to other locations contaminating the environment. The maximum water concentrations of lufenuron are below the toxicity levels of these desirable organisms. Lufenuron is a chlorinated hydrocarbon with two chlorine atoms, which as a class of compounds as pointed out previously, is generally toxic to the environment in varying amounts depending upon the chemical. As noted above, however, the water insolubility caused by the presence of 8 fluorine atoms in lufenuron's molecule, plus other measures described herein, keep the biocides within the chemical coating and not in the water, making this agent safe for the aquatic environment.

Direct contact by the invasive biofouling organism with a biocidal biocide impregnated in a coating, rather than release of biocides into the water, is the best manner by which the calcareous animal can be killed. Killing the organism while it is still in a juvenile form, before it proliferates, will prevent the spread of such invasive species. Multiple biocides within each layer of the coating makes it less likely that resistance to the biocides will develop.

Pesticides that can accomplish direct and immediate cell killing are known as biocidal biocides. However, it can be shown that invasive calcareous species, such as barnacles, *quagga* and zebra mussels, shipworms, and calcifying bryozoans can be controlled by a second mechanism, namely by preventing attachment of biofouling larval forms to the threatened surface. This is effective because attachment is necessary for further growth and maturation into the burrowing juvenile form. There are chemical agents that can prevent these biofouling species from attaching to the target surface. This attachment of invasive calcium-forming species is mediated by microscopic larval forms suspended and traveling in the water (veligers for *quagga* mussels, zebra mussels, Mediterranean mussels, and ship worms, and cyprids for barnacles as examples). These larval forms need surfaces to survive and grow. If the animal is inhibited from attaching to the surface, then the animal will not only not attach to the target surface and be repelled from it, its life cycle will also be interrupted and it will die within two or three weeks after running out of stored nutrients unless it can find a suitable alternative place for attachment. Since such a biocide does not kill the organism directly on contact, but instead only prevents growth and proliferation and a possible delayed death, the pesticide is considered to be a biostatic biocide rather than a biocidal biocide. This distinction between biostatic biocides and biocidal biocides will be used throughout the present description.

A common food supplement, capsaicin, which is a natural plant alkaloid and an extract of the chili pepper, *Capsicum annuum*, has the property of being very irritating to the swimming larval forms and will repel them if they alight on a surface coated with a polymer impregnated with capsaicin. This food supplement, normally used to increase the spicy heat sensation of food, has been shown to be able to retard barnacle growth and attachment and thus kill them indirectly, but does not kill these organisms directly. Hence capsaicin is a biostatic biocide.

However, although capsaicin is biostatic, it nevertheless has been quite successful in repelling these organisms before they attach in their larval state, and it has the added benefit of being totally water insoluble. Thus its chemical leaching rate is very low, allowing for a prolonged effective operational life. Capsaicin further has no known ill effects on benign and beneficial aquatic organisms. It contains no undesirable chlorinated hydrocarbon structures. Capsaicin is an incredibly stable plant alkaloid that is insoluble in water (13 mg per liter, at 30° C.) and, in its pure form, is extremely powerful in its effect. It is unaffected by heat or cold and it retains its original potency over extended periods of time, through cooking and freezing. Pure Capsaicin equals 16 million SHU and most purified Capsaicin extracts of chili peppers, 95% Capsaicinoids and 5% other substances by weight, will contain by weight 69% Capsaicin (SHU 16 million), and related alkaloids, 22% Dihydrocapsaicin, (SHU 15 million), 7% Nordihydrocapsaicin, (SHU 9.1 million), 1% Homodihydrocapsaicin, (SHU 8.6), and 1% Homocapsaicin, (SHU 8.6 million) which calculates out for a 95% pure chili pepper extract, as used in the present invention, a Scoville Heat Unit rating of 14.3 million SHU as compared to the pure Capsaicin of 16.0 million SHU. Because of the need to keep any bioactive agents impregnated into a polymer coating free of any significant impurities, either pure capsaicin, or a 95% chili pepper extract may be used.

Organic impurities are detrimental to the use of capsaicin as a biocidal antifouling repellant because of undesirable breakdown of such organic impurities within the polymer coating. This may cause undesirable chemical and physical changes in the integrity of the polymer layer including discoloration, changes in the curing process, and loss of physical imperviousness to water. The purity concerns that apply to capsaicin also apply to the addition of any biocide or biostatic to any polymer layer, no matter what the biological agent might be, and thus only pure versions of any biological agent should be used.

The general structure of the present embodiments includes a polymer structure of an outer polymer layer and an inner polymer layer that optionally has an inner polymer primer between the inner polymer layer and the surface to be protected, and optionally an outer polymer primer between the inner polymer layer and the outer polymer layer. The outer polymer layer contains a mixture of biocides that gives that layer a biostatic function with respect to inhibiting the attachment and growth of larval and juvenile forms of biofouling organisms, while the inner polymer layer contains a mixture of biocides that gives that layer a biocidal function with respect to killing any immature biofouling organisms that manage to penetrate the outer polymer layer. Furthermore, the outer polymer layer also may be impregnated with an herbicide as well to inhibit plant biofouling organisms. Further embodiments of the two-layer polymer structure allow optionally for biocides to be introduced in either the inner or outer primer polymer layers, or both, if primers are needed to improve the adhesion of certain outer layer polymers to the chosen inner layer polymer or to improve the adhesion of certain inner layer polymers to the particular material of the surface to be protected. Hence, the primers themselves can participate in the anti-fouling function of the coating. Also, to increase the durability and adhesion of the polymer primers, their composition may include particulate matter including fragments of stainless steel, silica, cubic boron nitride, industrial diamond powder, carbon fiber, carbides of boron, metals and silicon, with a preferential embodiment using boron carbide, as well as any pigment particles that would give such layers color. Such particulate matter may be introduced along with the biocides in both the inner and outer polymer layer as well to improve their durability and resistance to abrasion.

With this specified mechanical and molecular structure and this specified composition, which varies within the anti-fouling protective coating depending upon the location of the specified polymer layer in the antifouling coating, a sequential process is created of control, inhibition, prevention of attachment and proliferation, and killing of the biofouling organisms on contact with the inner biocidal polymer layer. The different steps in this process occur at different sites within and on the multi-layer polymer coating.

Cytotoxic cell killing biocidal biocides are not in direct contact with the aquatic environment, but rather are contained in an inner polymer layer (Polymer-I) that is covered by an outer polymer layer (Polymer-O) with less potent, biostatic biocides. The outer polymer layer interfaces with the aquatic environment and prevents attachment of biofouling organism larvae forms (cyprids and veligers), thereby repelling them. Direct, on-contact cell killing is done by the inner biocidal polymer layer (Polymer-I) of the antifouling coating only when the small minority of remaining larvae that were not repelled by the outer layer have just undergone metamorphosis to juvenile organisms to penetrate the outer biostatic polymer layer (Polymer-O) to touch the inner biocidal polymer layer. This vastly diminishes the number of dead, calcified invertebrate animals that collect on the antifouling coating with time. This is extremely beneficial, as with prior antifouling coatings, each and every organism that touched and settled onto the protected surface either grew or died on the surface of the coating. Thus, with the previous antifouling coatings, to be effective, virtually all fouling animals would need to die.

While the organisms are indeed dead, however, their shells could serve as perfect sites for attachment of successive arriving organisms, sites that are nowhere in proximity to the biocide in the coating, thereby ensuring the survival of the new arrivals, and thereby ensuring the eventual failure of the prior art coatings. As a result, those coatings in general antifouling coatings last only one or two seasons.

While the outside layer of the present embodiments may be disrupted by the few larval forms that might be resistant to the biocides in the outer biostatic polymer layer, the defect in the outer polymer layer produced by the developing, microscopically sized larval and juvenile forms, no larger than 0.1 mm, is negligible. Likewise, the defect in the outer surface of the inner biostatic layer caused by the penetration of the ring-like edge of the early juvenile shell is of similar microscopic size, because the organism is killed upon contact with the inner biostatic layer while it is still small. As a result, both the outside biostatic polymer layer and especially the inside biocidal polymer layer remain largely intact. This immunity to damage from attaching invasive organisms, results in continued complete shielding of the inner biocidal polymer layer from any significant exposure or contact with the surrounding aquatic environment. Chemical leaching is prevented and the confinement of the more potent and more potentially hazardous biocidal biocides within the biocidal polymer membrane is maintained.

This structural arrangement of polymers leads therefore to increased safety to benign and beneficial organisms within the surrounding aquatic environment as well as a much greater lifetime because of the prevention of chemical leaching of the inner biostatic layer's biocides into the environment. In this manner, even the highly toxic biocide, TBT, and less toxic metallic biocides like copper and zinc salts and metals, can be safely contained within the inner biocidal polymer coating and away from the surrounding aquatic environment.

The purpose of having a biocidal biocide in relative low concentration, together with a biostatic biocide in relative high concentration, in the outer biostatic polymer layer in a preferred ratio of about 1:10 is 1) to give an enhanced, synergistic inhibiting biostatic effect on attachment by invertebrate larval biofouling organisms and, 2) to produce this enhanced inhibitory biostatic effect without the need for a high concentration of biocidal biocides in the outer biostatic polymer layer which might have a higher probability of producing an adverse effect on the surrounding aquatic environment and its benign and beneficial organisms.

However, a second biostatic biocide in sufficiently high concentrations may replace the biocidal biocide in low concentrations in the outer biostatic polymer layer. The purpose of having a biostatic biocide in relative low concentration together with a biocidal biocide in relative high concentration in the inner biocidal polymer layer in a preferred ratio of about 1:10 is 1) to give an enhanced, synergistic organism killing on contact biocidal effect on invertebrate biofouling juvenile forms that managed to develop from larval forms that include veligers for mussels and cyprids for barnacles that in turn managed to attach and develop piercing the outer biostatic polymer coating in spite of its biostatic effect, and 2) the biostatic component to organism killing is less important to the inner biocidal polymer layer to prevent attachment to the outer biostatic polymer layer. Nevertheless, its presence does help reduce the amount of biocidal biocide needed because of its synergistic effect with the biocidal biocide.

A second biocidal biocide in sufficiently high concentrations may replace the biostatic biocide in relatively low concentrations in the inner biocidal polymer layer. The range of the ratio of the biocidal biocide concentration to the biostatic biocide concentration in the outer biostatic polymer layer may range from about 1:1 to about 1:1000, with a preferred ratio being about 1:10 and the range of the ratio of the biostatic biocide concentration to the biocidal biocide concentration in the inner biocidal polymer layer may range from about 1:1 to about 1:1000, with a preferred ratio being about 1:10.

Exemplary biostatic biocides used in the outer biostatic polymer layer include ultra-pure capsaicin in a concentration ranging from about 0.01% to about 50% by weight, with a preferred range of about 0.1% to about 10%, cupro-nickel alloy powder (about 90% copper and about 10% nickel with trace amounts of iron and manganese) with a concentration ranging from about 0.01% to about 50% by weight with a preferred range of about 0.1 to about 10%, and low dose pyrethrin class of compounds in a concentration of about 0.01% to about 0.5%, with a preferred concentration of about 0.1% to about 0.5%. However, a suitable substitute may be made from the list of natural plant alkaloids listed in the table of FIG. 21D, which includes those alkaloids known to be effective against insect pests.

Exemplary biocidal biocides used in the inner biocidal polymer layer include ivermectin and similar chemical analogs used in a concentration of about 0.01% to about 50,% with a preferred range of about 0.1% to about 5%, lufenuron, in a concentration of about 0.01% to about 50%, with a preferred range of about 0.1% to about 5%, and high dose pyrethrin class of compounds in a concentration from about 0.5% to about 5% with a preferred concentration of about 0.5% to about 1%, together with the pyrethrin potentiating metabolism inhibitor, piperonyl butoxide used at a concentration of about 1% to about 10%, with a preferred concentration of about 4%. However, a suitable substitute may be made from a list of insecticides listed in table FIG. 21A or from a list of miticides listed in table FIG. 21B, as well as miscellaneous compounds like the human medications amitriptyline and imitriptyline and other members of the class of tri-cyclic depressants, and various anti-helminthics including albendazole and its low water soluble chemical analogs.

Any known chemical agent that has been observed to have activity against calcareous biofouling invertebrate organisms are suitable for and would fall under the purview of the current invention, provided the compound adheres to the toxicity, leaching, and solubility requirements of the application.

A high strength particle additive used to enhance adhesion of the polymer primer and enhance durability of either the polymer primer or either the inner biocidal polymer layer or the outer biostatic polymer layer may include boron carbide. However, a suitable substitute may be made from a group that includes high-strength metal particulates, such as stainless steel and titanium (on non-metallic surfaces only to prevent unwanted galvanic corrosion), fiber materials such as aramid fiber, fiberglass and carbon fiber, minerals such as silica, fluorspar, or carborundum, and industrial diamond powder, or ceramics such as boron carbide, metal carbides, silicon carbide, and cubic boron nitride. The particle size can range from less than about 1 micron (approximately <12,000 mesh) to about 100 microns (approximately 150 mesh) with a preferred size range of about 20 microns (approximately 530 mesh) to about 50 microns (approximately 270 mesh). The concentration of such additives can range from about 0.01% to about 50%, with a preferred range of about 1% to about 15%.

The frictional properties of the outer biostatic Polymer-O can be preferentially and favorably reduced by the addition of low-friction additives such as molybdenum disulfide powder, non-cubic boron nitride, silicone powder, PTFE powder, graphite flakes, and graphene nanoparticles. To enhance the friction-reducing effects, extremely small particle sizes of less than about 20 microns would be beneficial, with a preferred size of less than about 1 micron.

Embodiments that include an algaecide added to the outside biostatic polymer layer may use a metal salt of pyrithione, either zinc, or zinc mixed with either barium or silver in a concentration by weight of about 0.1% to about 20%, with a preferred range of about 1% to about 10%. However, a suitable substitution may be made from the selected herbicides listed in the table of acceptable herbicides of FIG. 21C. These lists of potential components to the composition of this invention are not meant to be exhaustive and it should be understood that other appropriate materials may be used instead.

When delineating the class of biocides effective against barnacles and mussels, it is to be remembered that barnacles are crustaceans, and crustaceans are arthropods. Insects are also arthropods. Therefore, any pesticide that is an insecticide that possesses effectiveness against arthropods will also be effective against barnacles, though some variation in efficacy might be expected. It is to be also noted that barnacles produce chitin like insects do, only that barnacles use it to act as scaffolding upon which they deposit calcium to form and grow their shells. Thus a biocidal biocide, the chitin synthetase enzyme inhibitor lufenuron, that is toxic to sea lice and other insects would also be toxic to barnacles, for when barnacles cannot produce chitin, they cannot produce their shells.

It is also to be noted that, although mussels belong to the next primitive animal phylum, Mollusca, just below the evolutionary position of Arthropoda, and given that virtually any chemical substance that has been effective against barnacles have also worked against mussels, any biocide that shows effectiveness against arthropods will show effectiveness against invasive mussels. The reverse has also been shown to be true, namely that any biocide likely to show activity against invasive mussels will show activity against barnacles, given that their nervous systems and cell membrane receptors are similar and close to each other on the evolutionary scale.

Thus any biocide active against arthropods will be active against mussels, and any biocide that is effective against mussels, will therefore be effective against arthropods and, as a result, crustaceans, and hence barnacles, though some variation in efficacy is possible. Mussels, like barnacles, require the production of chitin for their shells and will die of dehydration if exposed to a chitin synthetase inhibitor such as lufenuron. Both the larval form, veligers, that are common to zebra, *quagga*, and Mediterranean mussels, and the larval form, cyprids, that are part of the barnacle life cycle, have GABA-a receptors on their nervous system which allows both of them to be repelled from attachment on surfaces containing chemical compounds that are GABA-a receptor modulators, such as capsaicin. Indeed, capsaicin will inhibit attachment of larval biofouling forms of both barnacles and mussels. The present embodiments make use of these intertwined taxonomic, physiologic, and metabolic relationships common to both mussels and barnacles, and other calcium forming biofoulers as well, to enhance the bio-toxicity to invasive mussels and barnacles through the use of multi-drug poly-pharmacotherapy. This intricately related arrangement of multiple polymer protective layers, with a biostatic arrangement of biocides on the outside of the coating and a biocidal arrangement of biocides on the inside of the coating, a composition that varies with the depth of the protective polymer coating and the layer in that polymer coating, will be a common feature of the present embodiments. At least two categories of embodiments are described: the first relating to the structure and function of the antifouling coating itself, and the second relating to applications to which this anti-fouling coating invention may be applied. The applications fall into seven classes of marine and freshwater anthropogenic (manmade) objects susceptible to biofouling: 1) Vessels, water conduits, and transport equipment; 2) Navigational and instrumented buoys and equipment; 3) Stationary structures including buildings, piers, bridges, pilings, sea walls, oil platforms, and bulkheads; 4) industrial pipelines, water intakes, power plant intake inlets, and filters; 5) Fixed submerged surfaces; 6) Flotsam, debris, and wrecked structures including historical shipwrecks; 7) Non-vessel operating machinery submerged in water. Additional applications involving filters, fishnets, fiber and rope, wave energy harvesting equipment, sea water electrolysis equipment, and engine cooling systems will also be described. It should be understood that this list is meant to be illustrative only and should not be construed as limiting.

Referring to FIG. 1A, a two-layer polymer structural embodiment of the biofouling coating is shown where the outer biostatic polymer layer 3 is adjacent to, and to the right of, inner biocidal polymer coating 9. The left hand side 1 is exposed to the aquatic environment 2. Biocidal biocide 4 is present in relatively high concentration in inner biocidal polymer layer 9 and in relatively low concentration in outer polymer layer 3. Any appropriate biocidal biocide, as described above, can be used. The Biostatic biocide 5 is present in relatively high concentration in outer biostatic polymer layer 3 and is present in relatively low concentration in inner biocidal polymer layer 9, which covers the surface to be protected 6. The surface 6 may represent metal, wood, plastic polymer, non-plastic polymer, ceramic, and so forth. In this embodiment there is no primer used between the inner biocidal polymer layer 9 and the protected surface 6 or between the inner biocidal polymer layer 9 and the outer biostatic polymer layer 3.

Figure 1B:
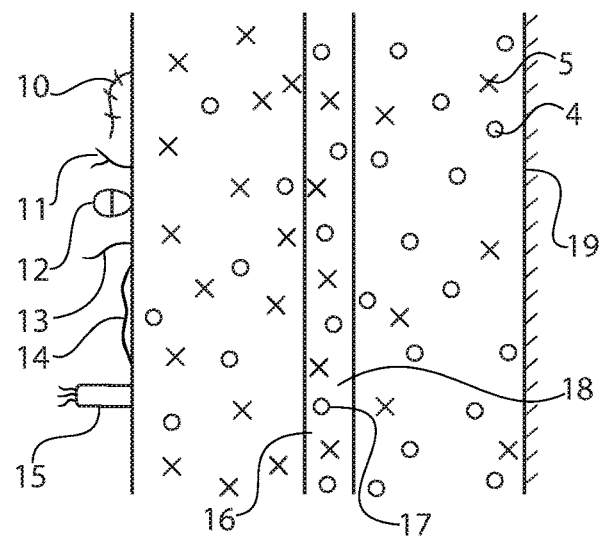
FIG. 1B depicts a cross section of an anti-fouling coating with an outer biostatic polymer layer and an inner biocidal polymer layer with an outer polymer primer between the two polymer layers.

Referring to FIG. 1B, a structural polymer layer embodiment of the present invention is shown where the following susceptible biofoulings attached to the water surface of Polymer-O: algae 10, bryozoan 11, mussel 12 (and from this point, mussel will refer to the three invasive species that most concern this invention, the *quagga* mussel, the zebra mussel, and the Mediterranean mussel), fungi 13, biofilm 14 (containing an organic protein matrix and bacteria), and barnacle 15. All of these organisms are seen attached to the left side exposed to water, labeled as water 2 in FIG. 1A, the water side of Polymer-O. Polymer-O 3 and polymer-I 9 are as in FIG. 1A and the protected surface 19 is shown. There is an outer polymer primer (Primer-O) 18 between Polymer-I and Polymer-O, and the Primer-O contains biostatic biocide 16 (5 on FIG. 1A) and biocidal biocide 17 (4 on FIG.

1A) in equal concentrations, although the ratio of the concentration of the biocidal biocide to the biostatic biocide in primer-O can range from 1:10 (similar to Polymer-O) to 10:1 (similar to Polymer-I). All biostatic biocides and all biocidal biocides may again be members of the classes of biocides defined in the disclosure and the tables of FIGS. 21A, B, and D and will hold true throughout all of the embodiments so described.

Figure 1C:
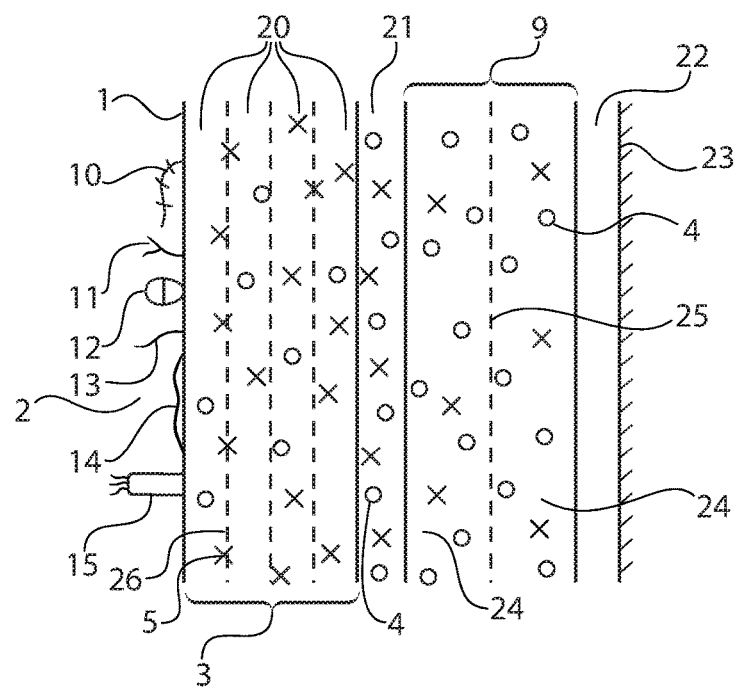
FIG. 1C depicts a cross section of an anti-fouling coating with an outer biostatic polymer layer and an inner biocidal polymer layer with an inner polymer primer beneath the inner biocidal polymer layer and an outer polymer primer between the biocidal inner polymer layer and the biostatic outer polymer layer.

Referring to FIG. 1C, a structural embodiment of the present invention is shown containing a four-layer structure: Polymer-O 3, now labeled with several constituent coatings 20 that were applied separately to build up the thickness of the polymer-O layer, Polymer-I 9 now with two separate coatings 24 that were used to build up the thickness of the polymer-I layer, a Primer-O 21, and a new inner polymer primer 22. Polymer-O 3, Polymer-I 9, and Primer-O 21 contain biocides as previously described for FIGS. 1A and 1B. The surface being protected is designated as 23. Coating boundaries 25 and 26 are shown between successive coatings making up Polymer-I 9 and Polymer-O 3 respectively. Biostatic biocide 4 and biocidal biocide 5 are as previously in the previously described concentrations. The biofouling organisms in the body of water 2 are again seen attached to the water surface 1 of Polymer-O. Coating interfaces 25 and 26 are only theoretically present if the coatings were added while the previous coatings were still tacky and semi-cured. The interfaces would disappear under these conditions and the separate coatings would fuse into one inseparable layer comprising the respective inner and outer polymer materials. However, if each coating is completely dry and cured at the time of the next coating, these interfaces would structurally remain.

In this manner, the Polymer-I and Polymer-O layers 3 and 9 can be built up in a layered or fused manner to be of arbitrary thickness, with a preferred thickness that ranges from about 5 mils to about 200 mils. Each incremental coating that builds up the polymer layer can be about 10 to about 20 mils, depending upon the viscosity and other physical characteristics of the polymer. Since a primer usually only requires an application of one layer, the thickness of the inner Primer-I coating 22 and the outer Primer-O 21 would be in accordance with the recommended thickness for the primer polymer being used. Note that, if surface 23 is part of a steel structure that is thicker than a sheet structure and more massive, the optimal primer for greatest durability of the Primer-I layer 22, and thus the entire anti-fouling coating, may be a zinc-rich primer having an inorganic zinc compound, such as zinc phosphate or zinc silicate or an a zinc enriched epoxy, the latter being an epoxy primer impregnated by weight up to 90% with zinc powder, or an inorganic aluminum compound. Zinc chromate may be specifically excluded from this embodiment because of its toxicity.

Figure 2A:
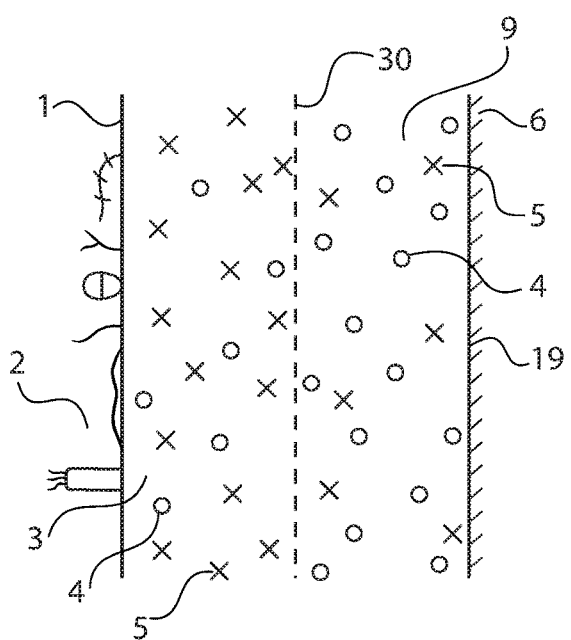
FIG. 2A depicts a cut-away view of an anti-fouling coating with an outer bio static polymer layer fused together with an inner biocidal polymer layer.

Referring to FIG. 2A, a structural embodiment of the anti-fouling coating is shown where the outer biostatic polymer layer 3 (Polymer-O) and the inner biocidal polymer layer 9 (Polymer-I) are fused together as one layer because polymer-O 3 was painted over Polymer-I 9 while the latter was still incompletely cured and was still tacky, in the same manner that several coatings may be used one after another before complete curing of the previous coating. 30 represents the fused interface between the biostatic-impregnated Polymer-O 3 and biocidal-impregnated Polymer-I 9. As described above, Polymer-O 3 has a relatively high concentration of biostatic biocide 5 and a relatively low concentration of biocidal biocide 4 while Polymer-I 9 has a relatively high concentration of biocidal biocide 4 and a relatively low concentration of biostatic biocide 5.

Figure 2B:
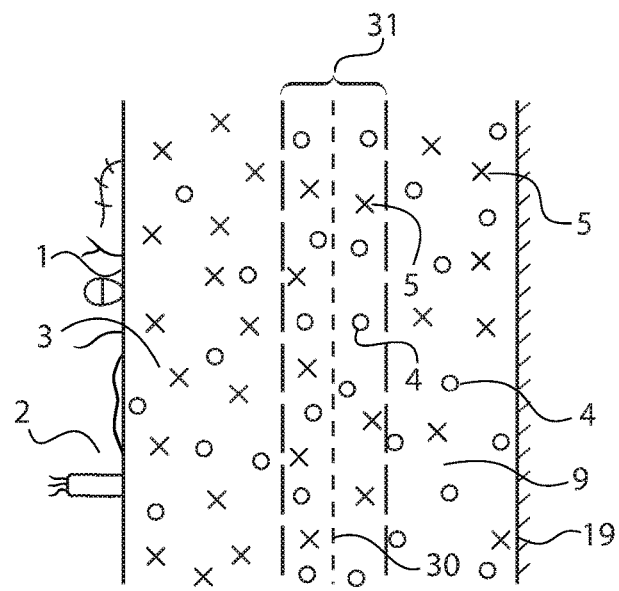
FIG. 2B depicts a cut-away view of an anti-fouling coating with an outer biostatic polymer layer fused together with an inner biocidal polymer layer with a composite fiberglass laminate.

Referring to FIG. 2B, a structural embodiment of the anti-fouling coating is shown where a perforated sheet 31 is inserted into the boundary between Polymer-O 3 and Polymer-I 9 that, together with the two coatings of polymer, makes up a polymer composite. The perforated sheet of material may be rigid, semi-rigid, or flexible. The perforated sheet or slab of material may be fiber-glass, another plastic, a fabric aramid fiber, a carbon fiber fabric, stainless steel or another metal, nylon, wood, ceramic, and so forth. While the Polymer-I layer 9 is still liquid and not cured, the perforated sheeting 31 is pushed into and immersed into Polymer-I 9. Polymer-I 9 is allowed to partially cure. While Polymer-I 9 is still tacky, liquid Polymer-O 3 is poured over the perforated sheeting 31, through which it flows up against partially cured Polymer-I. Both polymer layers are allowed to harden and cure, resulting in a fused interface 30 that runs through the perforated fiberglass sheeting whose inner half is immersed in Polymer-I 9 and outer half is immersed in Polymer-O 3.

Assembling this bi-laminate structure directly on the surface to be protected, with each layer of the bi-laminate structure containing two biocides whose concentration depends on the depth from the water surface of this structure, distinguishes this embodiment from the simple assembly of fiberglass composites. Note that the laminate coatings may be sprayed on, brushed on, poured, or attached to first the protected surface and then each other by any other suitable means, and may have polymer primers added to the process to separate Polymer-I 9 from Polymer-O 3 if the two polymer layers are sufficiently different that there is a need to increase the adhesion between the two layers, as will be shown in FIG. 2C as Primer-O 21.

If a polymer primer 21 is used between Polymer-O and Polymer-I, the perforated sheeting will either run through the polymer primer, or through Polymer-I 9, or through Polymer-O 3. In that case, the assembly process has an added step. Polymer-I 9 is laid down on surface 19. If the perforated sheeting 31 will run through Polymer-I 9, it is then pushed down into Polymer-I 9 while it is still liquid. If the perforated sheeting 31 will run through the polymer primer 21 instead, Polymer-I 9 is allowed to cure completely, and then the polymer primer 21 is laid down. While the latter is still liquid, the perforated sheeting 31 is pushed down into the primer 21, which is then cured, followed by laying down Polymer-O 3. If the perforated sheeting is to run through Polymer-O, then after the primer 21 is cured or nearly cured, Polymer-O is laid down and, while Polymer-O 3 still liquid, the perforated sheet 31 is pushed down into Polymer-O 3, which is then allowed to cure completely.

In the case of an outer polymer primer (Primer-O, structure 18 in FIG. 1B and structure 21 in FIG. 1C) being used between Polymer-O 3 and Polymer-I 9, where that primer may optionally have the same biocides impregnating it as the case for Polymer-I 9 and Polymer-O 3, that tri-laminate polymer structure will resemble the structural embodiment of FIG. 1B, only now with perforated sheet or slab 31 being added. Note that this assembly process can be further extended to include an inner polymer primer, Primer-I, structure 22 in FIG. 1C, to produce a four-layer polymer coating as demonstrated by the structural embodiment of FIG. 1C, but with the perforated sheeting or slab 31 being added to any one or more than one of the four layers, Polymer-O 3, Polymer-I 9, Primer-I 22, Primer-O 21 as seen on FIG. 1C.

Figure 2C:
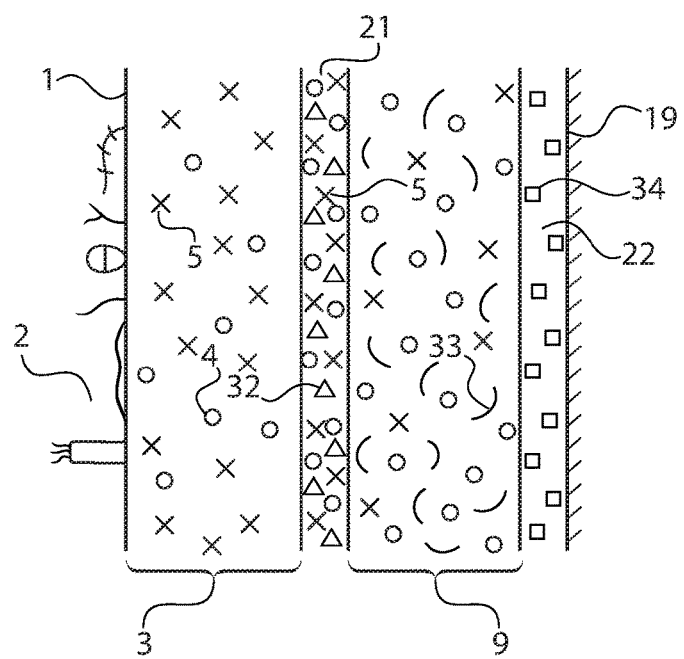
FIG. 2C depicts a cut-away view of an anti-fouling coating with an outer biostatic polymer layer containing biocides, an outer polymer primer containing structural additives and biocides, an inner biocidal polymer layer containing biocides and structural additives, and an inner polymer primer containing structural additives.

Referring to FIG. 2C, a structural embodiment of the antifouling coating of this invention shows a four-layer polymer coating as previously described in FIG. 1C, with Polymer-O 3 and Polymer-I 9 being comprised of the same biocides in the same relative concentrations as previous embodiments, but now Primer-O 21, used between Polymer-I and Polymer-O to promote the adhesion between the two layers as previously described in FIG. 1C, has biostatic biocide 5, biocidal biocide 4, and also a filler with small sharp microscopic fragments added to it. The concentrations of biocides 4 and 5 in Primer-I 22 may be of the concentrations specified for Polymer-O, Polymer-I, or any ratio of concentrations of the two biocides ranging between what was specified for Polymer-I 9 and Polymer-O 3. Therefore, Primer-I 22 can also be made either biostatic or biocidal with respect to the invasive biofouling species in aquatic environment 2. Primer-I 22 between the surface to be protected 19 and Polymer-I 9 is shown also to contain a filler with sharp microscopic fragments added and to contain the same biocides as in Polymer-O 3, Polymer-I 9, and Primer-O 21. Thus Primer-I 22 can also be made either biostatic or biocidal, but preferentially biocidal as, at that depth in the coating, the invasive organism must be killed or surface damage will occur. Biostatic biocides have little use in Primer-I 22 because, at that point in the antifouling coating depth, so close to the protected surface, the more potent biocide should be used. One category of metal alloys that are desirable for the purposes of this invention, cupro-nickel (and cupro-zinc, cupro-silver) should not be used in any polymer layer that is directly on a metal surface being protected because of the risk of galvanic action occurring between the biocide and a dissimilar metal in the protected surface, which would rapidly lead to corrosion and severe damage independent of the corrosion produced by fouling species. However, on non-metal hulls, cupro-nickel powder in sufficient amounts would make for an excellent biocidal biocide in the Primer-I 22. The use of a zinc-rich epoxy polymer primer as an inner polymer primer is biocidal in itself because of the high concentration of zinc powder present for primer adhesion. The use of a zinc-rich epoxy may allow the Primer-I 22 to function as a Polymer-I layer, a beneficial arrangement especially on metal surfaces exposed to high velocity and turbulence in water, such as ship propellers.

With regard to fillers, in FIG. 2C a first filler 32 is added to Primer-O 21, a second filler 34 is added to Primer-I 22, and a third filler 33 is added to Polymer-I 9. One purpose of fillers in a polymer layer or polymer primer, if used, is to promote adhesion between that layer and adjacent layers or the surface to be protected, to increase the wear and durability of that polymer layer and polymer primer, and to increase their hardness. An adhesion-promoting filler may be one of a group composed of a metal, such as stainless steel, copper, brass (where the percentage of metal fillers would not be high enough to constitute a biocidal agent such as when high concentrations of copper or zinc are used in anti-fouling paint), a mineral, such as fluorspar, silica (silicon dioxide), or industrial diamond powder, or a ceramic, such as boron carbide, cubic boron nitride, silicon and metal carbides, and others that share extremely high Mohs hardness levels of 9 or greater.

One specific filler that is contemplated herein is boron carbide (BC), B4C (with an alternate chemical structure of B12C3), the third hardest substance known, with a Mohs hardness rating of 9.3, next to cubic boron nitride (Mohs 9.5), and diamond (Mohs 10), and it is the preferred filler because of its low expense, easy availability in a wide range of mesh particle size, and its effect to improve the mechanical properties of the present embodiments. The particle size of the filler may range from about 7 microns to about 90 microns, depending upon the application, but certain uses may require nano-sized, sub-micron particles. The only restrictions on the use of fillers of this type are that they should not be used with the larger particle size in Polymer-O 3, as this would undesirably increase friction from water moving against the protected surface, and that fillers used in the polymer layer adjacent to the surface being protected (either Polymer-I 9 or Primer-I 22) should not be metallic when used on a protected surface that is metal, especially aluminum, to avoid unwanted and possibly severe galvanic action corrosion from dissimilar metals being in contact. Other classes of fillers, pigments and substances that might modify other physical characteristics of the polymers may be added as well for cosmetic reasons. To be discussed later will be the group of friction-reducing fillers that may be used in the Polymer-O layer 3 to decrease friction between the protected surface moving rapidly relative to the water.

Figure 3:
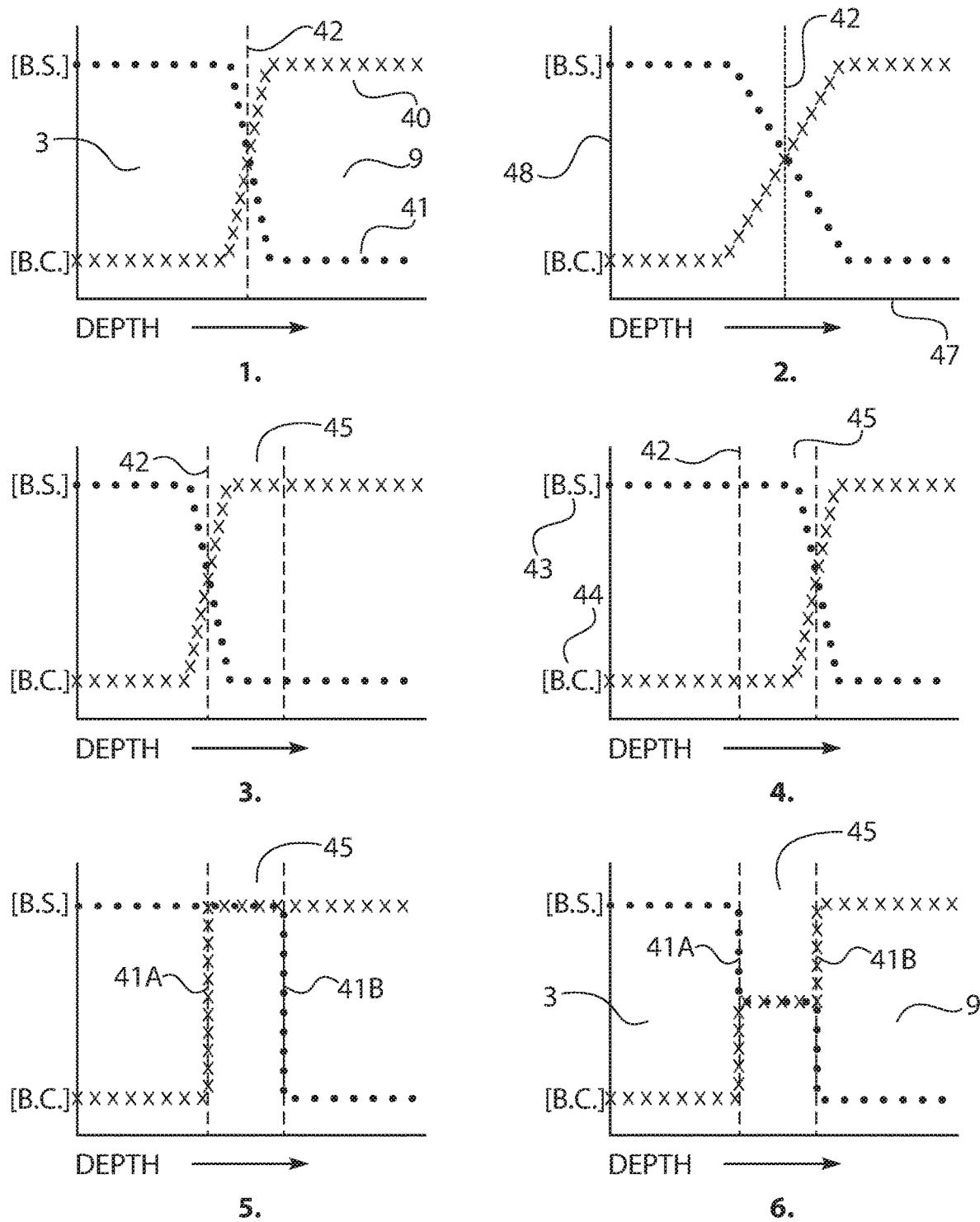
FIG. 3 illustrates graphs of the concentrations of biostatic biocide and biocidal biocide with depth into the anti-fouling coating with respect to the water surface for 6 different embodiments of coatings.

FIG. 3 displays graphs of the concentration of the biostatic biocide [B.S] with depth into the antifouling coating from the water surface of the coating and which is labeled here on these graphs as 41 and similarly for the concentration of the biocidal biocide [B.C] which is labeled here on these graphs as 40. Polymer-O is again designated as 3 and Polymer-I as 9 and are both labeled as such in FIG. 3(1) and FIG. 3(6). The vertical axis of biocide concentration is labeled as 48 on FIG. 3(2) and the horizontal axis of depth of location within the biofouling coating away from its water surface is labeled as 47 in FIG. 3(2).

FIG. 3(1) shows the biostatic biocide in relatively high concentration in Polymer-O 3, which diminishes quickly through the boundary region 42 between Polymer-O 3 and Polymer-I 9 to the relatively low concentration in Polymer-I 9. The concentration decreases over this natural boundary area due to diffusion of the biostatic biocide from a region of relatively high concentration to a region of low concentration. Similarly, the biocidal biocide in relatively low concentration in Polymer-O 3 increases quickly through the boundary region 42 to that of the relatively high concentration in Polymer-I 9.

The same situation holds for FIG. 3(2), only in this case Polymer-O 3 was laid down on Polymer-I 9 while the former was still tacky and only partly cured, so that the two polymer layers were fused together as one and the diffusion zone 42 for the biocides is significantly widened, because of the greater mobility of the biocide molecules.

FIG. 3(3) shows the biocide concentration gradients when a Primer-O 45 is introduced between Polymer-O 3 and Polymer-I 9, with Primer-O 45 bring impregnated with the biocides at the same concentration as is found in Polymer-I 9, essentially making Primer-O 45 biocidal to biofouling species in the same manner as is Polymer-I 9. The transition zone is moved shallower into the coating and toward the water surface of the anti-fouling coating.

Similarly FIG. 3(4) shows the biocide concentration gradients when a Primer-O 45 is introduced between Polymer-O 3 and Polymer-I 9 when Primer-O 45 is impregnated with the biocides at the same concentration as is found in Polymer-O 3, essentially making Primer-O 45 biostatic to biofouling species in the same manner as is Polymer-O 3. The transition zone is moved deeper into the anti-fouling coating away from the water surface.

FIG. 3(5) again shows the same situation as FIG. 3(3) and FIG. 3(4), except that this time Primer-O 45 has the same relatively high biostatic concentration as that of Polymer-O 3 and the same relatively high biocidal concentration as that of Polymer-I 9, which leads to two sharp transition zones, 41A and 41B, where at transition zone 41B the relatively high concentration of biostatic biocide in Polymer-O 3 abruptly decreases to the relatively low concentration of biostatic biocide in Polymer-I 9 and where, at transition zone 41A, the relatively low concentration of biocidal biocide in Polymer-O 3 abruptly increases to the relatively high concentration of biocidal biocide in Polymer-I 9. Abrupt transition zones can be widened if Polymer-O 3 is applied to Primer-O 45 while Primer-O 45 is still tacky and not fully cured, and also if Primer-O 45 is applied to Polymer-I 9 while Polymer-I 9 is still tacky and not fully cured.

Finally, FIG. 3(6) shows the same situation as FIG. 3(5), only now the concentration of the biostatic biocide in Primer-O is about 50% of that of the relatively high concentration in Polymer-O 3 and the biocidal biocide in Primer-I 9 is about 50% of the relatively high concentration in Polymer-I 9. Again, the sharp transition zones, 41A and 41B, can be widened through the mechanism just described for FIG. 3(5).

Figure 4:
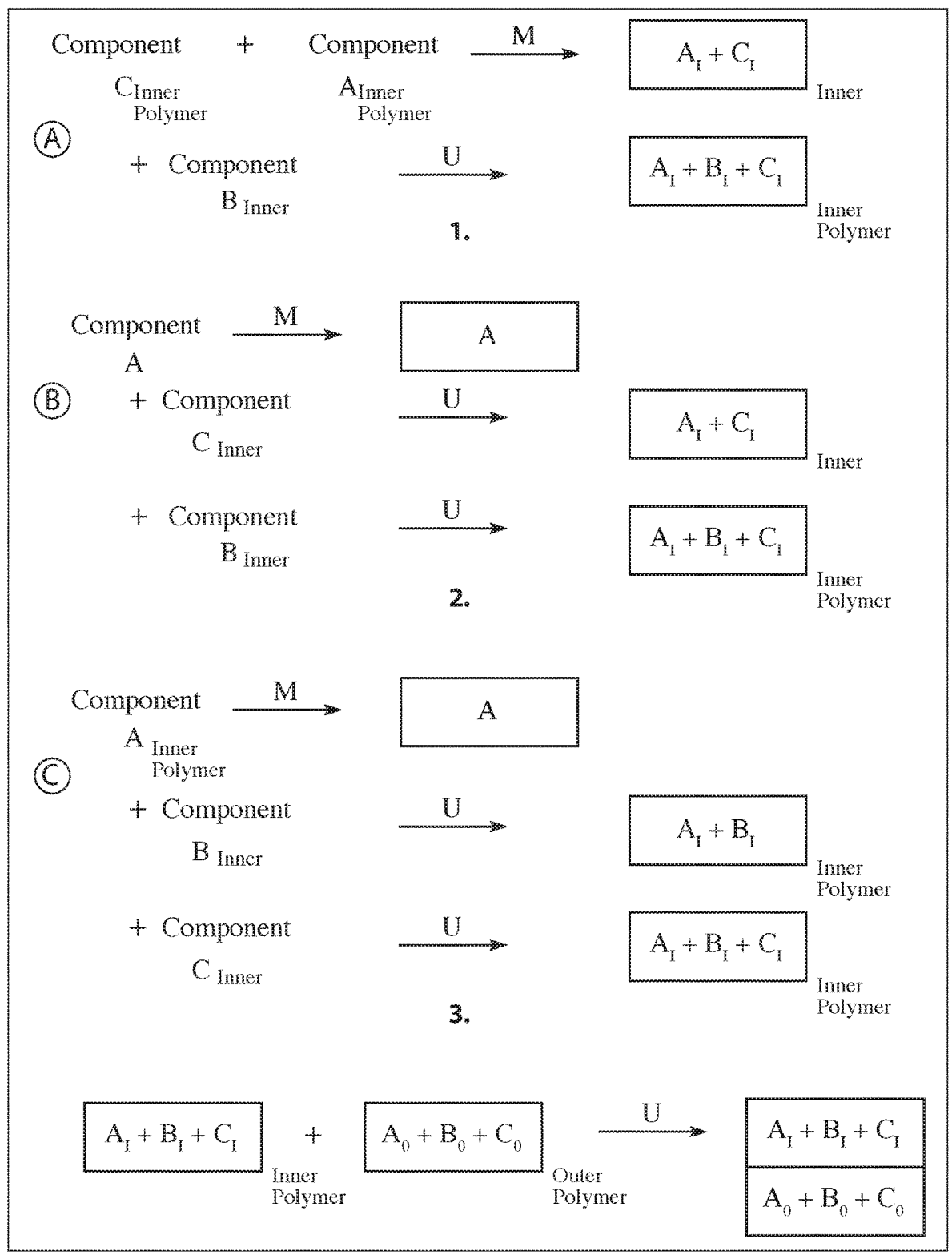
FIG. 4 illustrates three methods of re-constituting the inner polymer layer and the outer polymer layer (not shown) and the entire anti-fouling coating.
Figure 5A:
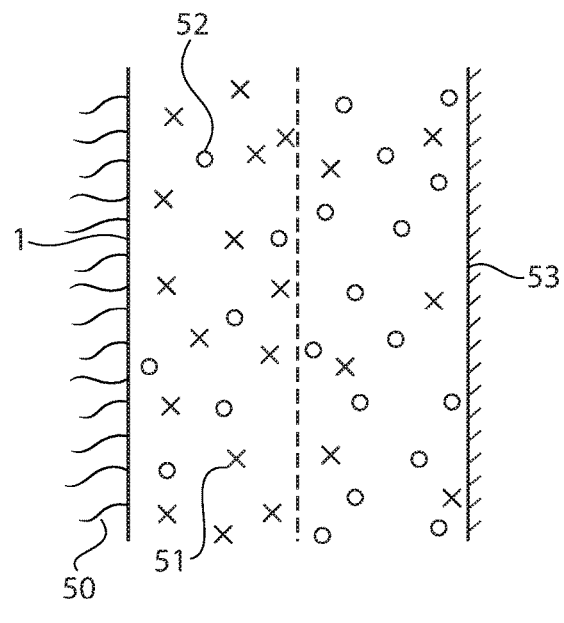
FIG. 5A depicts a cut-away view of biofouling larval forms being incompletely prevented from permanently attaching with a single biostatic biocide being present in the outer polymer layer.
Figure 5A:
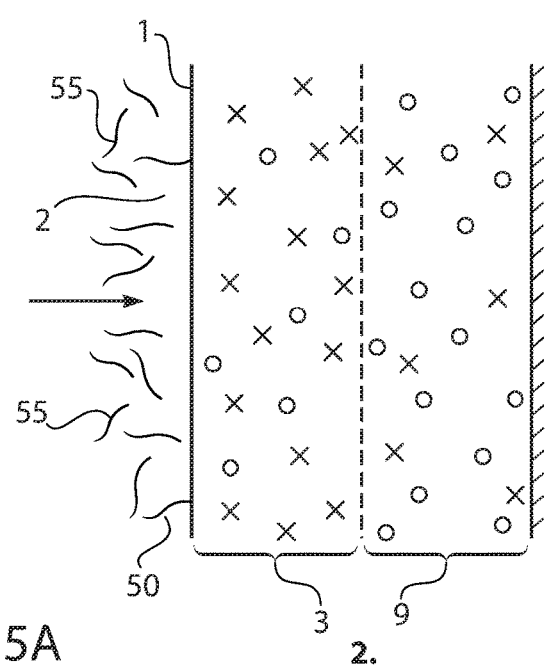
Figure 5B:
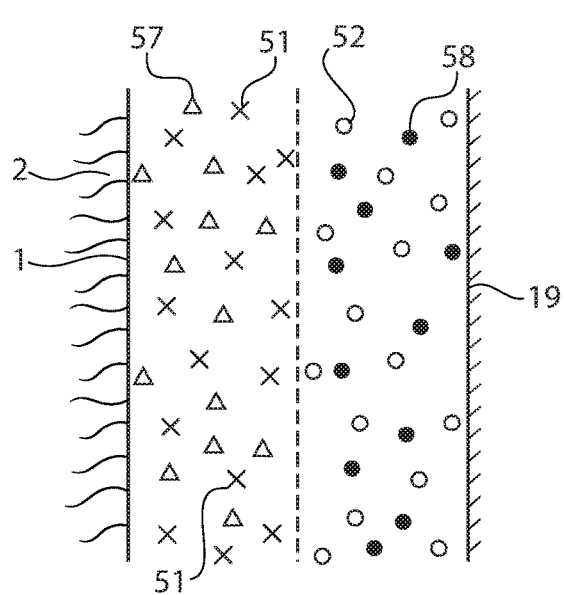
FIG. 5B depicts a cut-away view of biofouling larval forms being completely prevented from permanently attaching with two biostatic biocides being present in the outer polymer layer.
Figure 5B:
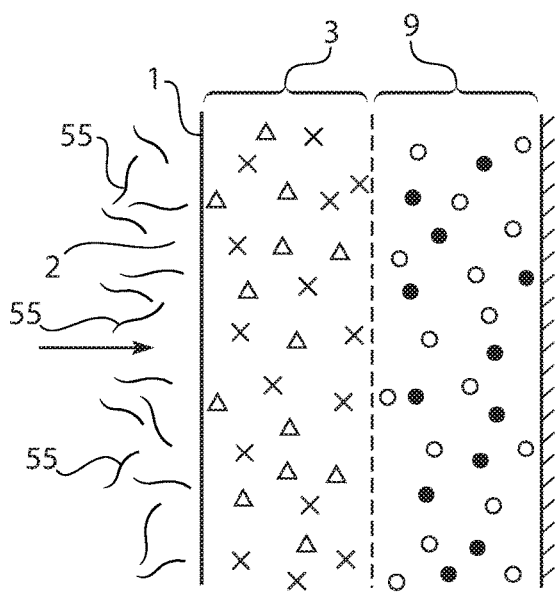

FIG. 4 shows a method of forming the biofouling coating described herein. U designates the user of the coating at the time of use and M designates the manufacturer manufacturing the coating. There are 3 manners of use by which the biocides are added to the polymer layers, one by the manufacturer at the time of manufacture, and two by the user at the time of use. Component A is defined as the carrier polymer, with or without added fillers, pigments, and other particles, component B is defined as the curing agent or hardener that effects a curing or hardening process on the carrier polymer, and component C is the biocide component composed of the biostatic and biocidal biocides to be added and the polymer carrier component A. Isopropyl alcohol, benzyl alcohol, methyl-ethyl-ketone (MEK) and other organic solvents may be added to either component A or component C if the polymer carrier and biocides are compatible with the solvent to help decrease the viscosity of the biofouling coating so that the components A, B, and C can be mixed together more easily.

FIG. 4 also indicates that Polymer-O 3 and Polymer-I 9 may each be formed as per FIG. 4, only the formation of Polymer-I 9 is described in detail. The same procedure would be done for Polymer-O 3. Component C is a mixture or solution of biocidal polymer and biostatic polymer comprising about 0.1%-about 50% by weight of component C, and about 50% to about 99.9% by weight of component C would be the carrier polymer (component A) itself.

Process 1 calls for the addition by the manufacturer of Component $C_{inner\ polymer}$ to be added to Component $A_{inner\ polymer}$ at the time of manufacturer to produce a mixture, $(A_I+C_I)$, that is shipped by the manufacturer, M, to user U along with hardener Component B unter polymer. At the time of use, user U mixes hardener Component B unter polymer together with mixture $(A_I+C_I)$ to give the final inner polymer biocidal coating, Polymer-I 9, whose components are designated as mixture $(A_I+B_I+C_I)$. This coating is then applied to the surface to be protected (or to the inner polymer primer, Primer-I, if used) to form the inner biocidal coating, Polymer-I. Likewise, the same procedure is followed for the outer biostatic polymer coating, Polymer-O. Though not shown in FIG. 4, the formation process may be exactly the same, where the manufacturer M adds biocide Component $C_{outer\ polymer}$ at the time of manufacture to the carrier polymer Component A, $A_{outer\ polymer}$, to produce a mixture, $(A_O+C_O)$, which is then shipped to user U along with hardener Component $B_{outer\ polymer}$. At the time of use, user U mixes hardener component $B_{outer\ polymer}$ with the mixture $(A_O+C_O)$ to give the final outer polymer biocidal coating, Polymer-O, whose components are designated as mixture $(A_O+B_O+C=)$. This coating is then applied to the inner biocidal layer, Polymer-I (or an outer polymer primer if used) to give the outer biostatic polymer coating, Polymer-O. The same process would be applied to Primer-I and Primer-O if used and if both contain biocides. If they are used but they do not contain biocides, there would be no C component for the primers, and Component A (polymer primer carrier) and Component B would be sent to user U by manufacturer M as is customary for use by user U at the time of application. Because the formation process is identical for polymer primers containing biocides, a detailed description of the formation process for these coatings will be omitted.

Continuing to refer to FIG. 4, process number 2 for the reconstitution of the biofouling coating is shown for the Polymer-I layer, with a similar procedure for Polymer-O, Primer-I, and Primer-O, if the primers are used and contain biocides. Manufacturer M does not add biocide Component $C_{inner\ primer}$ at the time of manufacture as in process number 1. Instead, the manufacturer M sends to user U three separate components, the carrier primer, $A_{inner\ primer}$, the hardening agent for the carrier polymer, $B_{inner\ polymer}$, and the biocide containing Component $C_{inner\ polymer}$, who will reconstitute the polymer coating at the time of use.

At the time of use, user U mixes polymer carrier Component $A_{inner\ polymer}$ with the biocide containing Component $C_{inner\ polymer}$ producing mixture $(A_I+C_I)$, to which hardening or curing agent Component $B_{inner\ polymer}$ is added to produce the final mixture $(A_i+B_i+C_i)$ which is Polymer-I as in process 1. A similar process would be used for Polymer-O, and if they are used and contain biocides, Primer-I and Primer-O.

Process number 3 for the reconstitution of the biofouling coating is again shown for the Polymer-I coating. Manufacturer M again does not add the biocide component $C_{inner\ primer}$ at the time of manufacture. Instead, again Manufacturer M sends to user U all three components of the biofouling coating, carrier polymer Component $A_{inner\ polymer}$, hardening agent component $B_{inner\ polymer}$, and biocide containing component $C_{inner\ polymer}$. At the time of use, user U mixes hardening agent Component $B_{inner\ polymer}$ with Component $A_{inner\ polymer}$ to make mixture $(A_i+B_i)$, and to this mixture, biocide containing component $C_{inner\ polymer}$ is added just prior to application to a protected surface, again yielding mixture $(A_i+B_i+C_i)$, which is now used to coat the protected surface. A similar such process 3 would be used for Polymer-O, and if they are used and contain biocides, Primer-I and Primer-O.

At no time is the hardening agent Component B in concentrated form ever in contact with the biocide containing Component C, a situation which otherwise might cause the biocides in component C to come into contact with the highly reactive Component B hardener, as this can possible impact unfavorably affect the final curing, mechanical, chemical, or optical qualities of the polymer layer or might affect the biocides themselves, thus changing their biocidal characteristics. The only time Component C comes into direct contact with Component B is when in Process number 3, after Component B is mixed with Component A at the time of use. When Component C is next added to the mixture of Component A and Component B, Component C is only exposed to a very dilute concentration of hardener Component B, which has been heavily diluted with careful mixing with Component A. Careful and extensive mixing is used to prevent any chance of component C from coming into contact with concentrated component B. Any fillers to be used with any of the polymer layers used in the biofouling coating would be added to the polymer carrier at the time of manufacture, although the fillers could be sent separately and added to the mixture by the user U at the time of use.

Each polymer layer—Polymer-O, Polymer-I, and if used, Primer-O and Primer-I, would have its own kit and such separate kits would be shipped to the User U by manufacturer M. Each biocide Component C for each polymer layer in the final multi-layer biofouling coating would be uniquely different and matched to that particular desired polymer layer. Manufacturer M would either formulate its own biocide containing Component C for use with a particular polymer coating (Component A) and its hardening (or curing) agent (Component B) and the three Components A, B, and C would be sent out to the user U, unless components A, and C are pre-mixed together at the time of manufacture (Process number 1, where component B and mixture ($A_i$+$B_i$) would be sent out to user U). Manufacturer M can also arrange to have pre-mixed Component C kits manufactured by a third party who would ship it to Manufacturer M for inclusion into its polymer coating kits.

The biocide-containing Component C used with a specific polymer for a specific application would be unique for that specific polymer and its hardener to guarantee that the biocides and the hardener would not chemically interfere with each other and that the biocides used were consistent with the application being involved in preventing biofouling by invertebrate calcium forming organisms as well as the carrier polymer being consistent with the needs of the application under consideration.

The inclusion of a suitable algaecide can be formulated in Component C as well and added to the invertebrate biocides to give the outside biostatic polymer layer, Polymer-O, algaecide capabilities as well. Such chemical compounds can be chosen from the table of herbicides listed in FIG. 21C and may be added to Component C in the same manner of and in the same percentages of weight composition of that of the invertebrate biocides.

FIGS. 5A and 5B demonstrate the polypharmaceutical process of biofouling organism cell kill. In FIG. 5A, a cut-away view of the biofouling coating is shown including a biostatic biocide 51 in relatively high concentration and a biocidal biocide 52 in relatively low concentration making up Polymer-O 3 and a biocidal biocide 52 in relatively high concentration and a biostatic biocide 51 in relatively low concentration impregnating Polymer-I 9. Barnacle cyprid larval forms 50 from aquatic environment 2 (labeled in FIG. 3B) are shown having attached themselves to the water surface 1. The cut-away view on the left, FIG. 5A(1) illustrates barnacle cyprids trying to attach themselves to the water surface 1. Because of the presence of a relatively high concentration of biostatic biocide 51, such as capsaicin, helped by a relatively low concentration of biocidal biocide 52, the vast majority (in this example, all but two) are shown as having detached themselves from that surface in FIG. 5A(2). Detached cyprids are designated as 55 and they will swim off to either try to find a more hospitable surface to settle on or, more likely, they will eventually die.

However, in this example, two cyprids 50 are apparently resistant for whatever reason to the biostatic biocide and remain attached to the water surface 1 of the coating. They continue to grow and mature into juvenile barnacles, with this process taking about 6 to about 24 hours. The cyprids 50 will then begin to burrow into Polymer-O of the coating, potentially causing damage to the surface 53 being protected.

However, because of the presence of the relatively high concentration of biocidal biocide 52, such as ivermectin, helped by the presence of a low concentration of biostatic capsaicin, the two biocides will together kill the juvenile barnacle, now about 0.1 mm in diameter, before it will ever reach the surface 53.

However, FIG. 5B demonstrates an even more effective way of producing an increased organism kill. The same structural coating is shown as in FIG. 5A, but the composition has changed so that there are now two biostatic biocides, both of which are in relatively high concentrations. In this example, the first biostatic biocide 51 (e.g., capsaicin) is used, plus either a low dose second biostatic biocide 58 (e.g., pyrethrin or pyrethroid-type of insecticide or cupronickel powder) in relatively high concentration. The relatively high concentration of the second biostatic biocide replaces the need for a relatively low concentration of the biocidal biocide. Because of the marked synergistic effect of these two potent biofouling inhibitors, now no barnacle cyprids 50 remain attached and all barnacles now are free floating (labeled 55). Polymer-O 3 is now totally free of barnacles as shown in FIG. 5B(2).

This result is due to parallel action of the two biostatic biocides. Also, Polymer-I may be impregnated with a second biocidal biocide. For example, in addition to the ivermectin, one can use Lufenuron or high concentrations of a pyrethrin or pyrethroid type of biocide together with piperonyl butoxide, which prevents metabolism of the pyrethrin compound. Together, with the Lufenuron acting as a chitin synthetase enzyme inhibitor, or a high level pyrethrin impregnation inhibiting the barnacles GABA receptor acting in conjunction with the ivermectin hyperpolarization of the cyprid's nervous system, a synergistic effect is produced.

It is important to note that these chosen biocides are not impregnated into the polymer layers as a random composition. Rather, combinations of cellular metabolic and physiological processes are selected that can be interfered with or blocked, producing the most effective biostatic or biocidal effect. The present embodiments thereby achieves "synergistic" inhibition and lethality, where the biocide combination's inhibitory effects, killing effects, or both exceed the effects of each separate drug alone, and "synthetic" inhibition and lethality, when a first cellular mechanism is blocked by a first biocide, but a second cellular mechanism is available to bypass the blocked first cellular mechanism. However the organism is nonetheless inhibited or killed effectively because of the presence of a second biocide, which blocks the second cellular mechanism.

Referring to FIG. 6A, a cut-away view of an embodiment of the anti-fouling coating is shown, enhanced to provide control of algae infestations on submerged surfaces in addition to controlling of invertebrate calcium-forming infestations. FIG. 6A(1) shows the basic two-polymer layer of the biofouling coating as shown previously. Note that or the biofouling coating in FIG. 6A(1) is effective against animal biofouling organisms and not effective against plant biofouling organisms. Thus organisms bryozoans 61, invasive mussels 62, shipworms (marine woodborers) 63, and barnacles 65 are shown detached from the water surface of the coating 1 and are floating in aquatic environment 2. They are successfully repelled by the biostatic effect of Polymer-O 3. The organisms further include algae 60, fungi 66, and biofilm 64 adherent to the water surface 1, providing a means for the larval forms of invertebrate animals to settle on the surface without actually touching it initially. This is not desirable because the biofilm shields the larval form from the Polymer-O layer 3 as well as causes undesirable cosmetic effects.

Figure 6A:
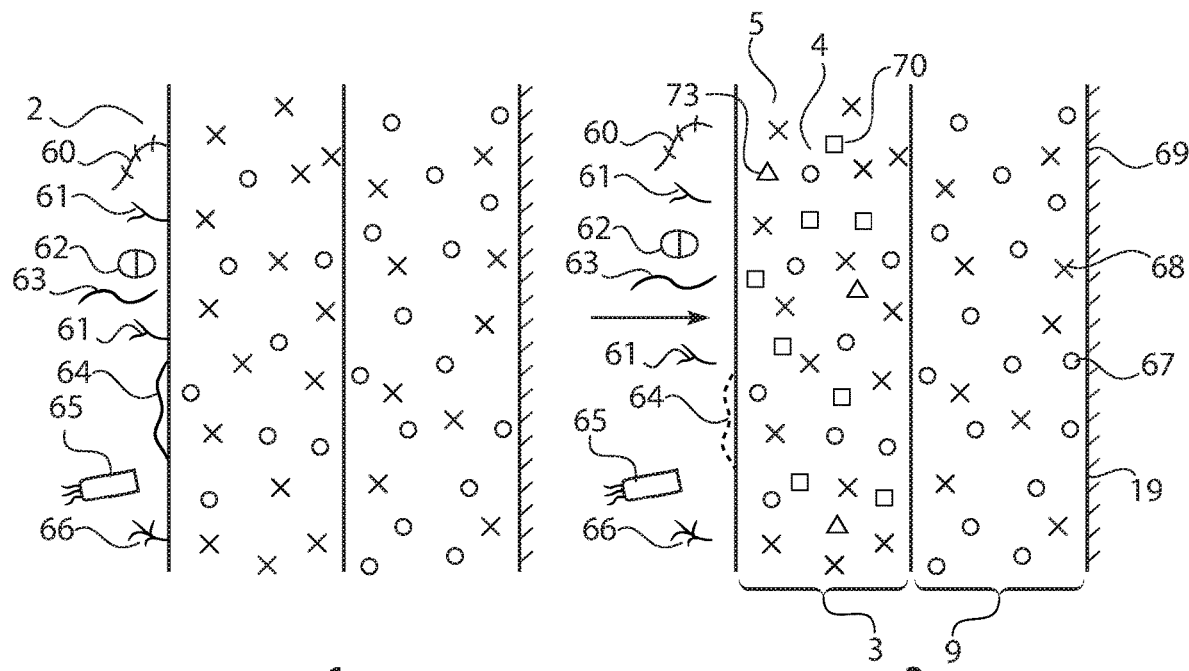
FIG. 6A depicts cut-away views showing additional inhibition of attachment of 3 classes of invasive plant biofouling species with an algaecide added to the outer biostatic polymer coating containing a biostatic biocide in high concentration, and a biocidal biocide in low concentration.

By adding an algaecide 70 to Polymer-O 3 of FIG. 6A(2), especially a broadly phytotoxic algaecide with activity against all three categories of plants, algae, fungi, and bacteria, all the organisms, both plant and animal, are no longer attached, and the biofilm has disintegrated. One exemplary algaecide that may be used is a metal pyrithione salt such as zinc pyrithione, but any metal salt of pyrithione or mixture of such metal salts will do, including for example copper, barium, silver, strontium and so forth. Pyrithione compounds have broad spectrum phytotoxicity against all three categories of plants and an exceptional safety profile for animals and humans. Furthermore, any low water solubility herbicide listed the table of FIG. 21C will be appropriate for use as an algaecide as well.

Figure 6B:
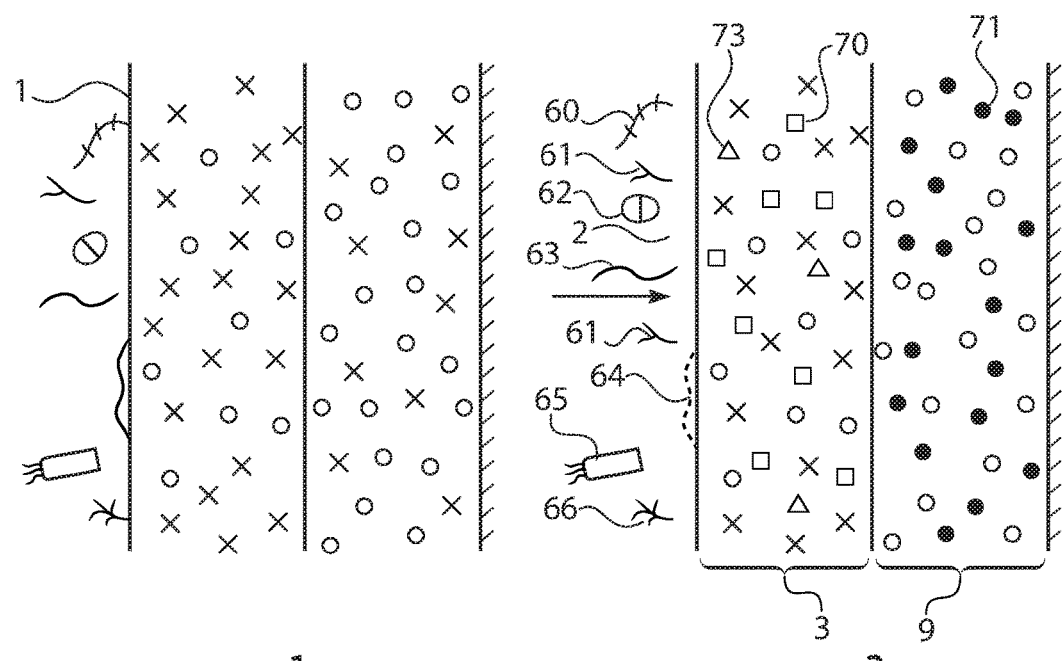
FIG. 6B depicts cut-away views showing additional inhibition of attachment of 3 classes of invasive plant biofouling species with an algaecide added to the outer biostatic polymer coating containing two biostatic biocides at high concentration.

Referring to FIG. 6B(2), a cut-away view is shown of an embodiment of the anti-fouling coating of FIG. 6B(1), enhanced by the use of not only the algaecide 70, but also a second biostatic biocide 73 in Polymer-O and a second biocidal biocide 71 in Polymer-I. As a result of the enhancements of the addition of algaecide 70 and the additional biostatic biocide 73 in Polymer-O 3, all organisms, including plant organisms, are inhibited from attaching. The chance of any invertebrate biofouling organism being resistant to the Polymer-O layer 3, and the two biostatic biocides that are now in the Polymer-O layer 3, is much reduced. If there is a particularly hardy organism that can attach in spite of such a broad spectrum of biostatic coverage, and it attempts to pierce and grow through Polymer-O 3 and grow through the boundary between Polymer-O 3 and Polymer-I 9, it will be killed by the more potent biocidal nature of Polymer-I 9 enhanced with an additional biocidal biocide 71 while it is still a microscopic juvenile form. The pits on Polymer-I's boundary left by the dead invertebrate animal will be so tiny that the leakage of the more potent biocides of the Polymer-I 9 layer will be essentially non-existent, with that latter layer still being completely shielded from the aquatic environment 2 by Polymer-O 3.

Figure 7:
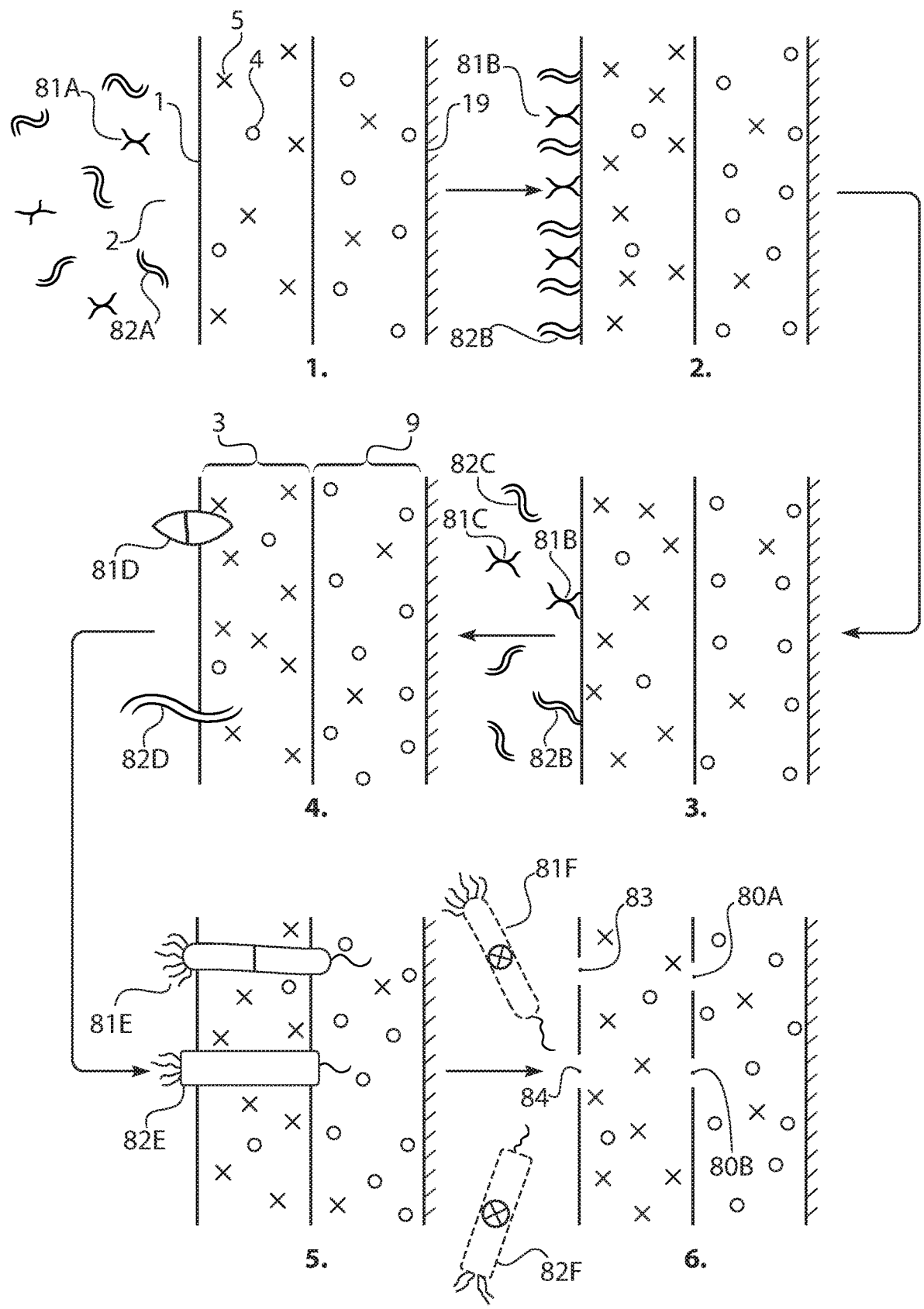
FIG. 7 depicts the sequential process of biofouling control with first, cyprid larval barnacle attachment or veliger larval mussel attachment inhibition and then second, death of juvenile barnacle or mussel organism.

FIG. 7 depicts a series of 6 sequential cut-away views of the antifouling coating that illustrate the sequential toxicity that the present embodiments deliver to diverse biofouling organisms. Again present are biostatic biocide 5 and biocidal biocide 4. FIG. 7(1) depicts anti-fouling coating comprised of Polymer-O 3 and Polymer-I 9 (labelled in FIG. 7(4)) being attacked simultaneously by mussel larvae (veligers) 82A and barnacle larvae (cyprids) 81A swimming freely in aquatic environment 2 looking to attach to water surface 1 of the anti-fouling coating protected submerged surface 19. This example is for illustration only, as in practice fresh water invasive mussels, *quagga*, and zebra mussels would not be in the same body of water as saltwater invasive barnacles. Initial attachment of multiple cyprids 81B and multiple veligers 82B are shown in FIG. 7(2). FIG. 7(3) shows that most of the veligers 81C and cyprids 82C are repelled and float away into the aquatic environment as a result of the biostatic effects of contact with Polymer-O 3.

However, one veliger 81B and one cyprid 82B are resistant to the biostatic nature of Polymer-O 3. Over a 6 to 24 hour period after implantation, cyprids and veligers start and complete their metamorphosis and maturation to a juvenile form and they grow slightly larger, changing form as represented by 81D juvenile mussel and by 82D juvenile barnacle in FIG. 7(4). In FIG. 7(5) further growth of juvenile mussel 81E and juvenile barnacle 82E is shown, now piercing Polymer-O 3 completely and piercing the boundary between Polymer-O 3 and Polymer-I 9.

As soon as juvenile mussel 81E and juvenile barnacle 82E come in contact with Polymer-I 9 and its relatively high concentration of biocidal biocide 4, enhanced by its relatively low concentration of biostatic biocide 5, they are killed and float away dead as a dead juvenile mussel 81F and a dead juvenile barnacle 82F. At the time that Polymer-I 9 kills these juvenile forms, they are only 0.1 mm (100 microns), so they are essentially still microscopic. As a result the microscopic ringed defects left by their sharp-ringed immature cells leave tiny circular microscopic pits on the water-surface of Polymer-O 3. These pits are of no consequence because of their small size and the fact that they are so small in number.

Furthermore, tiny circular microscopic pits are left for the same reason on the surface of Polymer-I 9, but do not extend through the thickness of Polymer-I 9. This has two important consequences. First, Polymer-I 9 is never pierced to allow damage to be done to protected surface 19. Second, the surface defects are so small that there is no significant leakage or chemical leaching out of Polymer-I 9 into the surrounding water 2. Because Polymer-O 3 is still intact, resulting from the number of the defects in that polymer layer being so small and few in number, Polymer-O 3 continues to provide complete shielding from exposure to the aquatic environment to Polymer-I 9. That is the reason why even such a toxic biocidal agent like TBT can be used safely.

Figure 8:
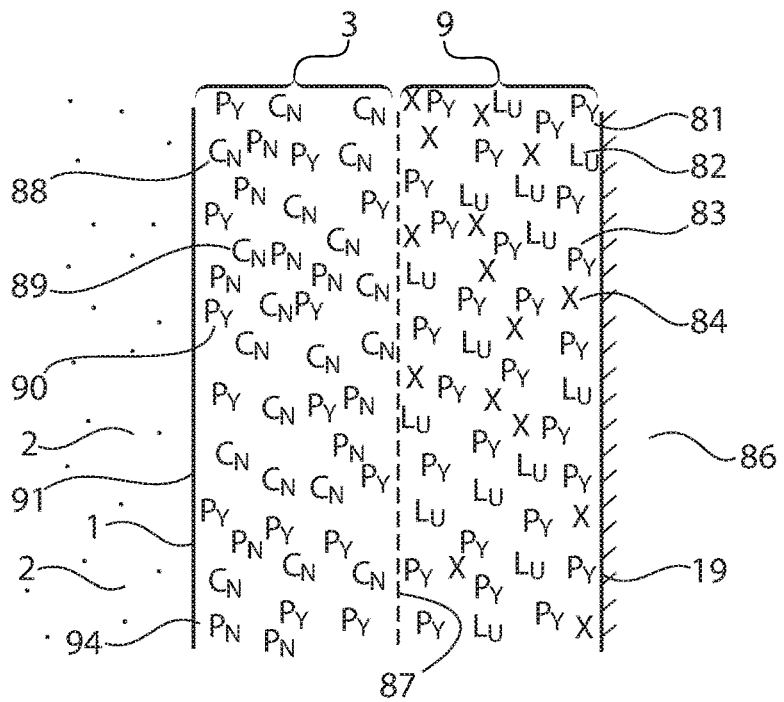
FIG. 8 depicts a cut-away view showing two biostatic biocides in the outer biostatic polymer layer (cupro-nickel alloy and low concentration pyrethrin) and two biocidal biocides in the inner biocidal polymer layer (Lufenuron and high concentration pyrethrin with piperonyl butoxide)

FIG. 8 shows an embodiment of the antifouling coating with a wide spectrum of activity. Depicting a cut-away view of the coating, Polymer-O 3 and Polymer-I 9 are present. In this example, Polymer-O 3 contains, e.g., biostatic biocide cupro-nickel (CN) 89 and biostatic biocide low-dose pyrethrin compound (Py) 90, and Polymer-I 9 contains, e.g., biocidal biocide high dose pyrethrin compound 81 with piperonyl butoxide (x) 84, which is not itself a biocide but which enhances the lethality of high dose pyrethrins and pyrethroids, and biocidal biocide, Lufenuron (LU) 82. All of these biocides have activity against invertebrate calcium-forming biofoulers using different mechanisms of action as previously described.

In addition, Polymer-O 3 contains the algaecide, pyrithione as a metallic salt (PN) 94 to control algae, fungus, and bacterial proliferation as biofilm and bioslime. The aquatic environment 2, the water surface 1 of the antifouling coating, the surface 19 being protected, the interior 86 of the surface 19 being protected, and the boundary 87 between Polymer-O 3 and Polymer-I 9, are also shown.

The mechanism of actions of these biocides include: pyrithione—disrupting cellular membrane transport blockage of the proton pump that energizes cellular transport mechanisms which, in turn, results from a pyrithione-induced increased uptake from the environment of copper increasing, intracellular copper to toxic levels; pyrethrins and pyrethroids—GABAa receptor modulator and inhibitor; lufenuron—chitin synthetase enzyme inhibitor; cupro-nickel—GABAa receptor modulator and inhibitor, piperonyl butoxide—CYP 450 cytochrome inhibitor preventing metabolism of the pyrethrin compound.

Sequentially, the plant invasive species encounter a pyrithione metal salt (PN) 94 in Polymer-O which inhibits biofilm formation and algae from attaching, while the animal invasive species encounter both the biostatic biocides of a low dose pyrethrin compound (without piperonyl butoxide) (PY) 90 and cupro-nickel powder in low concentration (CN) 89, which synergistically will inhibit attachment of larval forms to the water surface 1 of the antifouling coating, preventing the invertebrate larvae from attaching. Then, if any invertebrate species make it through the Polymer-O layer 3 (algae will never penetrate it unless the way is led by a calcareous invasive organism), they will be destroyed by the synergistic lethality effect of combined high dose pyrethrin compound (PY) 83 together with the piperonyl butoxide (x) 84 and lufenuron (LU) 82.

There would be very little chance of significant numbers of invasive invertebrate biofouling organisms making it through both Polymer-O 3 and Polymer-I 9 layers to cause any bio-corrosive damage to the surface being protected 19. There would also be very little chance that the two biocide impregnated Polymer-I layer 9 would suffer any significant damage. Finally, there would be very little chance that Polymer-I 9 would be compromised sufficiently to allow any of the more potent biocidal biocides to leach into the aquatic environment 2.

Figure 9:
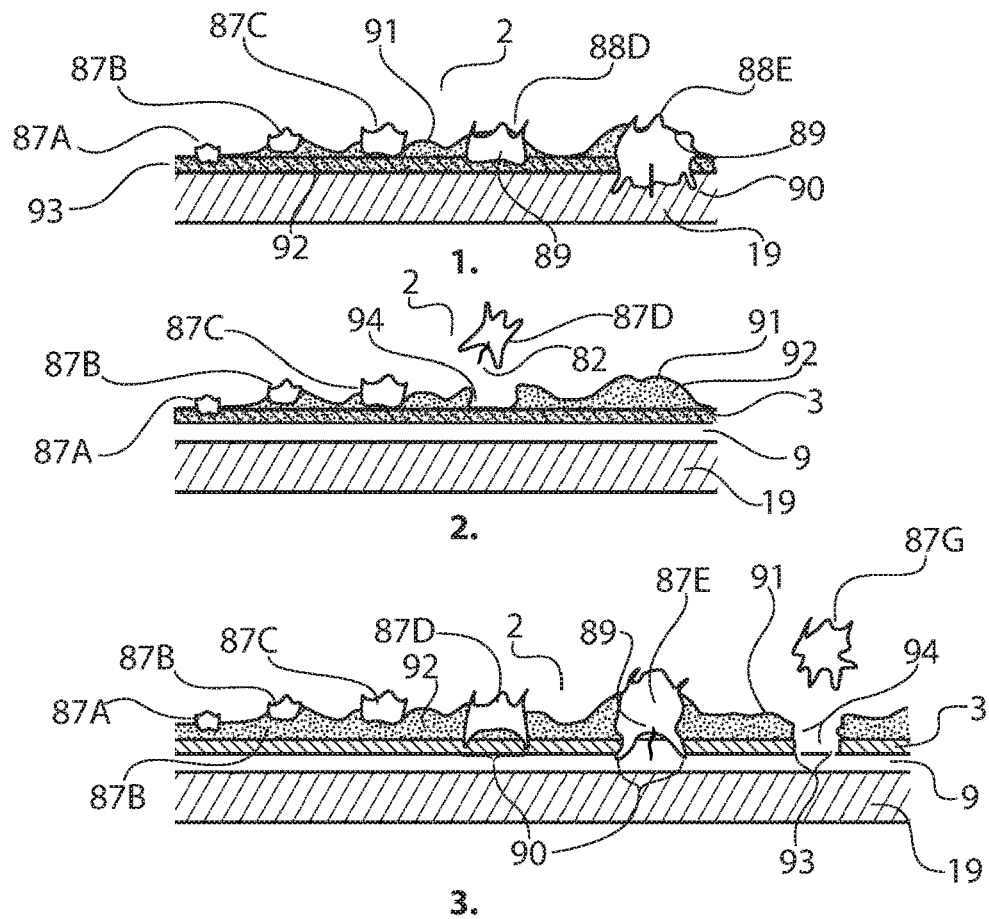
FIG. 9 depicts the erosive damaging bio-corrosion caused by hard calcareous biofouling organisms including mussels and barnacles.

FIG. 9 depicts a series of three cut-away side views showing the inhibition of attachment and subsequent progressive penetration of the biofouling coating and the effects of such penetration on the integrity of the coating. Referring to FIG. 9(1), which depicts the penetration by a young barnacle of a coating, such as ordinary marine paint, and its underlying surface when the biofouling coating of this invention is not in place and the coating has no other invasive biofouling control mechanism in place. A similar situation occurs with a developing young invasive mussel attacks the same type of coating. A generic protective coating 93 is shown that does not inhibit invasive species invasion by any other type of antifouling compound in the coating. The aquatic surface 91 of a biofilm or bioslime deposit on coating 93 and the interior 92 of that biofilm are also shown.

A barnacle cyprid 87A is shown having just settled down and attached itself to the biofilm (87B) and continues to grow and penetrate the biofilm (87C), finally invading the coating 93. By this time (6 to 24 hours after the initial settlement and attachment), the cyprid has changed to juvenile barnacle (87C). The juvenile form now invades coating 93, going through and attaching itself to the underlying protected substrate 19 by a structure known as a byssel thread 89 that also has extremely tough and very adhesive glue. This tough and very adhesive glue can induce corrosion in metals.

Next, the juvenile barnacle 88E penetrates deeper, developing an extremely sharp and ringed shell 90 that allows penetration through the coating 93, and begins to destroy the protected surface itself. From that point the organism's invasion is complete and the barnacle will be firmly implanted irrevocably within the coating. Bio-corrosion will set in, destroying or at least interfering with the function of the protected surface. At this point, the barnacle will stop growing in, and instead grow outward and in diameter, with the surface defect ranging from about ¼" in diameter to as much as 3" in diameter, depending upon the barnacle species. A similar such growth diagram could be constructed with veliger larvae belonging to invasive mussels.

FIG. 9(2) shows the growth process for a barnacle when a biofouling coating according to one of the present embodiments. Surface 19 this time is covered by a bilaminar coating that includes biocidal inner polymer layer Polymer-I 9 that covers surface 19. In turn, biostatic outer polymer layer Polymer-O 3 covers Polymer-I 9 and shields that inner polymer layer from any contact with the aquatic environment 2. Now cyprid 87A alights on biofilm surface 91 from aquatic environment 2. It evolves into cyprid 87B, penetrating the surface 91 of the biofilm into the interior 92 of the biofilm. Further growth as a transforming cyprid into a juvenile form 87C begins to proceed and now the cyprid pierces the biofilm and invades the biostatic Polymer-O layer with its early developing shell 90. At this point, contact with the biocides in Polymer-O 3 activates its vanillin receptors secondary to the capsaicin and its GABAa receptors are inhibited by a pyrethrin compound if these are the two biocides used. The cyprid (87D) pulls away from the water surface 1 (Labeled in FIG. 8) of Polymer-O 3 and floats away to either attach at some other location or else die. Virtually no damage results, even on a microscopic scale, and Polymer-O 3 remains completely intact. Polymer-I 9 just underneath sustains no damage.

FIG. 9(3) shows the growth process for a barnacle on the rare occasion when a barnacle cyprid manages to attach and continues to develop into a juvenile form. As before, cyprid 87A attaches to the surface 91 of the biofilm, progresses into cyprid 87B growing now in the interior 92 of the biofilm, becoming deeply embedded into the biofilm as cyprid 87C, and finally penetrating the biofilm layer as cyprid 87D and growing into biostatic Polymer-O 3 with a developing sharp ring shell 90 and byssel attachment thread 89. In this example, the cyprid 87D resists the biostatic biocidal effect of the Polymer-O layer 3, growing into juvenile barnacle form 87E which pierces through the entire thickness of Polymer-O 3. Its sharp shell reaches through the boundary of Polymer-O 3 and Polymer-I 9 to invade the biocidal Polymer-I 9 with its shell.

As soon as the juvenile cyprid 87E reaches the Polymer-I layer, however, it encounters the lethal biocidal biocide or biocides and it is killed. The dead juvenile form 87G, still only about 0.1 mm in diameter (100 microns), releases its grip from the antifouling coating and floats away. A small defect 94 of about 0.1 mm in diameter remains in the biofilm 92 and Polymer-O 3, and an even smaller ringed defect 93 is present in the top surface of Polymer-I 9. The defect in the biofilm is quickly covered, the ringed defect 94 in Polymer-O is too small and too rare to be of any consequence, and the even smaller defect 93 in Polymer-I is also of no consequence. The more potent biocidal biocide or biocides in the Polymer-I layer 9 are still shielded from the aquatic environment 2. The surface to be protected remains completely unharmed.

Figure 10A:
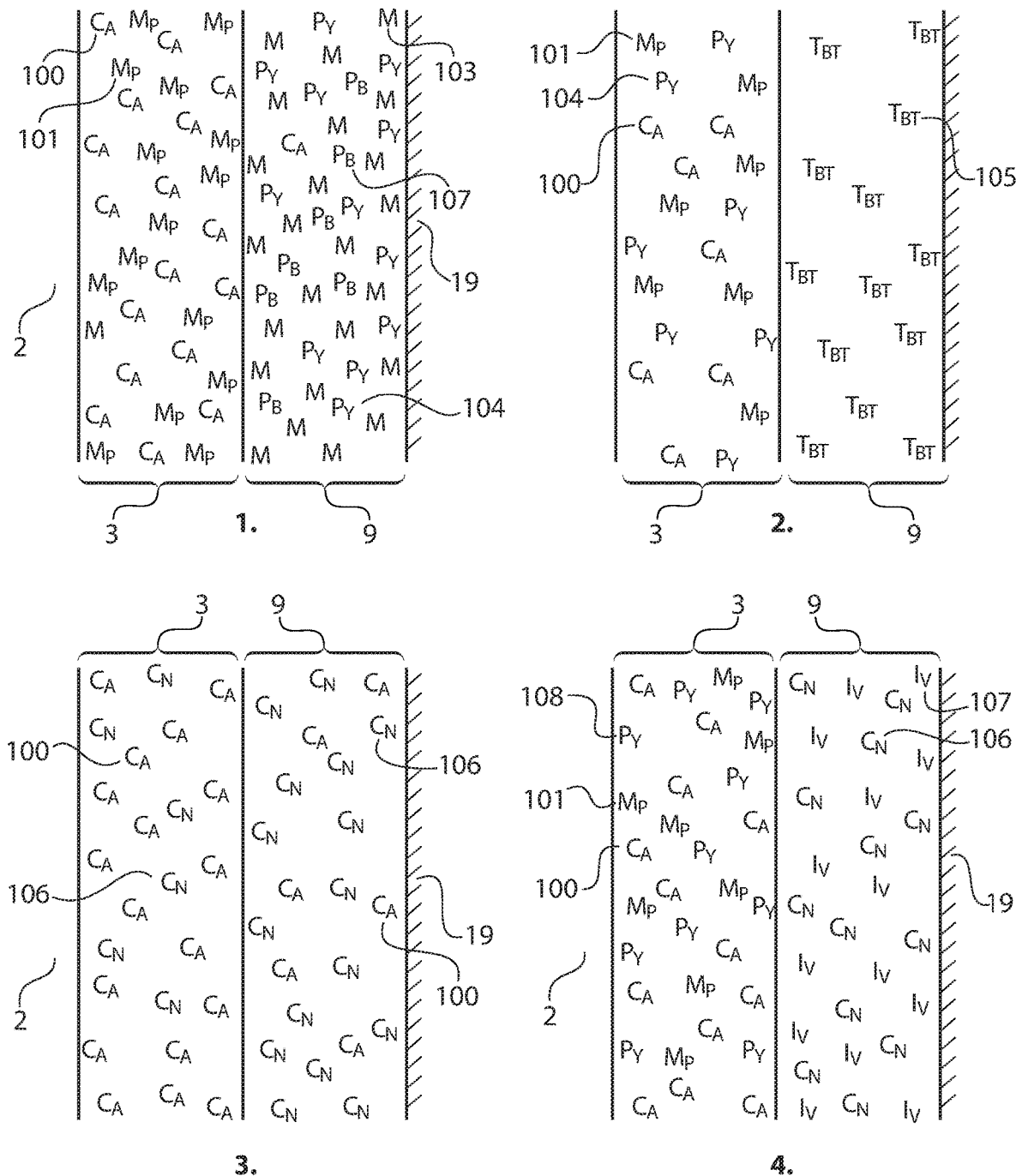
FIG. 10A depicts 4 cut-away views that illustrate the protective shielding effect of the outer biostatic polymer layer on the inner more potent biocidal polymer layer using various biocidal and biostatic biocides.

FIG. 10A depicts cut-away views of 4 additional structural embodiments of the current invention. Referring to FIG. 10A, both Polymer-O layer 3 and Polymer-I layer 9 can be made either biostatic or biocidal, such as in FIG. 10A(3) or the biocidal inner Polymer-I layer 9 can actually make use of a relatively toxic biocidal biocide like a copper or zinc salt such as in FIG. 10A(1) or a very toxic type of biocidal biocides such as TBT such as in FIG. 10A(2), because of the shielding effect of the outer Polymer-O 3 layer keeping the toxic biocide away from the aquatic environment so that it does not chemically leach out. FIG. 10A(4) is yet another variation where the Polymer-I uses two biocides, biocide cupro-nickel used in high concentrations along with another biocidal biocide, ivermectin, and the outer polymer-O layer 3 uses two biocidal agents, capsaicin, and low dose pyrethrin, as well at that layer having algaecide properties with the addition of a metal pyrithione salt.

FIG. 10A(1) shows an antifouling coating where the Polymer-O layer 3 contains the biostatic biocide, capsaicin (CA) 100 and a metal pyrithione (MP) 101, which provides invertebrate biostatic and algaecide properties to the outer polymer coating of the anti-fouling coating. Polymer-I is impregnated with the biocidal biocide, a high concentration pyrethrin or pyrethroid compound (PY) 104 together with piperonyl butoxide (PB) 107 and a biocidal metal or metal salt (M) 103 that can be copper, cuprous oxide, copper thiocyanate, zinc, zinc oxide, or zinc thiocyanate, and other metal compounds often used in metal based bottom boat paints. The result is an enhanced anti-fouling bi-laminar polymer paint coating that provides the benefits of copper based bottom paints, but with these benefits enhanced with synergistic lethality from the pyrethrin compound against invertebrate biofouling organisms, and an ability to prevent attachment of these organisms in the first place, as well as plant invasive species, accomplishing all of this without undesirable copper and zinc ions in the form of copper and zinc oxychloride chemically leaching into the aquatic environment. The killing of the invertebrates is done at the surface of the Polymer-I layer rather than being done in the water adjacent to the anti-fouling coating such as in the case of a copper-based paint.

A further demonstration of how effective this bi-laminar polymer structure can be in reducing the hazard potential of biocidal biocides used in the antifouling coating to the aquatic environment is depicted in FIG. 10A(2). Here an embodiment is shown which has an outer Polymer-O polymer layer 3 that includes the biostatic biocide, capsaicin (CA) 100, and the biostatic low-concentration pyrethrin (PY) 104 compound to produce the invertebrate biofouling attachment inhibition. However, the inner Polymer-I polymer layer contains only one biocidal biocide, the exceedingly potent, but banned TBT (tributyltin) (TBT) organo-tin compound 105 that is biocidal to all common and important biofouling organisms, plant or animal.

Normally, TBT is too toxic to the environment and thus cannot be used. However, with the bi-laminar polymer structure of the current invention, the TBT is contained completely within the Polymer-I layer 9, totally shielded from the aquatic environment by the outer Polymer-O layer 3. The maximal exposure of TBT to the aquatic environment would have a microscopic defect left by an occasional invertebrate biofouling organism that would manage to penetrate the Polymer-O layer and then be killed on contact with the TBT containing Polymer-I layer. Thus instead of an entire ship's hull leaching TBT continuously over time into the water just adjacent to the surface, the organism is killed only on contact with the TBT at the surface of the Polymer-I 9 and the maximum size of the surface exposed to the water would be a circle estimated to be about 0.1 mm in diameter (100 microns) or 0.0075 sq. mm, an amount of surface area that is so small that there is essentially no leakage of TBT into the aquatic environment. Furthermore, whatever microquantitative leaching would occur, it would occur in the first one or two weeks following the breach and killing of the organism and the TBT in that tiny area of exposure would stop leaching because of depletion of the TBT around the ringed pit left by the invertebrate shell after it fell off and died. Thus the current embodiments would allow even a very toxic biocide like TBT to be used safely. Note that a metal pyrithione salt (MP) 101 may also be added to the Polymer-O layer for algaecide properties. TBT is a potent algaecide, but since it must be kept from contact with the aquatic environment by containment within the Polymer-I layer 9 and shielded from the water by the Polymer-O layer 3, it cannot exert its algaecide properties as it won't be in contact with invading algae.

FIG. 10A(3) shows an embodiment of the present invention where the biofouling coating is composed of a Polymer-O layer 3 and a Polymer-I layer 9 that are both biostatic. While this embodiment might not be as potent as the prior embodiments discussed previously to this point, there are applications where simple inhibition of attachment of invertebrate biofouling organisms might be all that is required. These applications include protecting surfaces that are flexible, such as ropes, cables, and fishnets.

In FIG. 10A(3), a Polymer-O is shown that includes two biocides, a first biostatic biocide (e.g., cupro-nickel powder (CN) 106, in a 90%/10% by weight composition of copper to nickel with cupro-zinc or cupro-silver alloys, and brass powders being suitable substitutes in a composition by weight of 0.01% to 50%, but with a preferred composition by weight of 0.1% to 10%, with a particle size of a range of sub-micron to 100 microns) and a second biostatic biocide (e.g., capsaicin (CA) 100). A Polymer-I 9 may have a high relative concentration of cupro-nickel powder and a low relative concentration of capsaicin powder. Note that at lower concentrations by weight, cupro-nickel tends to be biostatic, and at higher concentrations, biocidal.

Of particular interest is the cupro-nickel powder, where the inherent solid solution alloy of this alloy and similar alloys, such as cupro-zinc and cupro-silver, has physical and chemical properties that result in no significant leaching of metal ions into the water, as the surface of such alloys are protected by a passivated layer. The only proviso is that these alloys should not be used in water with hydrogen sulfide being present (e.g., brackish swamp water with high bacterial counts of sulfide producing bacteria, such as where sewage is likely to be present or in a swamp), as these alloys would display undesirable corrosion into sulfides. Note that in this embodiment, in the Polymer-O layer 3 there is a high relative concentration of the capsaicin 104 biostatic biocide and a low relative concentration of the cupro-nickel 106 biostatic biocide. In the Polymer-I layer 9 the relationship is reversed, with a high relative concentration of the cupro-nickel biocide which, at these higher concentrations, is more biocidal and less biostatic but still nevertheless biostatic overall in nature, and a low relative concentration of the capsaicin.

Thus both the Polymer-O 3 and the Polymer-I 9 are biostatic. If an organism manages to resist the biostatic combination in the Polymer-O layer and attach itself there, it will be likely to be repelled by the reversal of the biostatic composition in the Polymer-I layer and disengage itself from the surface as soon as it contacts the inner biostatic layer. In this embodiment, the organism will most likely not be killed on contact with the Polymer-I layer but will likely die later after it detaches. Note that the capsaicin, as in all of the structural embodiments of the current inventions, is used either in the form of crystals, of 99% or better purity, or in the form of purified extract of greater than 95% purity at a percentage by weight ranging from 0.01% to 50%, with a preferred percentage by weight with a preferred range of 0.1% to 10%. In the case of the cupro-nickel, the same percentages mentioned above apply to the inner Polymer-I layer as well. Although the ratio of the concentration of the cupro-nickel powder in the outer Polymer-O layer as compared to the inner Polymer-I layer would be a preferred 1:10 ratio, that ratio could vary from 1:1 to as high as 1:1000.

In FIG. 10A(4) we have a structural embodiment of the current invention where the Polymer-O outer layer 3 is impregnated with biostatic biocide capsaicin (CA) 100, biostatic biocide low concentration of a pyrethrin or pyrethroid (PY) 108, and a metal pyrithione salt (MP) 101. Polymer-I inner layer 9 is impregnated with biostatic biocide Cupro-nickel powder (CN) 106, but in higher concentration, and biocidal biocide ivermectin (IV) 107. This combination of biocides results in a predominantly biostatic outer polymer layer with algaecide properties as well, and a predominantly biocidal inner polymer layer. The number of different variations and permutations possible to be suitable for various biofouling applications is extremely large and it would not be possible to go over each and every configuration possible that can comprise this invention. The examples provided herein are therefore solely illustrative and should not be considered limiting.

Medetomidine is a biostatic biocide with the unusual property that although it is relatively of higher water solubility of 186 mg/L, greater than the 100 mg/L limit previously specified, it nevertheless, is extremely tightly fixed within the polymer matrix it impregnates. As a result, in situations where shorter multiyear period of effectiveness is tolerable, such as coatings on cables, lobster traps, and ropes, its leaching rate will be low enough to allow its use in the outer biostatic Polymer-O layer. Its larvae repelling activity is based on the stimulation of the biofouling larvae nervous system via octopamine receptors causing convulsions of its muscular structures forcing the organism to pull away from the protected surface. It is effective in concentrations from 0.1% and higher though the preferred range would extend from 0.1% to 10%.

All the biocides that have been specified so far, and all the substitutions for such biocides, that are specified to be present in the Polymer-I and Polymer-O layers are comprising by weight about 0.01% to about 50% of the total weight of the compositions of the Polymer-I and Polymer-O layers, with a preferred range of about 0.1% to about 10% for biostatic biocides in the Polymer-O layer and about 0.1% to about 5% for biocidal biocides in the Polymer-I layer. These preferred ranges are known not to affect the mechanical, curing, or chemical properties of any of the polymers and provide, under usual circumstances of typical biofouling infestations, sufficient potency. Higher concentrations may be used for severe infestations, subject to limitation in some cases by the physical properties of certain polymers and/or their curing agents.

The preferred range, however, may vary for specific biocides used with specific polymers. The substituted biocides may be drawn from the lists of pesticides listed in the tables of FIG. 21, as well as the classes of compounds listed in the definition of terms section above. The maximum summed concentrations of all biocides in any layer of the antifouling coating should be a maximum of about 50% to avoid deleterious effects on the physical, chemical, and curing properties of the polymer layer that they impregnate, with a preferential range of about 0.01% to about 20%. Furthermore, the maximum summed concentration of all the biocides and fillers used in a given polymer layer of the antifouling coating should be about 50% at a maximum. It is noted, however, that some epoxy resin primers of the zinc-enriched type, which can serve in some applications as the Polymer-I layer, can have up to 90% by weight of zinc powder filler, indicating that certain polymers have physical and chemical characteristics that will allow the weight percentage on filler additives to exceed 50%.

Fillers that might be added to Polymer-O and Polymer-I include pigments, abrasives and hardness-enhancing particles. These fillers can also favorably impact adhesion and can include carbon fiber, aramid silica, fluorspar, stainless steel and other metals, boron carbide, other carbides, cubic boron nitride, industrial diamond powder, and friction-reducing fillers such as silicone powder, PFTE powder, molybdenum disulfide powder, non-cubic boron nitride, graphite flakes, graphene nanoplatelets, oxide, and flouride and may be present in a range of about 0.01% to about 50% by weight of the Polymer-O, Polymer-I, Primer-O, and Primer-I layers, with a preferential range of 1% to 15%. The size of such filler particles may range from sub-micron in size to 100 microns, with a preferential range being about 20 to about 50 microns for the abrasive fillers, and less than about 1 micron to about 20 microns for the friction-reducing fillers.

One non-organic biocide that is of beneficial use in this invention, cupro-nickel powder, may also be considered to be a filler material. However, because it is also a biocide, and smaller sized particles for a given mass of biocide have a greater relative surface area, allowing greater contact with the biofouling organism, the preferred particle size would be as small as possible, e.g., <20 microns, and preferably, <1 micron.

The sum total of all the biocide and non-biocide additives to the polymer layers is preferentially about 50% or less to minimize the possible effects on the curing, hardening, chemical, and mechanical properties of the polymer. Thus the percentages of some additives would put limits on the percentages of the other additives to ensure that the structural, mechanical, hardening, and chemical properties of the polymer to which they are added, which will form the polymer layers of this invention, would not be undesirably altered in a manner to degrade from its performance and structural and chemical integrity. The percentages of these components can be modified for specific applications. All such additional modifications and compositions that employ the structural aspects of this invention would be considered to be additional variations on the embodiments described in this disclosure for the current invention.

Figure 10B:
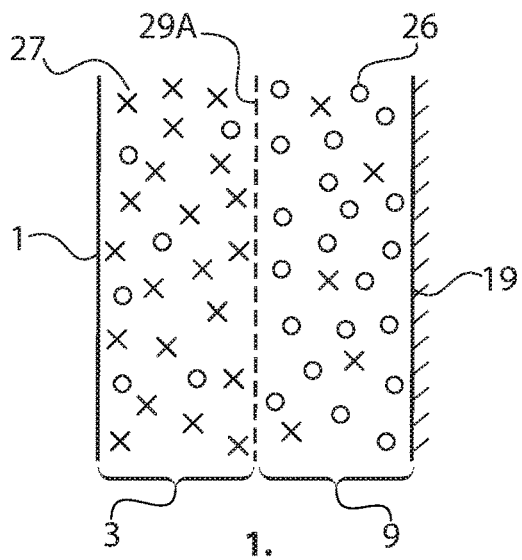
FIG. 10B depicts 6 cut-away views that illustrate several additional variation embodiments of the anti-fouling coating.
Figure 10B:
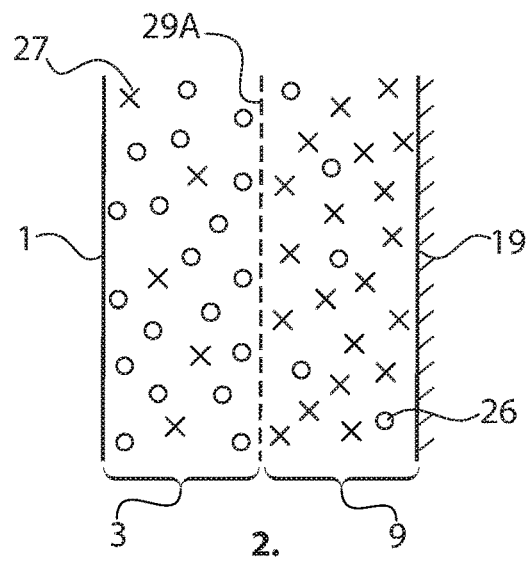
Figure 10B:
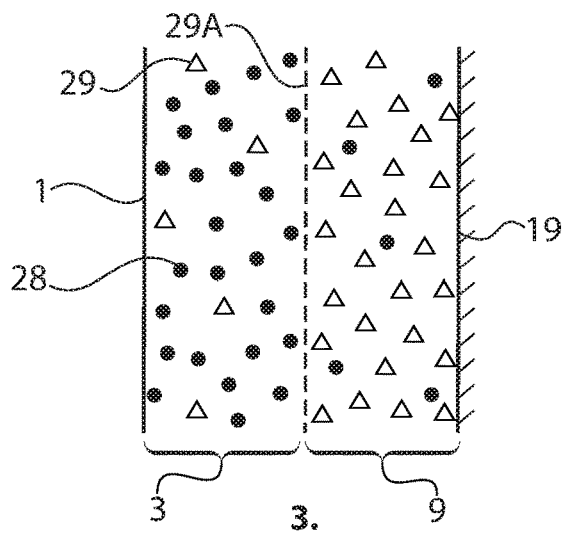
Figure 10B:
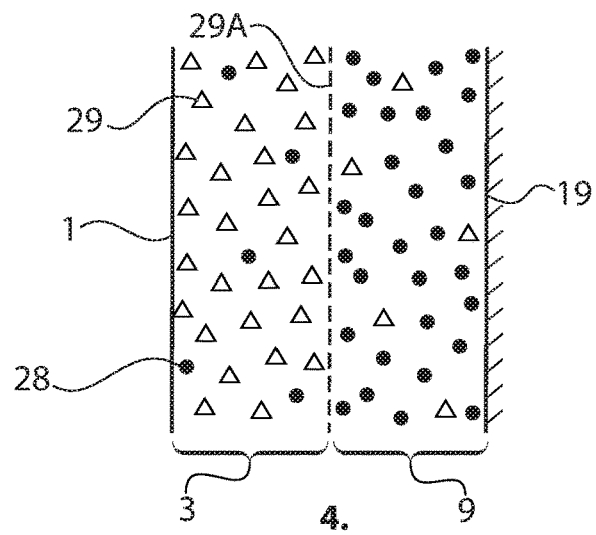
Figure 10B:
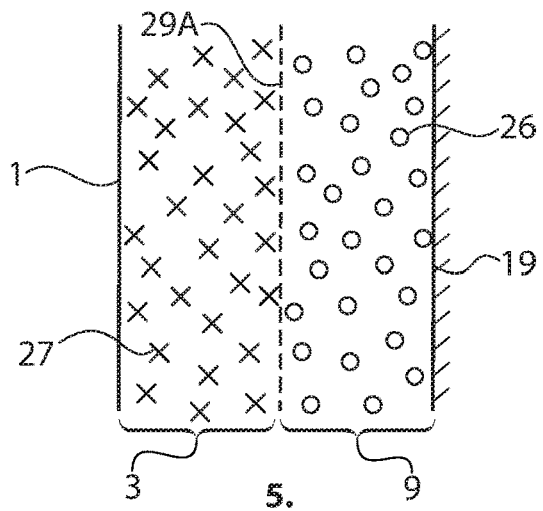
Figure 10B:
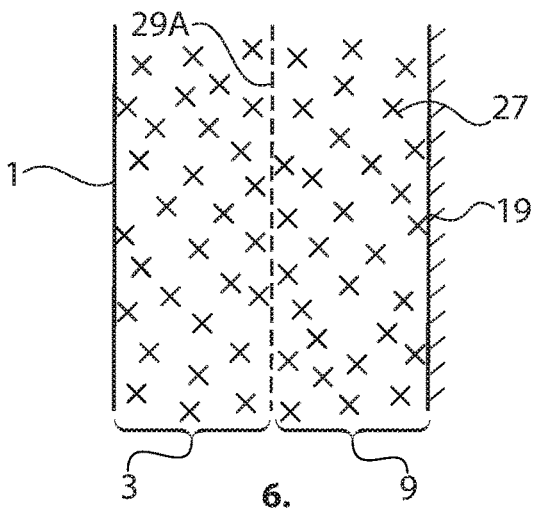

While all the structural embodiments so far have depicted the outer Polymer-O polymer layer as being biostatic in nature, because of the high relative concentration of the biostatic biocide as compared to the relative low relative concentration of the biocidal biocide in that Polymer-O layer, and have depicted the inner Polymer-I polymer layer as being biocidal in nature because of the high relative concentration of the biocidal biocide as compared to the relative low concentration of the biostatic biocide in that Polymer-I, there are several additional specialized embodiments that are depicted in FIG. 10B that can be useful in certain anti-fouling applications requiring exceptionally long life if exceptionally durable fluoropolymers are used together with more potent biocide arrangements.

In these embodiments, the polymer in both layers may be either a flourourethane, a flouro-ethylene-vinyl-ether (FEVE), or a related, extremely durable fluoropolymer. It is specified that the Polymer-O layer is applied onto the Polymer-I layer while the latter is only partly cured and still tacky, much in the same manner as the embodiments of FIGS. 2A and 2B, so that the ultimate structure will cure into a single fused layer that can contain different biocides depending upon the location depth within the fused coating. Furthermore, it is possible to make this fused, impregnated anti-fouling bilaminar polymer layer either totally biocidal, for seriously bio-fouled waters and difficult applications, or totally biostatic for less serious infestations or less critical applications.

This gives rise to additional structural arrangements of the biocides within the coating. For those embodiments that will contain both a biocidal Polymer-I and a biocidal Polymer-O layer, the embodiments will have an immediate biocidal effect, killing larval forms including veligers and cyprids as soon as they try to attach, rather than just a biostatic effect. If, in the relatively unlikely event that the outer biocidal Polymer-O layer does not kill the invasive organism, the inner biocidal Polymer-I will immediately kill the organism, as it would be extremely unlikely for the organism to be resistant to both biocidal biocide compositions in the two separate layers.

Relevant to the increased potency of this enhanced anti-fouling embodiment is the effect on the surrounding aquatic environment, which places limits on what biocides can be safely used, as biocidal biocides can come in contact with the surrounding aquatic environment.

FIG. 10B(1) shows a cut-away view of a structural embodiment of the anti-fouling coating where both the inner polymer layer Polymer-I 9 and the outer polymer layer Polymer-O 3 are biocidal and where in the Polymer-O layer 3, the concentration of the first biocidal biocide 27 (e.g., the anti-helminthic drug ivermectin), is present in a relatively high concentration, and a second biocidal biocide 26 (e.g., the anti-helminthic drug, lufenuron 26) is present in a relatively low concentration. The Polymer-I layer 9 includes the second biocidal biocide 26 in relatively high concentration and the first biocidal biocide 27 in a relatively low concentration. 29A indicates the fused interface of the Polymer-O and Polymer-I layers.

For this embodiment to be environmentally favorable, since now a biostatic shielding effect covering the biocidal layer is not present and the more potent biocidal biocide is now exposed to the water, the biocide in contact with the water is made water insoluble. Both ivermectin and lufenuron share this physical property and so both are suitable. Both may be substituted by other biocidal biocides as listed in the disclosure previously, for example, but any substituted chemical compound should have comparable or greater water insolubility. For example, suitable biocides may have a water solubility of less than about 20 mg/L, and preferably much less, as is the case of the two exemplary compounds Ivermectin (4 mg/L) and lufenuron (0.06 mg/L).

Note that lufenuron is a halogenated organic biocide (it has two chlorine atoms), but it is still considered to be desirable for use with the present invention. While under ordinary circumstances, chlorinated organic biocides are considered for the purposes of this invention too potentially hazardous to other aquatic environmental organisms, this exception can be made with lufenuron because it also has 8 fluorine atoms, which makes the compound so hydrophobic and water insoluble that it would be highly effective as an on-contact biocidal biocide against barnacles, mussels, and other chitin-containing, shell-forming biofouling organisms without any significant chemical leaching out into the water.

Also it is important to note that virtually all members of the pyrethrin class of biocides, when used in high concentrations as defined previously, especially with the adjunct compound, piperonyl butoxide, are biocidal and have water solubilities of up to over a magnitude less than even lufenuron and a KOC of greater than 100,000, and thus they would be acceptable substitutes for either ivermectin or lufenuron in this embodiment, as would any of the biocides listed in FIG. 21A, FIG. 21B, and FIG. 21D. Coupled with the fused bilaminar fluoropolymer coating, this combination of two biocidal biocides will provide an extremely long lasting and extremely potent antifouling coating that will be environmentally safe. This embodiment would be for severe fouling infestations or prevention of fouling in critical structures that are highly intolerant to even the slightest biofouling damage, and in areas where exposure of beneficial aquatic lifeforms is less problematical such as the interior of a large ship's plumbing system.

When the outer Polymer-O layer 3 is made biocidal in nature, other considerations may apply. Under certain circumstances, a water solubility of up to 100 mg/L may be acceptable when the biocidal molecule is of high molecular volume with a high adsorption coefficient, KOC, indicating a tight affinity to the matrix into which the biocide is impregnated. For instance, the macrocyclic lactone biocidal biocide, spinosad, which is a mixture of two compounds in a 5:1 ratio (similar to the preferred biocidal biocide ivermectin used in many of the embodiments of this invention which is also a mixture of macrocyclic lactones ivermectin 2-A and 2-B in a ratio of 4:1), and which is derived from a bacteria used in fermentation of sugar cane to alcohol, but which is not related to the ivermectin class of biocides, is an excellent biocidal biocide for this purpose of a biocidal Polymer-I layer exposed to the water. It has a solubility of less than about 100 mg/L but a very high KOC of 34,600 because of its huge molecular volume. Furthermore, spinosad has an especially low intrinsic aquatic hazard to other lifeforms, particularly if spinosad D, if used as a purified preparation with a decrease in the water solubility to an ultralow 0.33 mg/L, becomes a very desirable biocidal biocide. Numerous other exemplary substitutes listed in the tables of FIG. 21A, FIG. 21B, and FIG. 21C may be used.

The outer and inner fluoropolymer layers are fused together in the manner previously discussed. FIG. 10B(2) shows a cut away view of an anti-fouling coating, again with two fused biocidal polymer layers, but now with the concentrations of the biocides being reversed; lufenuron 26 is present in high relative concentration and ivermectin 27 is present in relatively low concentration in the Polymer-O layer 3 and ivermectin 27 is present in relatively high concentration and lufenuron is present in relatively low concentration in the Polymer-I layer 9. This embodiment, as in the case of the embodiment of FIG. 10B(1), may be desired when the infestation is more severe and the structure is more critical as far as anti-fouling damage. As in the case of FIG. 10B(2), being a reversal of compositions of FIG. 10B(1), FIG. 10B(4) shows compositions of biocides that are the reverse of FIG. 10B(3).

FIG. 10B(3) is a cut-away view that shows the same anti-fouling coating structure as FIG. 10B(1), except that now the two biocides are biostatic biocides giving the anti-fouling coating a solely biostatic effect. The same relative concentrations of the two biostatic biocides as was described for the two biocidal concentrations in FIGS. 10B(1) and (2) are present. Preferred exemplary biostatic biocides may include capsaicin 28 (whose water solubility is about 13 mg/L) as the first biocidal biocide in the in the outer polymer layer present in high relative concentration along with cupro-nickel powder 29 (whose water solubility is less than about 0.05 mg/L) in relatively low concentration and in the inner polymer layer and in the inner polymer layer the second biostatic biocide, cupro-nickel 29 is present in a high relative concentration and the first biostatic biocide, capsaicin 28, is present in a low relative concentration. As previously, the preferred ratio of concentrations is about 10:1 but may range from about 1:1 to about 1000:1. Again, these preferred exemplary biostatic biocides can be substituted with other compounds such as any of the pyrethrins in low concentration.

The water insolubility requirement for biostatic biocides is less stringent then with the biocidal biocides because they are more environmentally friendly, but solubilities of less than about 20 mg/L are still the preferable attribute that is desired for this invention for the purposes of a long duration anti-fouling effect with low leaching rates. Because biostatic biocide exposure to the aquatic environment is less potentially hazardous then biocidal exposure, biostatic biocides with water solubilities as high as about 100 mg/L, and especially those with a high KOC as low as 500, indicating a strong tendency for the biocide to remain fixed to the polymer matrix in which they are impregnated, are acceptable. Medetomidine has a water solubility of 186 mg/L, which is higher than some of the biocides being described, but its extremely high fixation to the polymer matrix compensates for the higher water solubility.

As in the case of FIG. 10B(2) being the reverse in terms of biocidal biocide concentrations in the two layers of the configuration in FIG. 10B(1), FIG. 10B(4) is the reverse in terms of biostatic biocide concentrations in the two layers of the configuration in FIG. 10B(3). The embodiments of FIG. 10B(3) and FIG. 10B(4), as they are composed of two biostatic polymer layers, do not have as intense an antifouling effect as the embodiments of FIG. 10B(1) and FIG. 10B(2) composed of two biocidal polymer layers, and thus wholly biostatic embodiments may be used for biofouling afflicted bodies of water where the infestation is more mild in nature.

FIG. 10B(5) depicts a cut-away view of a fused bilaminar fluoropolymer coating that is completely biocidal in nature, but in this embodiment first biocidal biocide 26 is completely segregated to the inner Polymer-I layer 9, while second biocidal biocide 27 is completely segregated to the outer Polymer-O layer 3, and both layers are biocidal. The advantage of this embodiment would be simplicity, cost savings, easier preparation and formation of the anti-fouling coating, preservation of the strongly biocidal character of the coating which would kill larval forms rather than inhibiting them or repelling them on contact with the outer layer of the coating. Not shown is the reverse composition embodiment of FIG. 10B(5), where the first biocidal biocide 26 impregnates the outer layer 9 and the second biocidal biocide 27 impregnates the inner layer 3, with the two layers fused together as explained previously. Another important chief advantage of the present embodiments is the greatly reduced chance of a resistant strain of organism destroying the polymer antifouling layer. If, by chance, a strain of barnacles or mussels develops resistance to a given biocide, the second biocide deeper within the structure of the antifouling coating will likely eliminate the resistant invading organism. This prevention of resistance effect would be more enhanced with two biocidal biocides as compared to two biostatic biocides.

FIG. 10B(6) depicts a cut-away view of an embodiment of the antifouling coating where the same biocidal biocide is in both the inner Polymer-I layer 9 that is fused by the method previously discussed to the outer Polymer-O layer 3. It is clear that by looking at FIG. 10B(1) that the high relative concentration of first biocidal biocide 27 can be kept constant in Polymer-O 3, while the low relative concentration of second biocide 26 can be reduced to zero, creating a Polymer-O 3 that just has the first biocidal biocide 27 impregnated into it. In Polymer-I 9, the high relative concentration of second biocide 26 can also be reduced to zero while the low concentration of first biocide 27 can be increased to equal that of the concentration of first biocide 27 in Polymer-O 3, creating in effect a single, double-thickness polymer layer of first biocidal biocide 27.

In fact, a durable polymer layer of arbitrary thickness can be laid down, impregnated with the single biocidal biocide by simply repeating the application of Polymer-O 3 without the low concentration of second biocidal biocide, similar to the process outlined in FIG. 1C. A similar process could be replicated with only using the second biocidal biocide and omitting the first biocidal biocide. The best applications for this particular embodiment would be for applications that require great durability and reasonable biofouling effectiveness to allow that durability to occur, where cost sensitivity is of high priority.

While it is not displayed in a figure, one further embodiment using just a single biocide, the embodiment of FIG. 1C where an individual polymer layer may be built up of several separate coatings to produce a desired thickness, and the features of FIG. 10B(6), is that a given polymer layer, either Polymer-O 3 or Polymer-I 9, can be made of several coatings, with each fused coating being impregnated with a successively higher (or lower) concentration of a biocide to produce a polymer layer whose depth of concentration of the biocide varies on a continuing basis with depth within the antifouling coating. Furthermore, this can be done with each of several biocides at once, including the arrangement where some biocides are gradually increasing with the depth of the coating, and some are decreasing. In that manner, the basic embodiment of FIG. 1A of this invention, when modified to accommodate the features of the embodiment of FIG. 1C and the embodiment of FIG. 10B(6), a single, fused multi-coating polymer layer is possible where, on a continuous basis with depth within the antifouling coating, the biostatic biocides decrease (or remain the same) with depth away from the water and the biocidal biocides increase (or remain the same) with depth away from the water.

This produces a coating that either becomes more biocidal with depth and less biostatic with depth, or alternatively, can remain uniform in composition with depth. Such a coating would be totally biostatic at the water's surface, and totally biocidal at the surface being protected. It is possible to apply this structural arrangement of continuously varying biocide concentrations to the Primer-I and Primer-O polymer layers as well.

When the biostatic nature of the outer biostatic Polymer-O layer 3 is modified to become biocidal like the inner biocidal layer in the manner of FIGS. 10B(5) and (6), certain ramifications need to be considered. The embodiments of FIGS. 10B(5) and (6) shed the shielding effect of the more environmentally gentle outer biostatic Polymer-O layer 3 in keeping the biocidal biocides away from the aquatic environment. Biocides in high concentration would then be in direct contact with the aquatic environment. To negate any possible effect on that environment, the biocides in the anti-fouling coating would be selected for favorable Higuchi Model physical properties as explained above, so that the leaching rate of the biocidal biocide or biocides, as predicted by the Higuchi Model, would be very low, keeping benign and beneficial aquatic organisms free from potential negative environmental effects.

In terms of the polymers that can be used in the current invention, the present embodiments specify that the polymers come from the list defined in the section on polymers described above. Any polymer, of either plastic or non-plastic type, and of rigid, semi-rigid, or flexible nature may be used in the polymer layers of the antifouling coating described in this invention. The previously specified list is not all-inclusive and any other suitable polymer may be used instead.

Two polymers of the class of polymers known as fluoropolymers in particular stand out as especially preferable for the current invention. The first is the class of compounds known as flourourethanes. These especially durable polymers have been tested under marine conditions and were found to have a durability exceeding 10 years and up to 15 years when applied to boats and ships. The second polymer is flouro-ethylene-vinyl-ether (FEVE) and its related polymers. When FEVE was coated onto bridges, it was found that the polymer could protect them from corrosion for at least 25 years, with some estimates as high as 100 years, and while these numbers would be expected to be shorter with continuous immersion in marine environments, a life expectancy of durability would be expected to be at least as great as the flourourethanes, and most likely even longer.

Both classes of polymers, because they are highly fluorinated and, to a degree, chemically related to PerTetraFlouroEthylene (PTFE), have exceedingly low coefficient of friction numbers associated with them, giving these polymers an inherent ability to shed biofouling invasions of protected surfaces coated with them as long as the surfaces were moving at sufficient rates of speed relative to the water at least a significant fraction of the time they were in the water. If calcareous calcium forming invertebrate biofouling species were not a problem, these two classes of coatings, once applied to the protected surfaces such as the hull of the ship would be expected to last for a decade.

However, once biofouling organisms make their presence known in the surrounding marine environment, and they are expected to attach and form destructive biomasses since the hard protective coatings formed by these polymers are quite attracting to such biofouling organisms, unless the protected surface moves frequently at high velocity through the water. When these otherwise extremely hard, smooth, and durable fluoropolymer surfaces are colonized by biofouling organisms, they degrade and are destroyed quickly by the relentless borrowing and destruction of the invertebrate's shell as it pierces not only the fluoropolymer coating but also the protected surface underneath. As a result, the biofouling organisms also quickly destroy the protected surface underneath from both bio-corrosion of the fouling species, but also chemical and galvanic corrosion of the protected surfaces underneath once access to the surface has been established by the water, especially seawater.

Thus even when fluoropolymers are used, when biofouling is present by calcareous invertebrate animals, the extremely long durable life of these fluoropolymers cannot be realized and old coatings have to be scraped off along with the barnacles and mussels and algae, and new coatings have to be applied to the submerged surface like a ship's hull at a frequency similar to that of non-fluoropolymer coatings.

It is the combination of fluoropolymers with multiple biocides, segregated and impregnated into layers of such fluoropolymers as depicted in structural embodiments depicted in FIGS. 1A, B, and C; C; 2A, B, and C; 5A and 5B; 6A and 6B; 7, 8; and 10A and B, that can produce such potent anti-fouling coatings that can be durable and effective over a long, multi-seasonal period of time, probably as long as a decade or longer. Furthermore, another major benefit of fluoropolymers are their excellent resistance to UV radiation. Fluoropolymers do not go brittle and deteriorate like other plastic polymers with prolonged exposure because of the high energy of the carbon-fluorine bond, as opposed to the carbon-hydrogen bond of most non-fluorinated plastic polymers. While submerged, only a small portion of UV radiation is absorbed by the water, so UV resistance is a necessary requirement of any coating.

For massive steel structures, such as bridges, oil platforms, and off shore wind turbines, the need to prevent corrosion is a major problem. It has been shown in Europe and Asia that oil platforms and bridges can be protected for at least 25 years, without the need for repainting, when a fluoropolymer coating such as FEVE is coated onto such structures with a zinc-rich primer to enhance adhesiveness between the fluoropolymer and the steel. For a thick steel structure, if a Primer-I inner primer coat of zinc-rich primer is applied to a suitably prepared surface, like a sandblasted ship's propeller, and a fluoropolymer inner biocidal Polymer-I layer undercoat, impregnated with the biocide compositions of the present embodiments, is coated onto the zinc rich primer, and then subsequently a fluoropolymer outer biostatic Polymer-O topcoat is added impregnated with the biocide compositions of the present embodiments, to produce the exemplary structure of FIG. 1C with or without an outer Primer-O coat, an anti-fouling effect on a ship's steel propeller or hull can be achieved that could easily last 10 years and perhaps far longer.

Clearly, however, if such coatings are applied, any damage to the coating as a result of a collision or accident with an object in the water would have to be repaired immediately. Using other types of durable epoxy primers, such durable anti-fouling coatings can be applied to aluminum, stainless steel, brass, bronze, wood, and plastic or any polymer structures, subject to any constraints involving possible unwanted galvanic action between the antifouling coating and the protected surface. It is also possible to impregnate the biocides of the Polymer-I layer into the zinc-rich or other types of epoxy polymer coatings, the Primer-I layer, so that the Primer-I layer and the Polymer-I layer become one and the same, giving beneficial rise to a propeller anti-fouling coating structure of only two layers.

Another advantageous use of this long-lived coating structure is the boat house. Boat houses, by their nature of being large, massive, and stationary objects, are difficult to get out of the water for maintenance in scraping of barnacles and mussels off their hulls, refurbishing their hulls, and repainting their surfaces. The present embodiments provide durable, low-maintenance hull coatings to help solve this problem.

Movable oil rigs are susceptible to new invasive species, such as several species of invasive shrimp and invasive crabs, among the more common forms of biofouling. These massive structural forms, like commercial seagoing vessels, have to be brought out of the water periodically and refurbished to remove the accrued biomasses. At least a dozen new organisms, virtually all of them being crustaceans that are chitin- and calcium-forming, have invaded areas of the ocean where these structures were brought into port for maintenance, resulting in local infestations that are expanding in area. Compounding the problem is that these creatures are not sessile and stationary, like invertebrate shell-forming organisms, but rather they are vagile and constantly moving among the sessile biofouling community implanted on the oil rig. They do not propagate by larval forms, such as cyprids and veligers that are seen with proliferating barnacle and invasive mussel species respectively, most of which die before attaining a site favorable for implantation and growth, but rather the whole organism removes itself from the oil rig and spreads into the non-native waters through which the slowly moving oil rigs are drawn the way to its maintenance station.

Furthermore although ships are more numerous, oil platforms tend to have a higher percentage of fouling cover—the entire surface of the oil rig usually gets bio-fouled, usually an area over about 5000 m2 on a typical rig. Commercial shipping vessels are larger, with container ships generally having about 7,000 to about 14,000 m2 of wetted area, but less than about 1% of the typical hull is fouled. The greater extent of biofouling on movable oil platforms may be due to being deployed and moored in stationary position for extended periods of time, as well as the fact that ships are moving through the water at considerable velocity, making it more difficult for a biofouling organism to get a hold.

At this time there has been no effective solution to this recent development of a new type of biofouling. However, the present embodiments are particularly appropriate for this problem, as they target all types of organisms that are members of the animal phylum, Arthropoda. Invasive shrimp and crabs are crustaceans, like barnacles, and thus any biocidal structures and compositional embodiments that would be effective against barnacles and invasive mussels will also be effective against this new form of biofouling. In this particular application, the current invention would be targeting organisms that do not spread by attachment of free floating larval forms that settle and attach on hard submerged surfaces, but instead those that prefer to move around on them. Thus the biostatic nature of the outer biostatic Polymer-O layer can be modified to become biocidal, like the inner biocidal layer in the manner of FIGS. 10B(5) and (6).

These two embodiments should be particularly efficacious for this problem, as the mobile invasive biofouling organisms would be killed on contact upon settling into position onto the mobile oil platform. While theoretically, some beneficial crustacean shrimp and crabs might be affected if they attempt to settle onto the oil platform, the vast number of them would stay on the ocean floor, away from the oil rig, and would not be affected as the biocides kill on contact with the surface rather than being released into the ocean. Furthermore, even though the embodiments of FIGS. 10B(5) and (6) shed the shielding effect of the outer Polymer-O layer in keeping the biocidal biocides away from the aquatic environment, the biocides in the anti-fouling coating would be selected for favorable Higuchi Model physical properties so that the leaching rate of the biocidal biocide or biocides would be immeasurably low, keeping benign and beneficial aquatic organisms free from potential negative environmental effects.

On the other hand, the multi-year durability required of the applications enumerated above is sometimes not required. For example, with anti-fouling coatings for high-speed power and racing boats, where it is absolutely necessary to maintain the coating to a high speed mirror finish, requiring frequent polishings during a boating season, the coating is often replaced yearly to maintain maximum low-friction performance. The coating thus not only provides anti-fouling protection to such a boat's surface, but also provides the lowest coefficient of friction between the speeding boat and the water flowing past.

The fillers described above are selected for increasing durability, adhesion, and complying with color pigment requirements. A group of fillers and additives may also be used that lower the friction of the surface of the Polymer-O layer with the surrounding water. These fillers include PTFE, molybdenum disulfide powder, non-cubic boron nitride, graphite flakes, silicone powder and graphene nano-platelets, graphene oxide, and graphene flouride. Note that boron carbide exists in two structural forms, the cubic form which used as an abrasive and wear-resistant substance as it is the second hardest substance known to mankind, and a soft non-cubic form which has lubricating properties similar to that of graphite. Hence boron nitride is a member of both the hard, abrasive wear-resistant filler group and the soft, friction-reducing filler group. The preferable particle size would be less than about 50 microns and the smaller the particles, the more advantageously friction with the water will be reduced.

Using a filler that includes a mixture of PTFE, molybdenum disulfide, and graphene nano-platelets, a mixture that has remarkably high lubricity and low static and dynamic friction, the filler mixture is added to the outer biostatic Polymer-O layer to would give this layer, and thus this embodiment, a low coefficient of friction that would be used to advantageously increase the speed and efficiency of high velocity water vessels such power, speed, and racing boats in addition to the reduction of friction produced from the prevention of fouling organism attachment. Furthermore, an algaecide may be added to the Polymer-O layer, as now attached algae, which can form and attach within one week, is not only a cosmetic nuisance, but also a friction-inducing factor.

Note that in this case, a shorter operational life of one boating season is acceptable. Instead of using the fluoropolymer as the coating matrix polymer itself, a short durability paint like a rosin paint or a silicone paint and the fluoropolymer, PTFE, may be used as a low friction filling agent rather than as the coating. The silicone paint polymer, if used in the Polymer-I and Polymer-O layers, will further add to the anti-friction effect of the special low friction fillers. This short operational-life embodiment is designed specifically for high velocity water vessels such as speed, power, and racing boats as well as personal high speed Sea-Doo® type water sleds, as the ultralow friction of this coating, achieved from the summation of a low-friction polymer coating, friction-reducing mixture of special low friction fillers, and prevention of biofouling attachment to the boat's surface from the antifouling coating, is more beneficial to this category of boat operation then a long multi-year operational life.

The percentage by weight of the Polymer-O low friction layer from the low friction fillers is preferably less than about 20% in the aggregate, though the range may be as high as up to about 50%, less the combined weight percentage by weight of the algaecide, the biocidal biocide, and the biostatic biocide. The coating of both the low-friction, outer biostatic Polymer layer and the inner biocidal Polymer-I layer ranges from about 5 mils to about 200 mils thick, depending upon the number of coatings of each layer are employed, similar to the physical thickness characteristics of all of the embodiments of this invention, with thick layers being built up of one or more coatings of the biocide impregnated polymer.

Figure 10C:
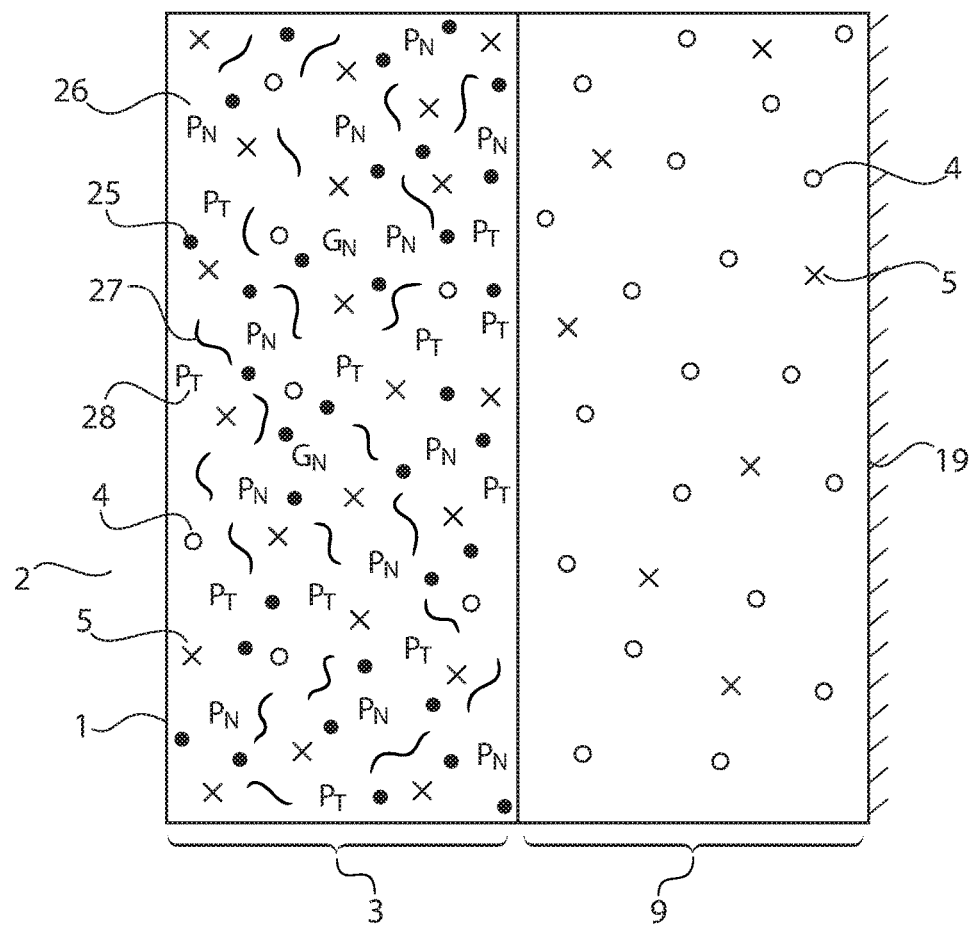
FIG. 10C depicts a cut-away view of an embodiment of the anti-fouling coating designed for rapid velocity water craft showing the presence of an algaecide and multiple low friction filler components.

FIG. 10C, which depicts a cross-section of the structural anti-fouling coating, giving a structural representation of this low-friction embodiment that is suitable for high velocity leisure and racing vessels. Inner biocidal Polymer-I layer 9 is depicted as before, with a high relative concentration of biocidal biocide 4 and with a low relative concentration of biostatic biocide 5. Outer biostatic Polymer-O layer 3 is depicted with a high relative concentration of biostatic biocide 5 and a low relative concentration of biocidal biocide 4. In this embodiment, Polymer-O 3 also contains the algaecide 26 in the form of zinc pyrithione or another metal salt or mixture of metal salts of pyrithione (Pn), as well as several fillers to enhance Polymer-O's low frictional nature against the rapidly moving water 2 that faces the aquatic surface 1 of Polymer-O 3. These low-friction filler particles of beneficial size less than 50 microns include PTFE (PT) 28, molybdenum disulfide 25, and graphene nano-platelets 27 and are all simultaneously used by the Polymer-O layer 3 to reduce the friction between the water and the antifouling coating. The protected surface is 19.

One advantageous aspect of this particular application is that, because high speed power and racing boat operators require their boats to be polished to maximum perfection on a weekly basis, a new layer of biocides and friction-reducing lubricants is exposed to the water after each polishing, keeping the low-friction properties and anti-fouling organism attachment inhibition of the outer biostatic Polymer-I always at a maximum with time. In effect, this polishing process acts like a soft abrasive paint, but the paint fragments are not released with time into the aquatic environment. Instead, the paint fragments are discarded in a safe manner on land.

In the laboratory, it has been shown that the combination of graphene, in the form of graphene nano-platelets, and PTFE, in the form of a powder, with further enhancement by molybdenum disulfide, a potent lubricant in its own right, has worked exceedingly well to reduce friction between sliding surfaces. When the sliding surfaces are water and a smooth surface that includes a silicone polymer or rosin polymer, with the mixture of PTFE powder and molybdenum disulfide lubricant fillers, its lubricity now enhanced by the further addition of graphene nano-platelets, the low frictional advantage exceeds previously described formulations for anti-fouling coatings. These low-friction materials have not been incorporated into polymers that are also impregnated with compositions of graphene nanoplatelets and mixtures of biocidal and biostatic biocides. The result is an antifouling coating of exceptionally low frictional resistance.

For applications other than high speed boating, which do require an anti-fouling coating with long durability and operational life as well as an extremely low coefficient of friction with the aquatic environment, the silicone or rosin polymer of the Polymer-O layer described for this particular embodiment used in competitive boat racing may be substituted with the polymer family most preferred with the present invention for long duration operational life, the fluoropolymers, including flourourethanes, flouro-ethylene-vinyl-ether (FEVE) and similar chemical structures. Such a coating will have an ultra-low frictional resistance, an ultra-long mechanical durability, an ultra-long anti-fouling effectiveness, an ultra-wide spectrum of anti-fouling effectiveness, and ultra-safe environmental compatibility.

Referring again to FIG. 10B(6), with reference to FIG. 10B(1), the high relative concentration of first biocidal biocide 27 can be kept constant in Polymer-O 3 while the low relative concentration of second biocide 26 can be reduced to zero, creating a Polymer-O 3 that just has the first biocidal biocide 27 impregnated into it. In Polymer-I 9, the high relative concentration of second biocide 26 can also be reduced to zero while the low concentration of first biocide 27 can be increased to equal that of the concentration of the first biocidal biocide 27 in Polymer-O 3, creating two polymer layers of the first biocidal biocide 27. Furthermore, if Polymer-O 3 is applied shortly after Polymer-I is applied and is still tacky and partially uncured, the Polymer-O 3 and Polymer-I 9 will fuse into a single, uniform layer of extra thickness containing a high relative concentration of the first biocidal biocide 27. A similar transformation of FIG. 10B(1) into FIG. 10B(6) can produce a single fused layer of extra thickness of a high relative dose of the second biocide 26. The fusing of the Polymer-O and Polymer-I layer, together containing a high concentration of just one biocide, now gives rise to another major use for the anti-fouling coating, those applications that require the ultimate in simplicity with respects to the logistics of applying the coating.

The problem of already established massive biomasses of fouling organisms that are so extensive, or are located in areas where they simply cannot be scraped off, remains an unsolved problem. This is particularly the case with invasive mussel species like the *quagga* mussel, the zebra mussel, and Mediterranean mussel than it is with barnacles, because the invasive mussels can cover, as was already pointed out, vast geographical areas such as the floor of the Great Lakes, Lake Mead, and Lake Powell in the US, can cover entire beaches, the surfaces of locks on freshwater canals, and other public recreational facilities. The continued presence of these massive biofouling deposits leads to the continued contamination of inland fresh bodies of water by the prodigious release of larval forms, by the millions per mussel, up to several times per year, with mussel densities as high as thousands per square meter. A continuing and spreading invasive mussel problem is the result. While chemical dispersals into small lakes have occasionally brought limited success, the intimate connection between most lakes of significant size and the human water supply and the human recreational environment and other uses simply makes this solution untenable. It is believed that an application and embodiment of the current invention represented by FIG. 10B(6) would be a safe and effective way to address this problem.

Figure 10D:
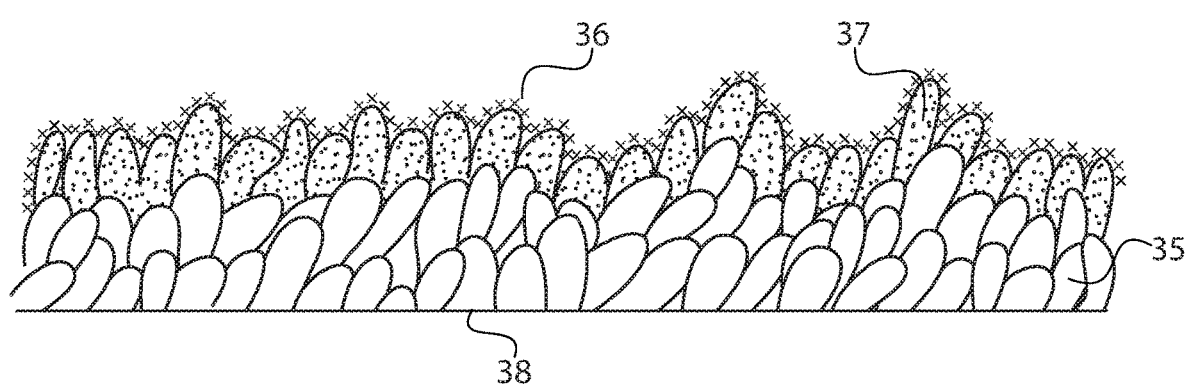
FIG. 10D depicts a cut-away view of an embodiment of the anti-fouling coating designed for eradicating heavy encrusted invertebrate biomasses from surfaces such as a beach or a lake bed.

Referring now to FIG. 10D, a mass 35 of invasive mussels is shown totally infesting and coating a surface which can be any natural or artificial surface whose size, location, and surface characteristics are such that the mussels cannot be scraped off and killed. Most of the biomass is dead, as more recently proliferating mussels smother and asphyxiate mussels located deeper in the biomass resulting, in a thin rim or coating of live proliferating mussels 37. The anti-fouling coating can be applied as a coating 36 to the top layer 37 of mussels that are exposed to air, water, and nutrients and are therefore, thriving. The coating will interact and entangle with the feeding structure mechanism of the mussels 37 and cause them to starve to death, and deprivation of their oxygen supply will cause them to asphyxiate. They will also be killed by the direct biocidal chemical effects on them.

It is estimated that within days, the entire biomass of mussels will be killed. On vertical surfaces they will be either sloughed off or form an inert exoskeleton where, if in a lake or river, beneficial life forms will colonize, and on horizontal surfaces like beaches, they will decompose, loosen their grip, and can either be left to disintegrate or the dead biomass can be carted away. There will be no more massive populations of live mussels other than a few survivors, and those few mussels that survive and the relatively few larvae forms they produce won't be able to attach because of the presence of the coating, and they will soon die. The proliferative chain of events leading to continued spread of the invasive mussels will be broken.

The application of the Polymer-I biocidal coating could be repeated multiple times in quick succession to produce a fused biocidal layer of considerable thickness in the manner of FIG. 10B(6) but only sufficiently thick to accomplish the necessary mussel eradication from the beach or lake bed or as needed to assure the most complete extermination of the invasive mussels. Alternatively, multiple coatings can be spaced out and applied to the encrusted surface at widely spaced intervals as separate applications as required to control the biofouling masses.

Depending upon the nature of the structure encrusted with mussels, the polymer used in the Polymer-I application can be adjusted. If the structure is an underwater lake, pond, or river bed, underwater curing epoxy polymers impregnated with the required specified biocides and with the longest possible operating life and highest durability can be used. Only those biocides with the lowest Higuchi Release Factors that are deemed safe enough for the human water supply and the human food chain would be used. Ivermectin of lufenuron for instance would result in virtually no biocidal levels in the water and the miniscule amounts that are released over time are UV degradable quickly over short periods of time.

Contrast this mode of application with the prior attempts made at sterilizing lakes of mussels by the dumping of insecticides directly into the lake. If the mussel-encrusted surface is a partially submerged surface, like a canal lock, the canal lock can be emptied of water for several hours while its mussel encrusted surface is coated with the Polymer-I anti-fouling coating (the Polymer-O coating is not needed on any of these applications, as the mussels are already in adult form and encrusted and just repelling larval forms would not be of much additional use. Again one would want to use polymers that would make the anti-fouling coating for these structures as durable and as long acting as possible.

However, a beach is an exceptional case where one would want to use a Polymer-I coating of transparent polymers that are short-lived and are designed to break up in ultraviolet light of the sun after a short duration of time, so that the beach returns to its normal consistency in the shortest period of time. For the beach application, the polymer would have to be either able to cure in a damp environment, or capable of underwater curing, or be rapidly curing so that the polymer antifouling coating could be applied to the encrusted mussels soon after low tide begins and the curing process is completed before the arrival of the next high tide. The biocides themselves would be chosen to be consistent with the needs of the present embodiments and according to the specified physical and chemical requirements of the application, which will result in a very high degree of human and environmental safety with very low biological risks either to humans and their water and food supply, or other beneficial animals in the aquatic environment.

The biocide used would have the property of being able to be broken down by ultraviolet light. A representative example of a suitable polymer-biocide combination for this application would be rapidly curing transparent epoxy coatings impregnated with ivermectin in the previously described weight compositions. Both the transparent epoxy and the ivermectin molecule are highly and rapidly degradable under sunlight and ultraviolet light. The thickness of the coatings used would vary from about 5 to about 200 mils depending upon the extensiveness of the encrustations.

Theoretically, the embodiment of this invention that would be used to annihilate the population of living invasive mussels from large structural surfaces and areas that have been contaminated and encrusted with large biomasses such as beaches, canal locks, piers, docks, and lake and river bottoms can be also applied be applied to barnacle infestations. However, since a barnacle infestation has exposure to the huge bodies of water represented by oceans, rather than the case of a confined and contained fresh body of water of relatively smaller size, a successful result would be more difficult to achieve.

Once a large mussel-encrusted area is successfully sterilized, which should not take more than a few weeks, one must next allow for preventing the layer of encrusted dead mussels from providing an excellent surface for newly arriving mussel larval forms that will restart the entire problem all over again. If the encrusted area is an area that is accessible and amenable for the mechanical stripping and carting away the dead mussels, then that would be the most preferred option. If it is a submerged, manmade structure such as a canal lock, the mussels can be stripped off, and the surface repainted with the present antifouling coating. However, if the encrusted area is a lake or river bottom, the preferred option would be to coat the dead mussel layer with the Polymer-I layer on it with a Polymer-O layer, again using a polymer capable of underwater curing, and impregnated with any of the preferred biocidal compositions that could comprise the Polymer-O biostatic layer of the current invention, with the added proviso that the chosen biocides would have to be absolutely safe for the human water supply and recreational water resources, using safe biocides such as capsaicin in the Polymer-O layer.

Application of a Polymer-O layer to the dead encrusted mussel layer coated with the previously applied Polymer-I layer will, in effect, coat the lake or river bottom with a durable antifouling coating which will repel and prevent further veliger larval settlement, thus breaking the proliferative life cycle of the invasive mussel, thereby both sterilizing that body of water of live invasive mussels, and preventing the spread of the infestation to other bodies of water.

Though the emphasis to this point has been on rigid surfaces, the embodiments of this invention extend to the protection of semi-rigid surfaces and structures, and even flexible surfaces and structures. If the polymer being used is a flexible polymer, such as a rubber, and it is impregnated with biocides, and it can be coated on such a flexible surface, the anti-fouling protection that the present embodiments afford can be applied to semi-rigid and flexible structures.

For instance, the non-plastic flexible polymer ethylene-propylene-diene-monomer (EPDM) has a lifetime of 25 years when submerged in marine conditions, and even longer in freshwater environments. It is applied as a liquid coating and then it is allowed to cure to a hardened, but flexible, polymer. EPDM is immune to UV light, chloride ions, and significant temperature extremes. It also has a modulus of elongation of about 200% to about 300%, so that it may be stretched like a spring, with a restorative force bringing it back to its original conformation and shape. If impregnated with biocides in the manner of this invention, it can give anti-fouling protection to a variety of flexible and stretchable materials and structures.

Figure 11A:
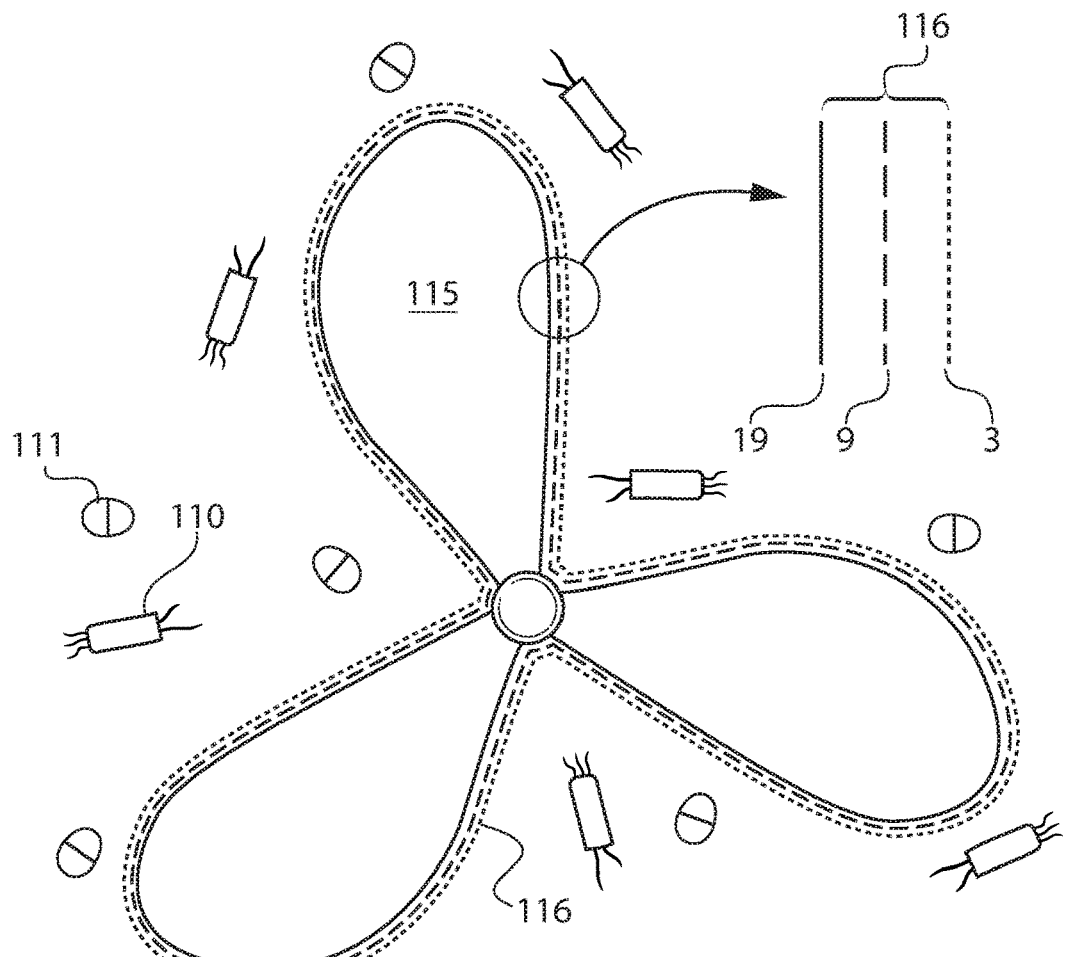
FIG. 11A depicts a propeller of a boat or ship coated with an anti-fouling coating comprising the current invention.

Referring now to FIG. 11A, a propeller is shown, onto which the anti-fouling coating is applied. Propellers can be made up of any appropriate material including, e.g., cast iron, steel, ceramics, aluminum, brass, fiberglass, stainless steel, or even wood. Barnacles and invasive mussels are especially problematic here, as the boat's propulsion through the water is generated by the propeller moving at high velocity against the water. Increased friction by mussels and barnacles here greatly can increase fuel consumption, slow the speed, and eventually destroy the propeller.

Furthermore, irregularities on the propeller blades due to adult barnacle and invasive mussel shells can create tremendous turbulence and cavitation, leading to vibrations up the propeller shaft, which can damage and destroy the engine proper. Stainless steel, even 316 type, thought to be relatively resistant to barnacle growth, and thought by some to be an expensive solution to biofouling, actually is not effective because of 3 mechanisms. First, the barnacle shell grows into the steel, resulting in pitting that allows chloride corrosion by destroying its protective passivated layer of chromium oxide. Second, the barnacle glue and byssel thread etches into the stainless steel and destroys its passivating protective layer because of the corrosive properties of the glue. Third, barnacle metabolism removes oxygen locally from the seawater, which is necessary for maintenance of the passivated chromium oxide layer. Invasive mussels also have byssel threads and mussel glue that cause the same problems, although the fresh water habitat of mussels does not involve chloride ion corrosion.

All three mechanisms result in chloride corrosion of the stainless steel in seawater by barnacles, while mussel glue corrosion and oxygen deprivation corrosion occur in freshwater. The only solution is to stop the biofouling infestation at the Stage 0 settlement and attachment stage, or at the latest, the Stage 1 metamorphosis and juvenile stage.

Figure 11B:
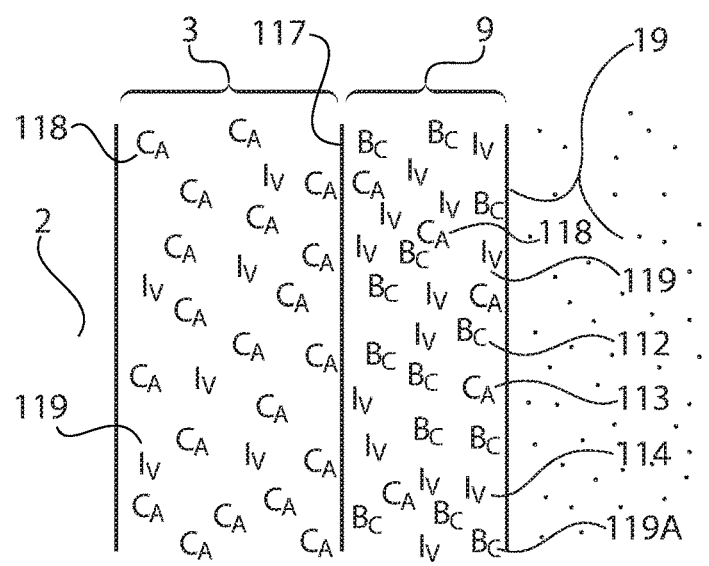
FIG. 11B depicts a cut-away view of the propeller's thickness and shown coated with the outer biostatic polymer layer and the inner biocidal polymer layer also functioning as an inner polymer primer layer with Ivermectin as the biocidal biocide and capsaicin as the biostatic biocide, with the presence of boron carbide particles in the primer layer.

In FIG. 11A barnacle cyprids in salt water 110 and mussel veligers in fresh water 111 are seen floating in the water and are prepared to attach themselves to the propeller 115, to which the anti-fouling coating 116 is applied. Coating 116 is blown up in the inset drawing to reveal the propeller surface to be protected 19, inner biocidal polymer layer Polymer-I 9, and the outer biostatic polymer layer Polymer-O 3. Antifouling coating 116 is further blown up in FIG. 11B to reveal a cut-away view similar to previous structural embodiments.

Biostatic larval attachment inhibition is provided by Polymer-O 3, which may include a fluoropolymer such as a flourourethanes, or FEVE, and which may be impregnated with a high relative concentration of a biostatic biocide 118 such as purified capsaicin (CA) and a low relative concentration of a biocidal biocide 119 such as ivermectin (IV). The biocidal killing function is provided by Polymer-I 9, which is impregnated with a relatively high concentration of the biocidal biocide 119 and a relatively low concentration of the biostatic biocide 118. The boundary 117 between Polymer-O 3 and Polymer-I 9 is shown, as is the aquatic environment 2, and the propeller surface 19 and structure itself.

In addition, Polymer-O 3 is also impregnated with particles of boron carbide 119A between about 1 and about 100 microns in size with an optimal range of about 7 and about 50 microns to increase the adhesion of the Polymer-O layer 3 to the propeller 19. The polymer component of Polymer-I 9 is not a fluoropolymer but rather may be an epoxy resin adhesive primer of high adhesive strength to create as strong as bond as possible for the coating to the propeller, as that coating is subjected to tremendous frictional forces and centripetal forces of the rotation of the propeller, as well as the forward velocity of the boat or ship.

In this application the Polymer-I layer 9 and the Primer-I layer are one in the same, and this single layer performs the dual functions of a biocidal polymer layer and a primer polymer layer, giving the antifouling coating a dual layer structure. If the propeller is made of cast iron or a steel alloy, the Polymer-I primer is preferentially a zinc-rich inorganic or organic epoxy primer for long life. If in this application the Polymer-I 9 were structured to be a separate layer from the Primer-I coating because a separate inorganic zinc-rich primer is used, the antifouling coating would be a three-layer structure rather than a two-layered one.

The low frictional nature of Polymer-O 3 in a two-layer antifouling coating improves the efficiency of the propeller from reduced friction and the durability of the antifouling coating. In a three-layer antifouling unit, a fluoropolymer layer of the Polymer-O layer 3 again improves the efficiency of the propeller from reduced friction, and the two layers of the fluoropolymer comprising both Polymer-O 3 and Polymer-I 9 greatly enhance the durability of the antifouling coating. Frictional forces can be reduced even further with the addition of combinations of various low friction fillers from the group previously described, and the preferred combination of PTFE powder, molybdenum disulfide powder, and graphene nano-platelets being particularly effective in this regard.

Figure 12A:
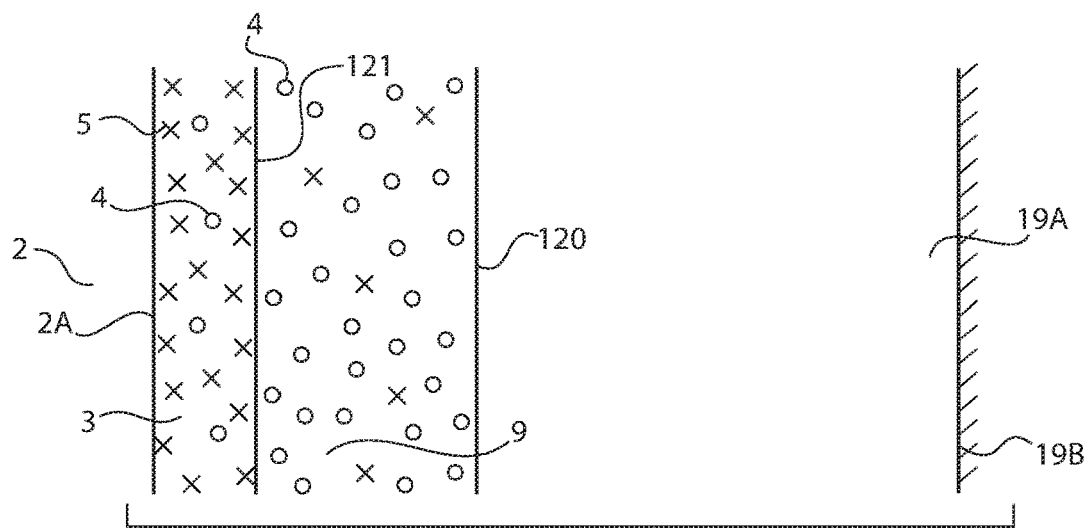
FIG. 12A depicts a cut-away view of a boat's fiberglass hull that contains no biocide but is covered by a biocidal inner polymer layer containing both a biocidal biocide in high concentration and a biostatic biocide in low concentration and a "gelcoat" outer biostatic polymer layer containing both a biostatic biocide in high concentration and a biocidal biocide in low concentration.

Referring now to FIG. 12, the application of a fiberglass resin "Gelcoat" to a fiberglass boat hull is shown. FIG. 12A depicts a cut-away view of boat hull 19A with its interior surface 19B facing the interior of the boat. The boat hull 19A is coated with an inner bottom coat Polymer-I biocidal layer 9 whose polymer can be a preferred resin paint or any other type of paint. It is impregnated with a high relative concentration of a biocidal biocide and a relatively low concentration of a biostatic biocide. The Polymer-I layer 9 is covered by an outer topcoat of Polymer-O biostatic layer 3 that includes a polymer of the resin polymer category that ordinarily would be used in "Gelcoat" final outer coatings of boats when they are first manufactured. The Polymer-O layer 3 is impregnated with a relatively high concentration of biostatic biocide and a relatively low concentration of biocidal biocide. The "Gelcoat" is most often comprised of fiberglass resin but may be formed from any appropriate polymer. The boundary 120 between the fiberglass hull and the Polymer-I layer 9 is shown, as is the boundary 121 between the Polymer-I layer 9 and Polymer-O layer 3, the aquatic environment 2, and the water surface side 2A of Polymer-O 3. A transparent fluoropolymer may be substituted for the fiberglass resin "Gelcoat".

Figure 12B:
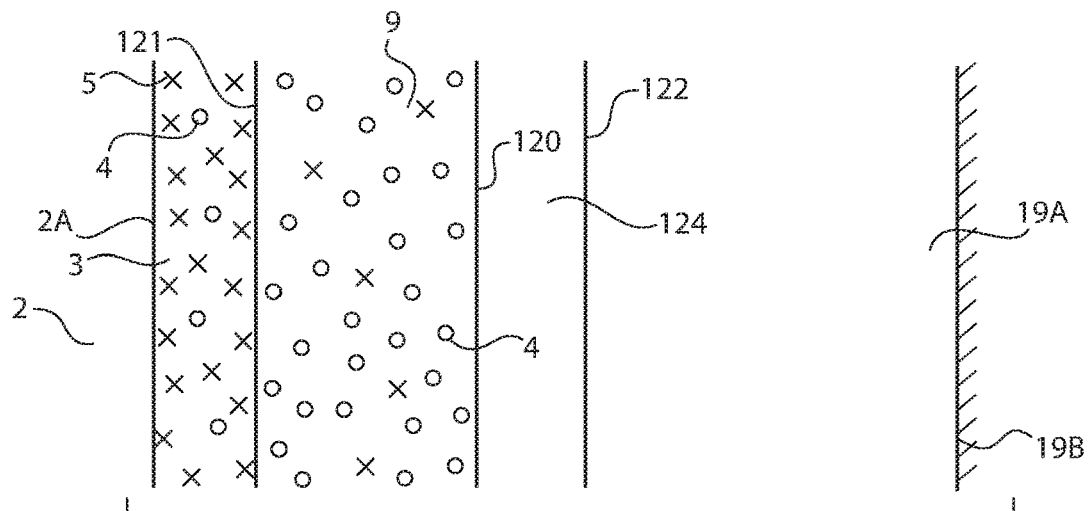
FIG. 12B depicts a cut-away view of a boat's fiberglass hull that contains no biocide but is covered in the same manner as the hull in FIG. 12A but in addition, an inner polymer primer lies between the hull and the inner biocidal polymer layer.
Figure 12C:
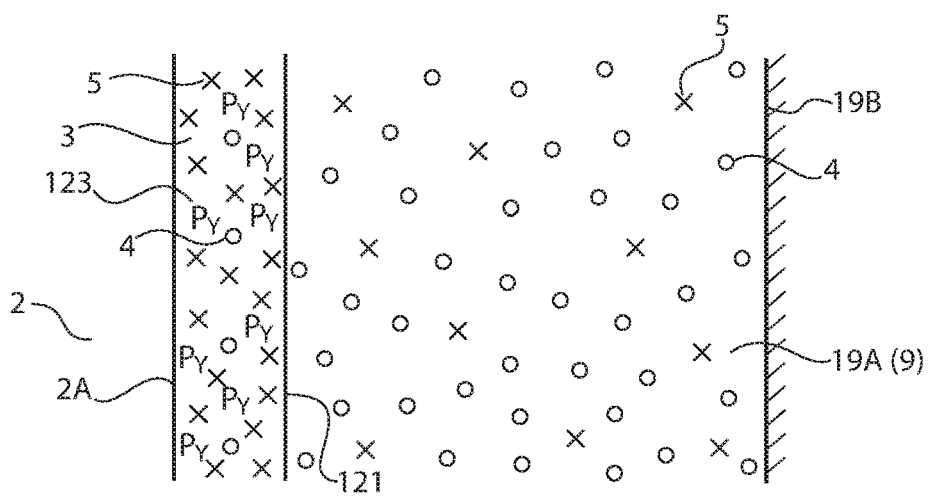
FIG. 12C depicts a cut-away view of a boat's fiberglass hull that contains both a biocidal biocide in high concentration and a biostatic biocide in low concentration, both added to the fiberglass at the time of manufacture of the boat, making the hull the inner biocidal polymer layer which is covered by a "gelcoat" outer biostatic polymer layer of a biostatic biocide in high concentration, a biocidal biocide in low concentration, and which also contains an algaecide, a pyrithione metal salt.

Referring now to FIG. 12B, the same cut-away structure is shown as in FIG. 12A, but with the inclusion of an inner primer polymer layer 124. FIG. 12C shows an embodiment where the fiberglass hull itself is part of the anti-fouling coating. At the time of manufacture, the biocides are added to the fiberglass at the time the boat hull is molded or manufactured. It is important that the boat hull always be biocidal, as any barnacle or mussel that might penetrate the outer polymer coating "Gelcoat" would be highly destructive to the boat because the boat hull itself would be the next polymer layer invaded.

Boat hull 19A (also labeled as 9) with its inner surface 19B facing the interior of the boat is impregnated with a relatively high concentration of a biocidal biocide like ivermectin 4 and a relatively low concentration of a biostatic biocide such as purified capsaicin 5. Essentially the fiberglass boat hull has become biocidal inner polymer layer Polymer-I 9. The process of adding biocides to fiberglass resin composites at the time of manufacture has been described schematically with FIG. 2B and the description associated with FIG. 2B. The boundary between Polymer-O and Polymer-I is 121. Polymer-O is now the "Gelcoat", that may be transparent or colored if pigment is added to it, again would be comprised of fiberglass resin, or as a substitute, a fluoropolymer, or any other suitable polymer, and would be impregnated with a relatively high concentration of biostatic purified capsaicin 5 and a relatively low concentration of biocidal ivermectin 4.

In addition, an algaecide, a metal salt pyrithione (PY) 123, has been optionally added to Polymer-O 3. Prevention of algae accumulation on the boat, though easily removed and not responsible for anywhere near the functional friction problems and structural damage as seen with the invertebrate calcium forming organisms, nevertheless is a cosmetic feature desired by most luxury boat owners. Cosmetic appearance would be less of a concern for large commercial vessels.

Figure 13A:
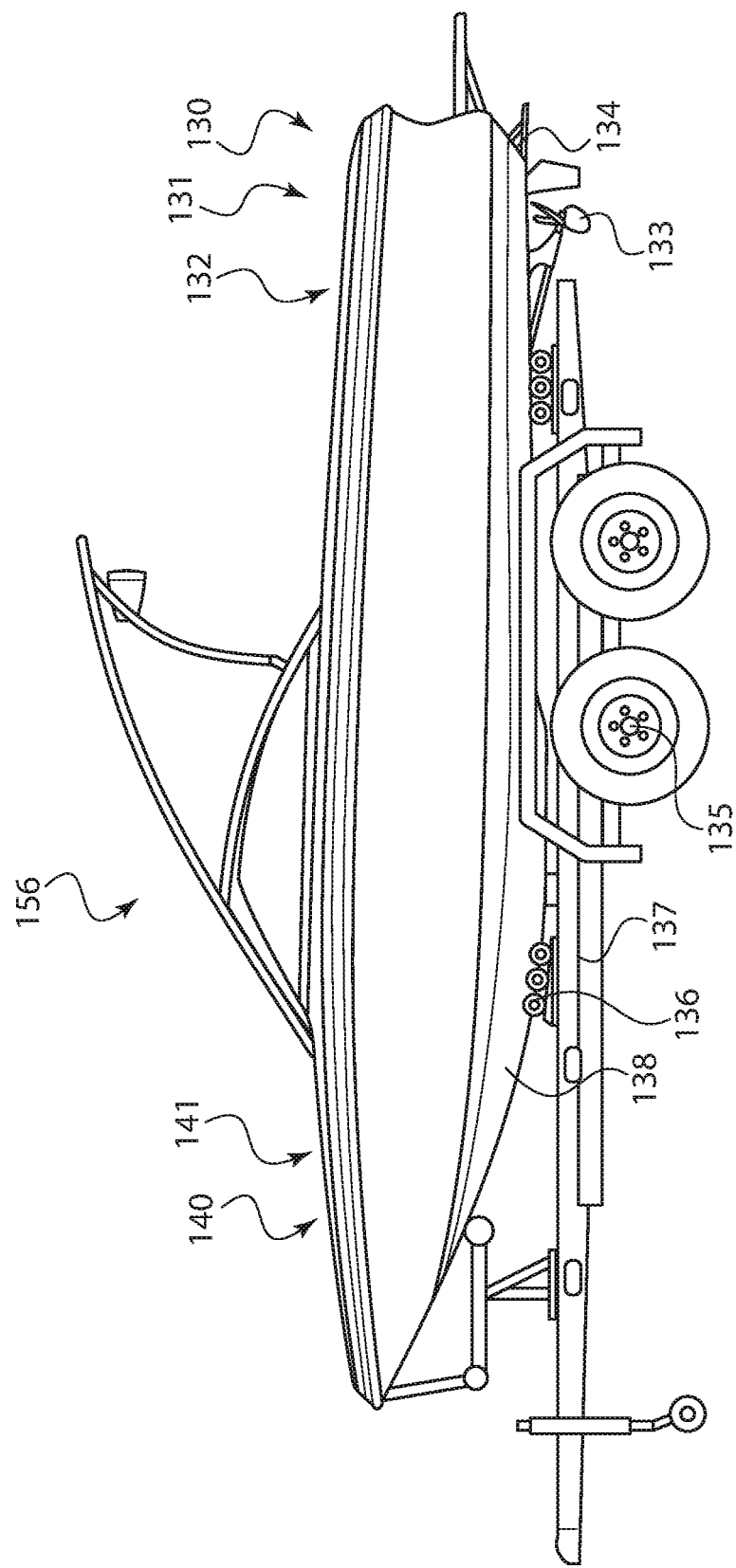
FIG. 13A depicts a diagram of a boat and its transportation accessory equipment illustrating structures that require anti-fouling protection.

FIG. 13A, B, C depict high risk applications where the use of the biofouling coating of this invention may not only protect vital marine and fresh water structures from malfunction and destruction, but also may slow the contagious spread of invertebrate species biofouling caused by the larval contamination of these structures, especially in inland bodies of water where leisure boats are brought from location to location, and in ocean bodies of water where spreading the contagious mussels in fresh water and barnacles in salt water occurs due to larval contamination of bilge pumps and ship plumbing systems.

FIG. 13A shows a leisure boat 156 and all of the structures at risk for biofouling where the use of the biofouling coatings of this invention would prove applicable. Shown is anchor 130 (not seen under the boat), bilge 131 and live wells 132 (not shown in interior of the boat), propeller 133, storage compartments 141 and dock lines 140 (not shown in the interior of the boat), motor intake 134, wheels and wheel axle 135, hull 138 and roller bunks 136. Boating transport accessories subject to biofouling infestations include hitch 139, and trailer 137.

Even if no visible barnacles or mussels are seen on these structures when transporting boats from one body of water to another overland, movement of leisure boats can transport invisible veligers and cyprids on their surfaces, which can resist desiccation for up to several days on damp surfaces, or they can contaminate bilge areas, allowing contagious spread to unaffected bodies of water. If a lake is infected with *quagga* mussels or zebra mussels, the water may be infected with up to hundreds of thousands of veligers per cubic meter that will contaminate surfaces as they are removed from the water for transport. All of these listed structures are amenable for the anti-fouling coating of this invention. Such spread of biofouling organisms through their larval forms can be totally prevented with this type of anti-fouling coating. The damage to all of these listed structures on the boat in terms of corrosion from invertebrate biofoulers as well as malfunction of engines, other boating parts, loss of speed, and increased fuel consumption are all completely preventable. Correction of these problems on a global scale with transoceanic shipping vessels will markedly reduce carbon emissions, reduce fuel consumption, and ameliorate one of the factors causing global warming.

Figure 13C:
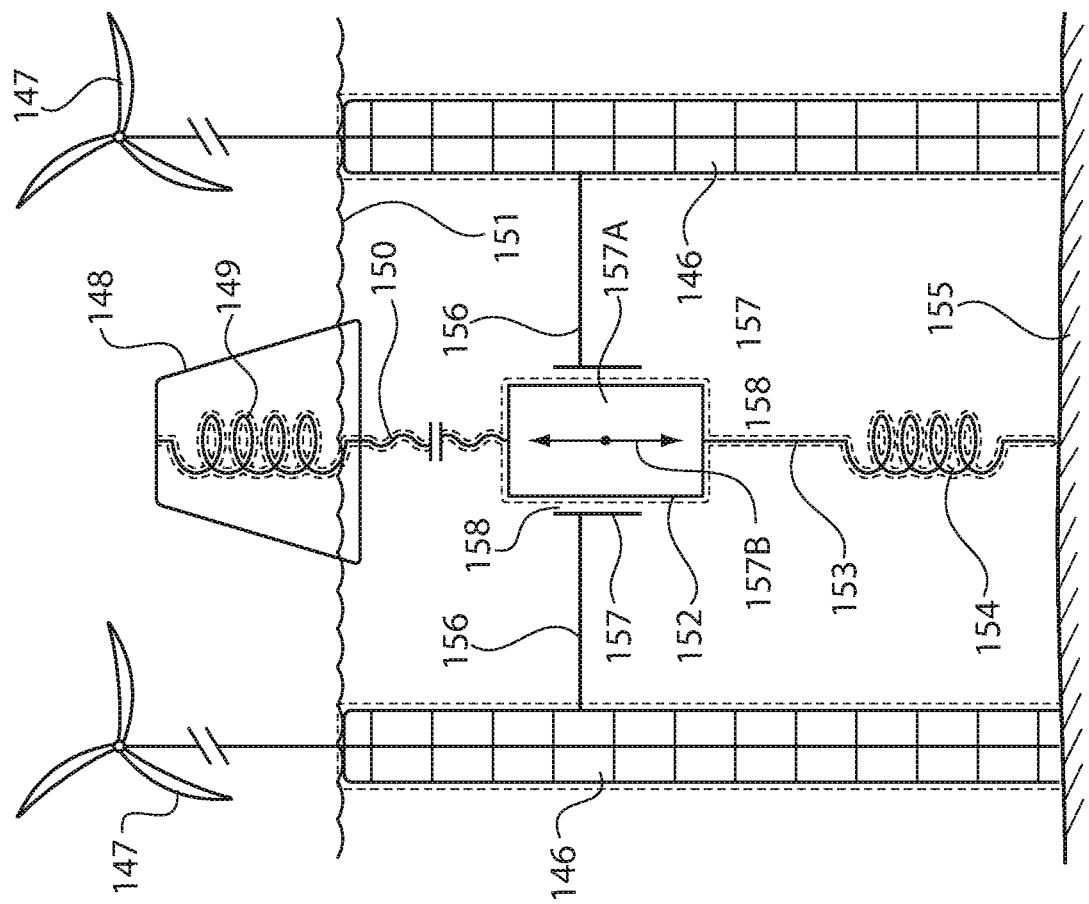
FIG. 13C depicts a hybrid off shore wind and wave farm indicating structures that require anti-fouling protection.
Figure 13B:
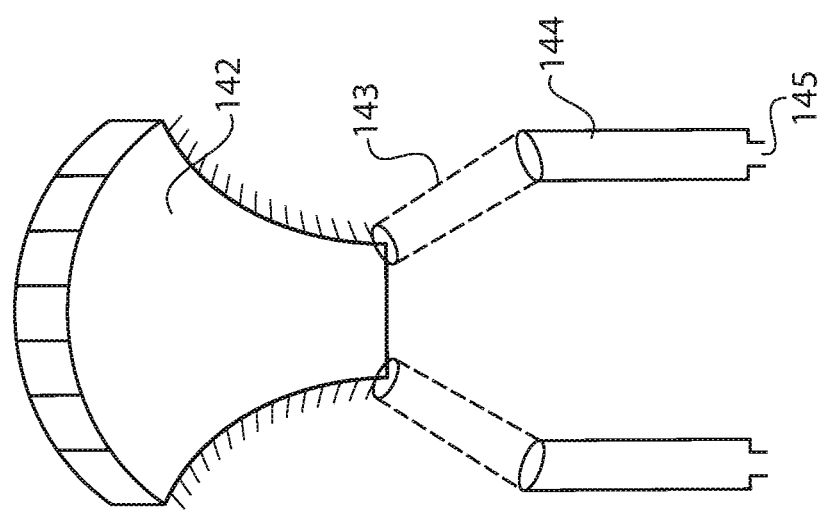
FIG. 13B depicts a diagram of a power station water intake system downstream from a dam that requires anti-fouling protection.

FIG. 13B shows a schematic drawing of a hydroelectric plant. Dam 142 sends water via its outtake channels 143 to hydroelectric generators 144 and the used water is emptied downstream by exit pipes 145. Throughout the water flow path through structures 143, 144, and 145, as well as intake grates and filters (not shown), this anti-fouling coating can be applied to prevent biofouling accumulation which can otherwise block water flow, reduce electrical energy generation, and most importantly, damage expensive hydroelectric generators if anti-fouling organisms proliferate within these apparatuses. Also, one must note that proliferation of organisms in these locations increase the spread of veligers of invasive mussels to spread the contamination downstream.

FIG. 13C depicts a schematic drawing of an off-shore wind wave energy harvesting farm that serves as an application embodiment of the current invention. There are two wind turbines 147 supported by two pylons 146 resting on seabed 155. A wave energy converter includes a buoy 148 floating on the surface of the ocean 151 in motion (indicated by arrows 157B) from the passage of waves acting through a mass spring system made up of springs 149 and 154, which move a linear electric generator 157A with metal enclosure 152 in synchrony with the passage of ocean waves. The generator is held in place by braces 156 connected to the pylons of the wind turbines and two circular slide bearings 157 through which the generator slides in a vertical oscillatory linear motion in synchrony with the waves. Since this would be considered a marine installation, barnacles inevitably will try to attach and grow. All the structures outlined in dotted lines are subject to damage by barnacles.

While the pythons would sustain surface corrosion damage, because they are massive and stationary, the barnacle problem would be limited to expensive periodic scraping maintenance sessions. However, with the wave energy converter, barnacles getting onto moving bearing surfaces 158 will destroy the generator, and barnacles getting onto the bottom of the buoy, spring 154 and cable 153 and stretchable cable 153 will add weight to the generator, effect the buoyancy of the float, and impair the transmission of the energy of the waves down to the generator as well as possible rupture of the cables. While this wave energy generator is an exemplary structure, wave energy generators of all types and mechanisms are subject to malfunction and early lifetime termination from barnacle attachment and growth. Application of the present embodiments to all of the structures outlined with a dotted line on FIG. 13C would prevent these problems for an extended period of time.

Figure 14A:
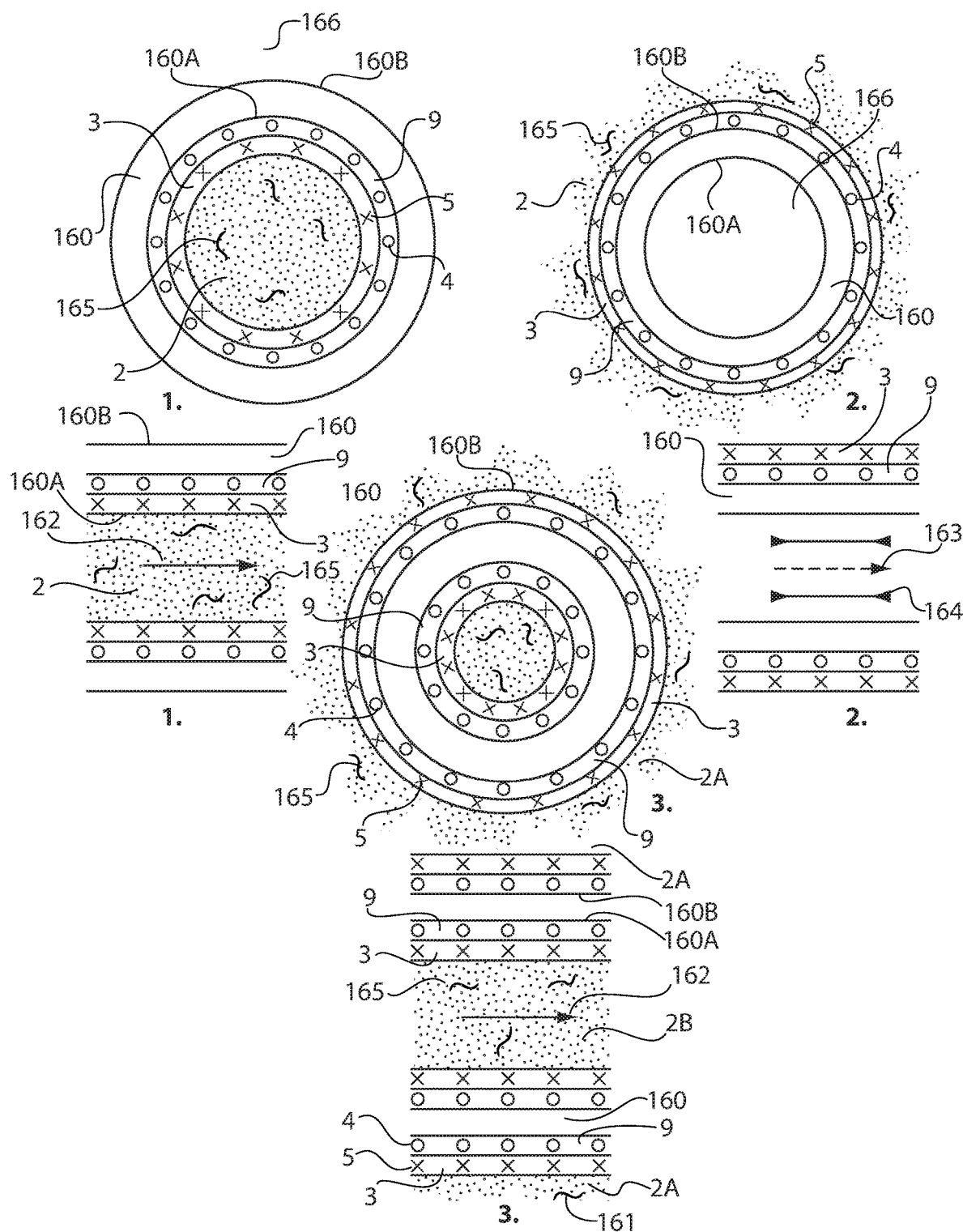
FIG. 14A depicts cross section and side cut-away views of a pipe without impregnated biocide coated on the inside, the outside, or both with an inner biocidal polymer layer and an outer biostatic polymer layer.

FIGS. 14A(1), (2), and (3) depict cross-sectional and longitudinal side views of pipes whose surfaces are protected from fouling by an application embodiment of the anti-fouling coatings comprising this invention. FIG. 14A (1), upper diagram, depicts a cross-sectional view of pipe 160 surrounded by non-contaminated water or other material in exterior space 166, which may include plastic such as PVC, or metal such as copper, stainless steel, titanium or other suitable corrosion resistant metal or alloy.

Pipe 160's inner surface 160A is exposed to water 2, which is contaminated with either barnacle cyprids or mussel veligers 165. The pipe's inner surface 160 is coated by an inner polymer layer, Polymer-I 9, that is biocidal (4) in nature. In turn, Polymer-I 9 is coated by an outer polymer layer, Polymer-O 3, that is biostatic (5) in nature. The outer surface 160B of the pipe not exposed to water is shown. FIG. 14A(1), lower diagram, depicts the side longitudinal cutaway view of the pipe in the upper diagram of FIG. 14A(1). The direction of the flow of water is indicated by arrow 162. The antifouling coating will prevent the development of mussels or barnacles within this pipe.

FIG. 14A(2), upper diagram, depicts a cross-sectional view of pipe 160 coated with the anti-fouling coating comprising this invention, only now the polymer layers Polymer-I 9 and Polymer-O 3 are on the outside of the pipe 160B, as the pipe's outer surface 160B is now exposed to the water 2 and the cyprid or veliger larval forms 165. Otherwise, the structures depicted are identical in all respects to that of FIG. 14A(1), upper diagram. Likewise, the lower diagram of FIG. 14A(2) is the same in all respects to that of the lower diagram of FIG. 14A(1) except for the bi-laminar polymer layer comprising Polymer-I 9 and Polymer-O 3 are on the outside surface of the pipe, 160B. One-sided arrow 163 represents the flow direction of some liquid or gas in the interior of the pipe 166 with inside wall 160A which could also include water that is not infested with barnacle or mussel larvae. Two-sided arrows 164 represent other uses for the pipe, such as conductive cables being carried within the interior of the pipe. This embodiment is shown in both FIG. 20A, where it is depicted as being employed in a barnacle protected ocean wave energy converter and seawater electrolysis unit, and in FIG. 20B, where it is employed to protect a boat engine coolant system from biofouling from barnacles or invasive mussels.

FIG. 14A(3), upper diagram, depicts a cross-sectional view of pipe 160, coated with the anti-fouling coating, only now the bilaminar polymer coating comprised of Polymer-I 9 and Polymer-O 3 coats both the inner surface 160A of pipe 160 as well as its outer surface 160B. In this case, the pipe carries water 2A containing cyprids or veligers 165 within its interior and at the same time runs through a body of water 2B also containing cyprids or veligers. Such a situation might occur with an intake water pipe lying at the bottom of a body of water drawing water out of that body of water into a power or desalinization plant (for example pipe 231 in FIG. 20A). In this case, both the interior and exterior surfaces have to be protected from attachment and growth of barnacles and mussels. Larval forms 165 are seen both in the water flowing through the interior of the pipe as well as in the water surrounding the pipe. FIG. 14A(3), lower figure, shows the bilaminar anti-fouling coating in a longitudinal cut-away view showing both the inner and outer surface of the pipe protected from larva contaminated water. All structures in FIG. 14A(3) are the same as in FIG. 14A(1) and FIG. 14A(2) and perform the same function as described for FIG. 14A(1). Arrow 162 of FIG. 14A(3), lower figure, shows the direction of flow of water within the pipe with biofouling larval forms present. In this embodiment pipe 160 is protected from fouling organisms on both its inner and outer surfaces. This embodiment is shown depicted in FIG. 20A, where it is employed to protect both the interior and exterior of the seawater intake tube of the seawater electrolysis unit from barnacles and growth of other organisms.

Figure 14B:
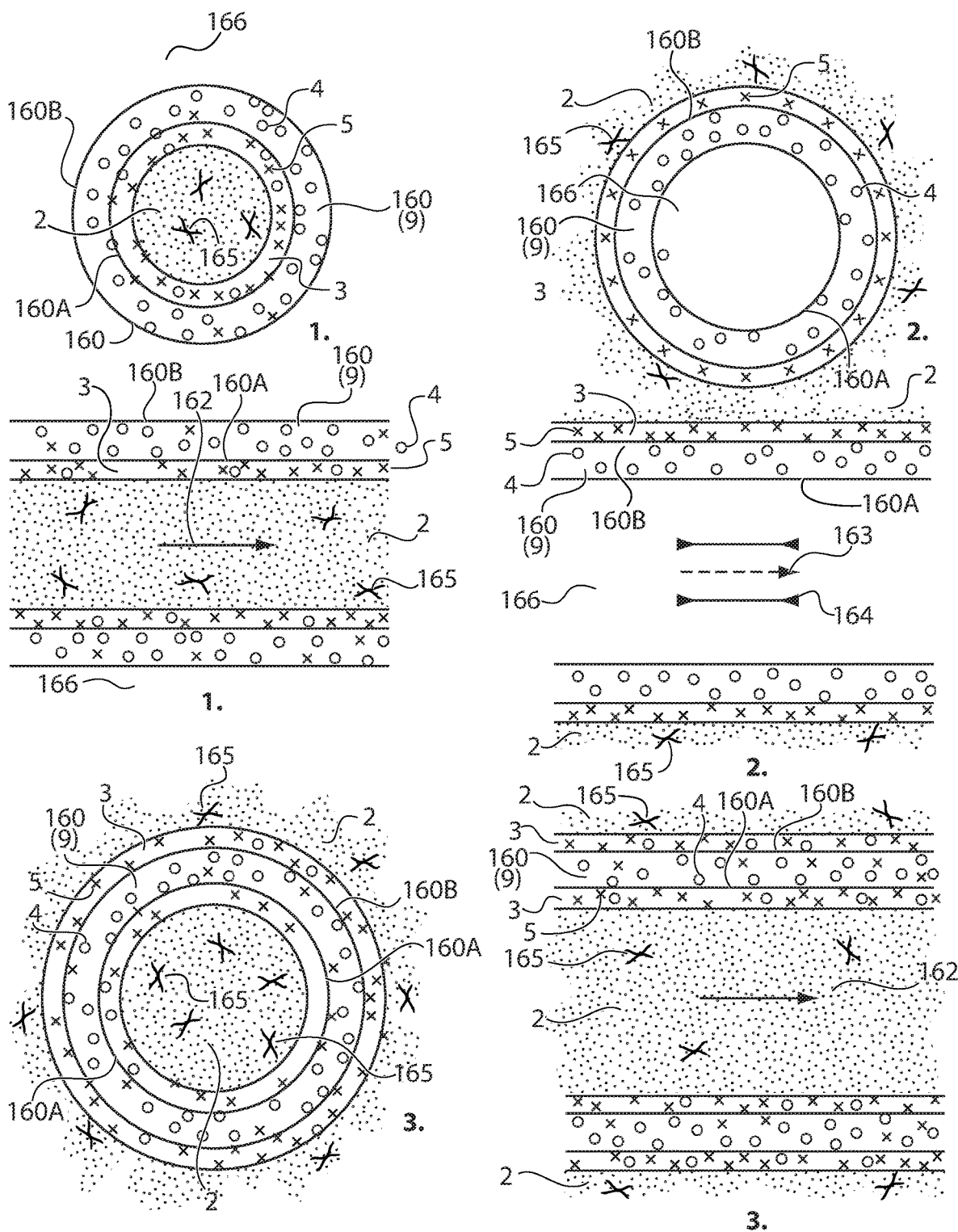
FIG. 14B depicts cross section and side cut-away views of a plastic polymer pipe with impregnated biocide acting as the inner biocidal polymer layer and coated on the outside, or inside, or both with the outer biostatic polymer layer.

FIGS. 14B(1), (2), and (3) represent embodiments of the biofouling protected pipe that are similar to the application embodiments depicted in FIGS. 14A(1), (2), and (3), except that in this structural embodiment, the pipe itself is a plastic polymer, such as polyvinyl chloride (PVC) and itself is impregnated with biocides in the manner depicted in structural embodiments of FIGS. 1A, 5A, 5B, 6A, 6B, 7, 8, and 10A. The pipe itself becomes the inner biocidal Polymer-I layer and its inner surface, outer surface, or both is coated with the biostatic outer Polymer-O layer. Note that the structural embodiment of FIG. 10B can also be used with the outer Polymer-O layer containing biocidal biocides only for enhanced effectiveness in heavily contaminated water. The biocides are added to the plastic polymer pipe at the time of manufacture.

FIG. 14B(1), upper diagram, shows the plastic polymer pipe as 160 (also labeled as 9, the Polymer-I layer) with inner surface 160A and outer surface 160B with inner surface 160A coated by Polymer-O containing a relatively high concentration of biostatic biocide 5 and relatively low concentration of biocidal biocide 4. Plastic polymer pipe 160 is impregnated with a relatively high concentration of biocidal biocide 4 and relatively low concentration of biostatic biocide 5. Area 166 represents the space around the pipe which could be air, non-contaminated water, soil, or some other medium. Contaminated water 2 with floating veliger or cyprid larvae 165 is seen flowing in the direction of arrow 162 labeled on FIG. 14B(1), lower diagram depicting a longitudinal cut-away view of the pipe, with the structures in this lower diagram labeled as per the upper diagram.

FIG. 14B(2) is a similar structural embodiment to FIG. 14B(1) only now, as depicted in the lower diagram, the Polymer-O 3 coating containing the same biocide concentrations as before is covering the outer surface 160B of plastic pipe 160. As before, Polymer-I 9 containing the same biocide concentrations as before represents the same structure as plastic pipe 160. Now contaminated water 2 with veligers or cyprids 165 is seen flowing outside of pipe 160 in no particular direction, while the inside of pipe 160 labeled as 166 might have uncontaminated water, another fluid, or a gas flowing in a direction represented by dotted arrow 163 in FIG. 14B(2), lower diagram, depicting a longitudinal cut-away view of the pipe, or electrical cables or other types of cables represented by double arrow 164 might be present. All other structures labeled in FIG. 14B(2) lower diagram are the same as in the upper diagram.

FIG. 14B(3) is a similar structural embodiment to the previous two structural embodiments only that this embodiment combines the other two in that now the outer biostatic Polymer-O coating 3 covers both the inner surface 160A and outer surface 160B of plastic polymer pipe 160, which is impregnated as before with the same biocides and biocide concentration making pipe 160 again the Polymer-I 9. Contaminated water 2 with veligers or cyprids is flowing in the direction of arrow 162 (labeled on the lower figure depicting the pipe in longitudinal cut-away view) in the interior of the pipe 160. In addition, there is contaminated water 2 containing veliger or cyprids 165 that is flowing in no particular direction. Again all other structures in the lower diagram are labeled as in the upper diagram. In this particular embodiment, the pipe 160 is protected from fouling organisms on both its inner and outer surfaces. The manufacture of the pipe must not involve a stage requiring a temperature above the decomposition point of the biocide that is incorporated within its polymer matrix.

Figure 15A:
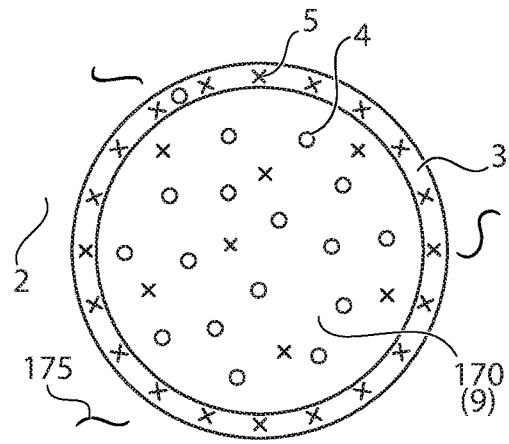
FIG. 15A depicts a cross section cut-away view of a polymer pylon or column impregnated with biocide serving as the inner biocidal polymer layer covered on its surface by the outer biostatic polymer layer.

Continuing with the application embodiments of the present invention, FIG. 15A depicts a cross-sectional view of a plastic pylon. During manufacture, a plastic pylon 170 (9) is formed from a suitable plastic that does not require a temperature in manufacture higher than the decomposition point of the biocides that will be impregnated into the pylon and is impregnated with a biocidal biocide 4 and a lesser amount of biostatic biocide 5. Thus plastic pylon 170 also functions as Polymer-I 9. Pylon 170 is then covered with biostatic Polymer-O 3 containing biostatic biocide 5 in high relative concentration and biocidal biocide 4 in low relative concentration. Cyprid and larval forms, including mussel veligers and barnacle cyprids 175, are seen floating in the aquatic environment 2. This structure would find use in biofouling structures such as piers, docks, bulkheads, platforms, pylons for off shore wind turbines such as structure 146 in FIG. 13C, bridges, causeways and so forth. The polymer in pylon 170 maybe made of any type with sufficient mechanical strength and other physical properties to make it useful to comprise the given structure that is needed.

Figure 15B:
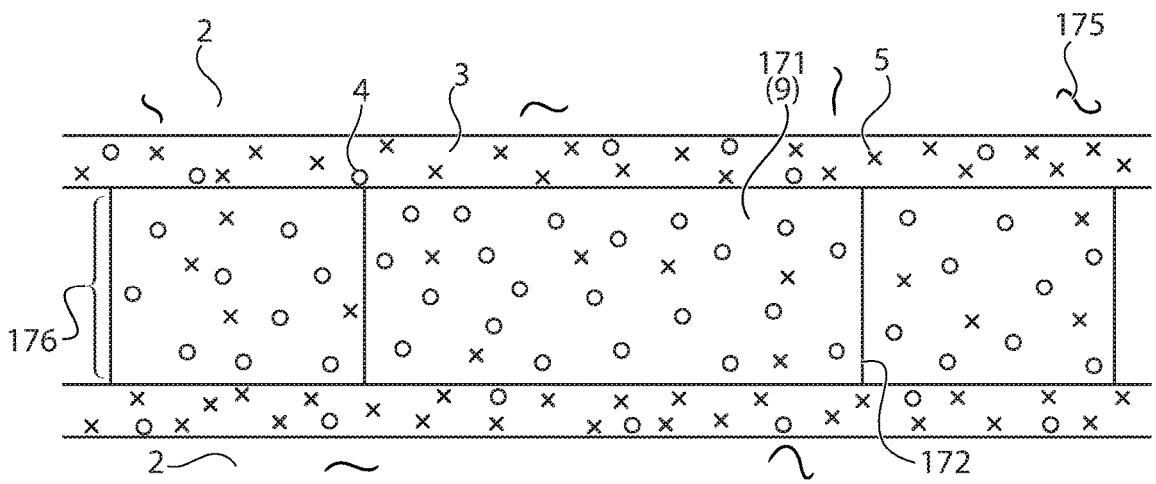
FIG. 15B depicts a cut-away view of a wall comprised of plastic polymer bricks impregnated with biocide serving as the inner biocidal polymer layer covered on its surface by the outer biostatic polymer layer.

FIG. 15B shows a longitudinal cut-away top view of a wall 175 that has varying sized three-dimensional plastic structural bricks or blocks 174 (9) impregnated with biocidal biocide 4 in relative high concentration and biostatic biocide 5 in relative low concentration at the time of manufacture. The interior of the brick functions as the biocidal portion of the coating, equivalent to Polymer-I 9 of the structural embodiments. Polymer-O 3 containing a high relative concentration of biostatic biocide 5 and a low relative concentration of biocidal biocide 4 is coated onto both sides of wall 174 (9) if the wall is surrounded by water, and only one side if the wall is exposed to water on one side. Larval veliger and cyprid forms 175 are seen floating on both sides of the wall in the aquatic environment 2. The polymer in wall 174 may be made of any type with sufficient mechanical strength and other physical properties to make it useful to comprise the given structure that is needed. Appropriate structures that can make use of this embodiment include seawalls, light houses, oil platforms, buildings with foundations exposed to bodies of water, locks, bulk heads, bridge pylons, and so forth.

Figure 15C:
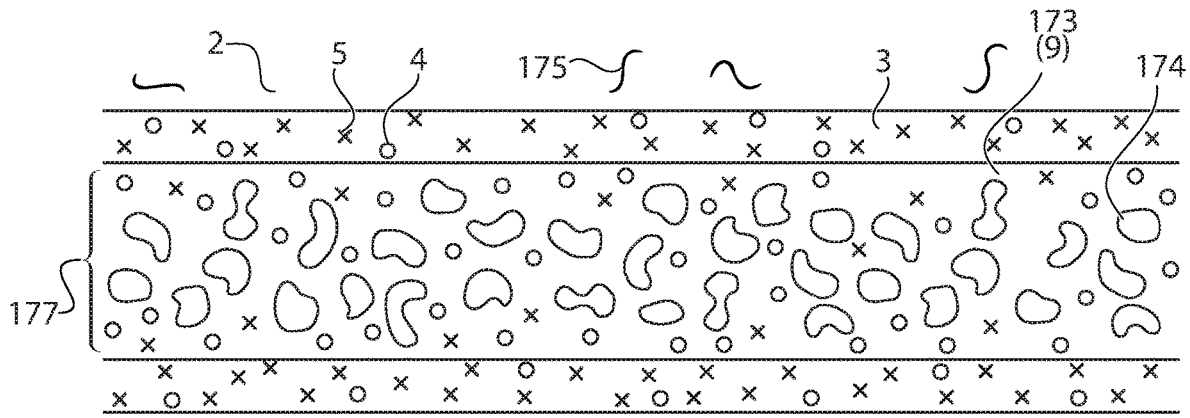
FIG. 15C depicts a cut-away structure comprised of concrete whose inner portions are impregnated with a biocidal biocide impregnated liquid polymer to form an inner biocidal polymer layer and whose outer surfaces are covered with an outer biostatic polymer layer.

FIG. 15C shows a longitudinal cut-way top view of a foundation 177 whose bottom rests on the seabed of a body of water 2 in which cyprid and veliger larval forms are floating. Barnacles and mussels are extremely destructive to cement and concrete structures, causing them to crumble. The wall is comprised of porous cement 173 (9) and gravel 174 so that the structure is considered concrete. A liquid biocidal polymer, Polymer-I 9 is applied to the surfaces of the concrete foundation by painting, rolling, spraying or some other means and is allowed to soak into the outer layer of the concrete. The liquid biocidal polymer is impregnated with a high relative concentration of biocidal biocide 4 and a low relative concentration of biostatic biocide 5. When cured and no longer tacky, a second liquid biostatic polymer, Polymer-O 3 is applied over Polymer-I and this polymer is impregnated with a high relative concentration of a biostatic biocide 5 and a low relative concentration of a biocidal polymer 4.

The result of the sequential application of these two biocide-laden polymers is that the concrete structure and surface has been treated to resist barnacle and mussel implantation, growth, and proliferation. This concrete anti-fouling coating and process is useful for the same structures as listed for the biocide treated blocks and bricks in the description of the preceding embodiment in FIG. 15B. Note that concrete structure 177 would have to be treated while it was being poured and shielded from the sea water while it was setting, or once it was set, it could be painted underwater with an appropriate polymer coating that can be applied underwater.

In the latter case, Polymer-I 9 would not be a polymer that can be absorbed into the concrete but would have to be painted on the surface of the concrete followed by Polymer-O 3. The concrete foundation structure could be in addition to the immersed structures listed above FIG. 15B, as well as concrete boat launching platform ramps to keep these structures free of barnacles or mussels.

If Concrete structure 177 is replaced by a wood structure such as a shipwreck, such a shipwreck which is always of valuable archeological value and suffers the greatest biofouling damage through the boring of its wood by marine woodborers (shipworms, another calcareous calcium forming biofouling organism belonging to the same Mollusca phylum as invasive mussel species), through the use of application of two layers of polymer coating suitable for underwater application such as under water application epoxy polymer coatings and impregnated with the biocides specified above, such threatened historical underwater monuments can be saved from destruction.

Note if low viscosity fluoropolymers are used in both Polymer-I and the Polymer-O layer, then not only can the Polymer-I layer be allowed to soak into the concrete first, but also the Polymer-O layer could next be allowed to soak into the concrete next to produce a concrete surface whose anti-fouling properties change gradually from biostatic at the surface to biocidal deeper down within the concrete due to the changing composition of increasing concentrations of the biocidal biocide and decreasing concentrations of the biostatic biocide with increasing depth of the concrete from the water surface.

As an extra benefit of this arrangement of polymers and biocides, the concrete surface adjacent to the water will be completely waterproof. FIG. 15C shows a Polymer-O layer to be present both above and below the concrete structure's surface which would be necessary if the structure was in a vertical orientation completely surrounded by water. However, the bottom Polymer-O layer would be omitted if the concrete's bottom structure rested horizontally on the sea floor.

An exemplary stretchable rubber polymer is ethylene-propylene-diene-monomer (EPDM), a non-plastic rubber polymer that is deformable, with a modulus of elongation of about 200% to about 300%, which means it can be stretched 200 to 300% before it breaks. EPDM has an operational life time in both freshwater and marine bodies of water of up to 25 years. For that reason it is used to waterproof rooftops, with a life expectancy of up to 50 years, and to line ponds and pools, with a life expectancy of operation of up to 25 years. Like fluoropolymers, this stretchable, flexible, non-plastic polymer is UV resistant. Its use allows extension of the properties and benefits of this invention to flexible and semi-rigid surfaces and structures. Any non-plastic polymer possessing the mechanical, optical, and chemical properties of EPDM, especially of the synthetic rubber family, is useable as a composition for the anti-fouling coating of this invention. Also, EPDM can be used as a Polymer-O layer topcoat on top of another type of polymer that is used in the Polymer-I layer bottom coat with or without a polymer primer depending upon the nature of the polymer in the Polymer-I layer.

Figure 16A:
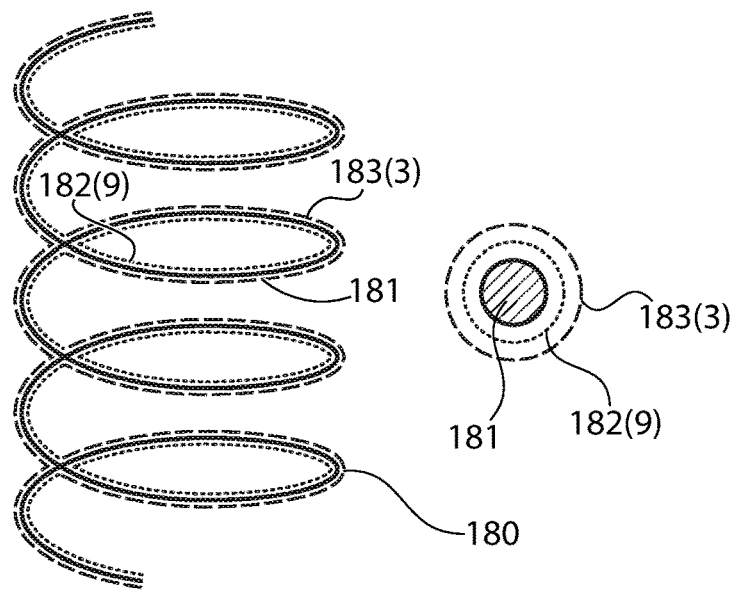
FIG. 16A depicts a spring coated with an inner biocidal polymer layer and an outer biostatic polymer layer.

FIG. 16A is an embodiment of the anti-fouling coating showing an extension spring coated with a bilaminar polymer coating whose cross-section is blown up in the adjacent inset drawing. Spring 181, is shown to be an extension spring, but which may be a compression spring or any other type of spring, may be formed of an exemplary material such as 17/7 stainless steel, noted for its tremendous resistance to metal fatigue, but any appropriate spring material may be selected including, e.g., stainless steel, spring steel, music wire, brass, titanium, and so forth, as well as plastics such as nylon.

Coated onto the spring is an inner biocidal layer of liquid EPDM 182 (9) that functions as a Polymer-I layer 9, impregnated with a relatively high concentration of biocidal biocide and a relatively low concentration of biostatic biocide, upon which a second layer of liquid EPDM 183 (3) functioning as a Polymer-O layer 3 is coated and which is impregnated with a relatively high concentration of a biostatic biocide and a relatively low concentration of a biocidal biocide. The spring may extend and compress, and as long as the maximal extension of the spring does not exceed about 200 to about 300% of its original length, the EPDM will remain intact, affording anti-fouling protection to moving springs submerged in water.

Figure 20A:
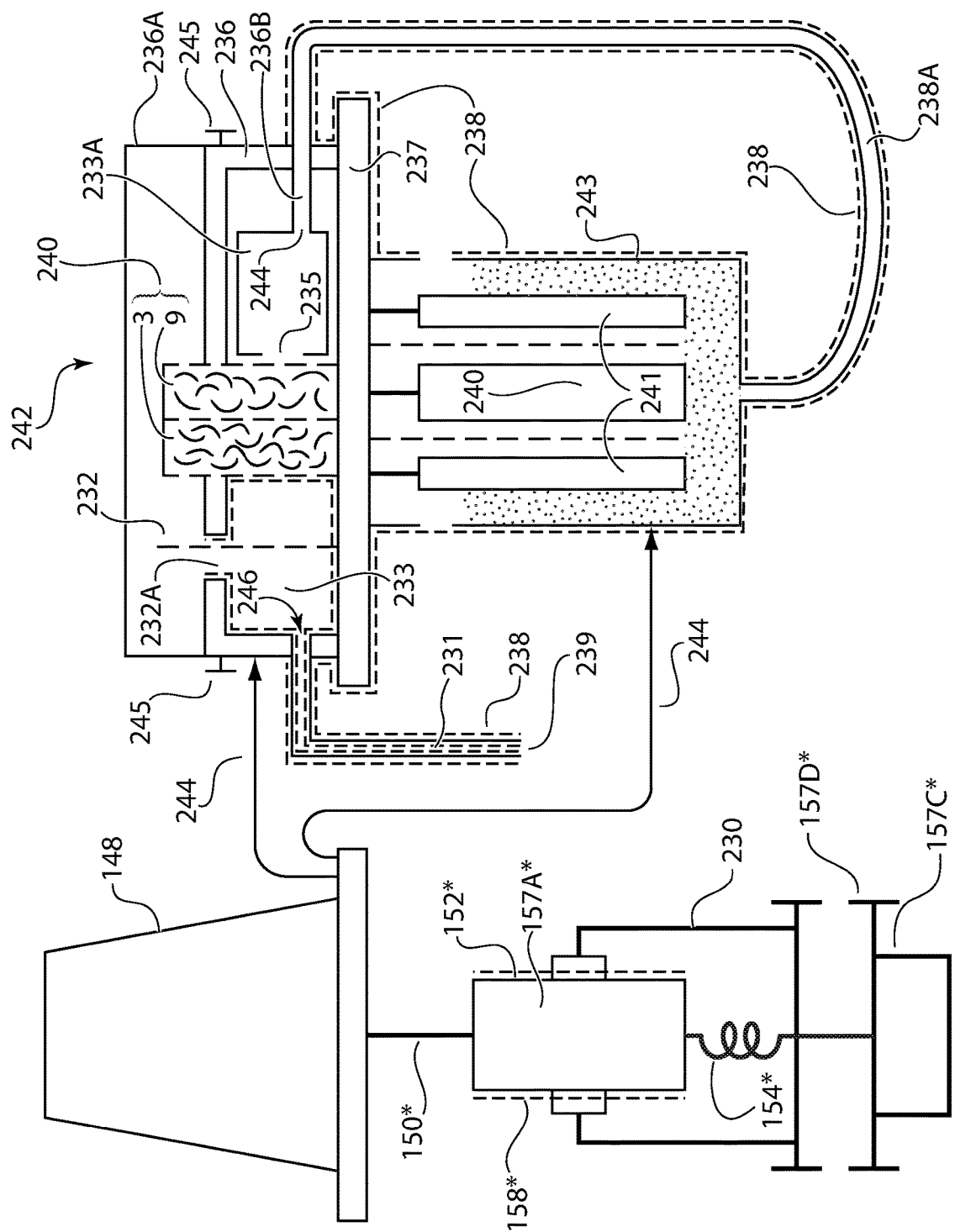
FIG. 20A depicts a schematic and cut-away view of a wave energy converter coupled to a floating sea water electrolysis unit via electrical cables and a water intake filter having a first outer biostatic layer of filter media coated with a polymer impregnated with a biostatic biocide and a second inner biocidal layer of filter media coated with a polymer impregnated with a biocidal biocide.

This is particularly valuable to wave energy converters producing electricity from the mechanical motion of waves, such as illustrated in the combined off-shore wind wave energy farm of FIGS. 13C and 20A, in which moving springs are often essential in transmitting the mechanical energy pulse from the wave and float into the rotor of the generator. Biofouling of a spring will render it inoperative in a short period of time followed by rupture, and this described embodiment of the present invention is capable of preventing barnacles and invasive mussels from attaching to springs, interfering with their movement, function, and the function of the equipment of which they are a part, and eventually destroying them as well as the equipment that they are a part of.

Figure 16B:
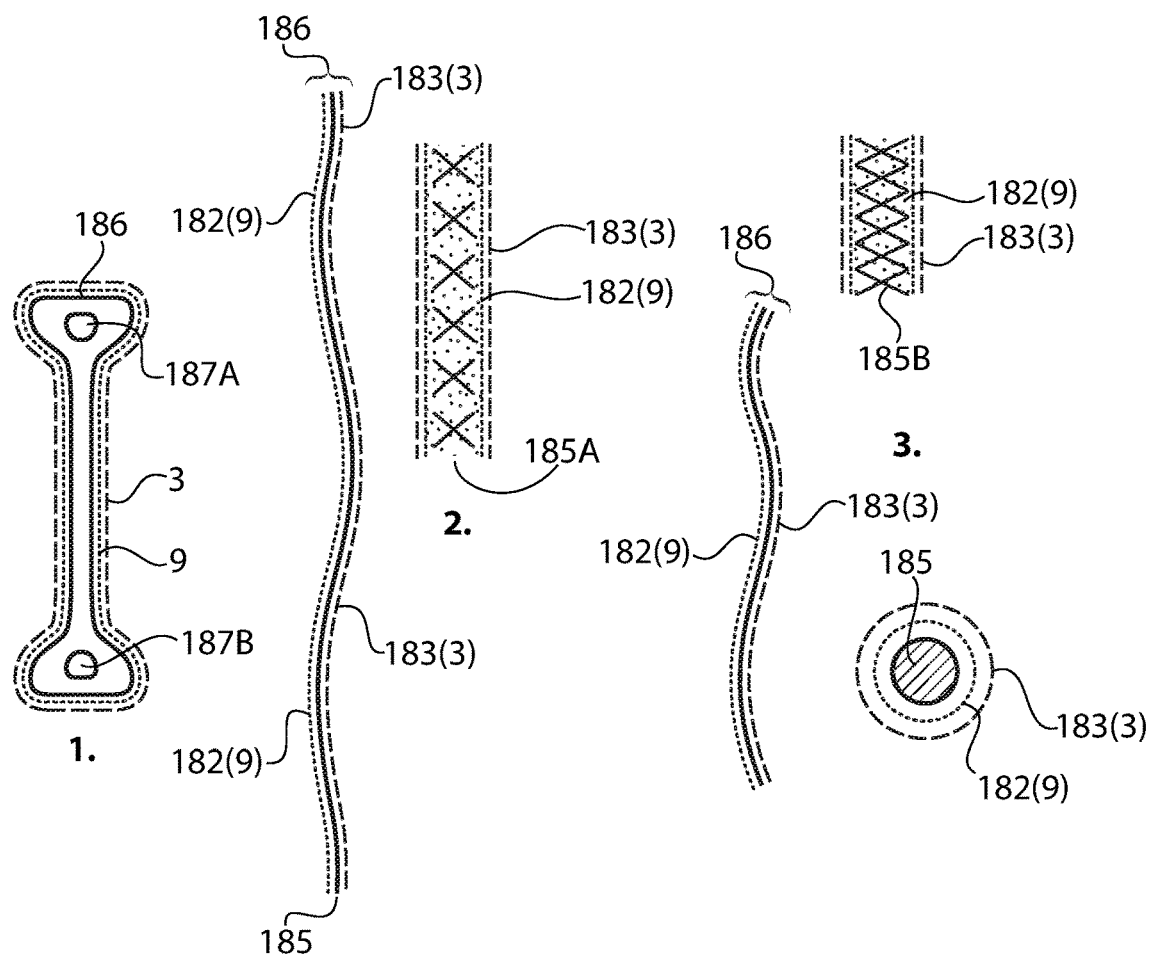
FIG. 16B depicts a flexible, stretchable bungee cord coated with an inner biocidal polymer layer and an outer biocidal polymer layer.

FIG. 16B depicts another embodiment of the anti-fouling coating showing an extensible cable, known as an anchor line, that can change its length when a tension force is applied to it and restores its original length when the tension force is removed. Also known as a bungee cord, a major use for such a structure is for anchoring leisure boats and allowing the boat to oscillate both horizontally and vertically with waves, tides, and currents. Such cables are useful if the boat is exposed to very bad weather and large waves, preventing the mooring lines from being snapped and the boat being damaged. Most conventional extension cables rupture from various reasons—exposure to salt water, UV deterioration, barnacles and mussels. Mussels have a particularly high predilection for cables and woven fabric lines.

These structures are usually composed of a core of long stretchable rubber fiber lines that have none of the durable properties of EPDM, surrounded by a woven fabric of some type, usually nylon. They usually can double their length on stretching but never last more than one season before the rubber fiber lines snap or lose their stretchable property. They come in lengths up to several meters.

Another type of stretchable boating device for boat docking is the snubber, usually made out of polyurethane rubber. A snubber is about 12" to about 24" long and is capable of being stretched to about 1.5 times its resting length. They are used to absorb the rocking motion of the boat that normally would otherwise cause significant friction of the docking lines against the dock causing the lines eventually to fray and snap.

The anchor line is usually very problematical with biofouling because it is always in the water and the anchor line cannot stretch with a large biomass of mussels or barnacles attached, which often causes premature rupture of the lines. Biofouling less of a problem with snubbers, because they are above the water line, but they can be contaminated with veligers in freshwater lakes and spread the invasive mussels. The anti-fouling coating of the present invention allows the enablement of a significant improvement in these structures.

The snubber is simply coated with the same two layers of biocide impregnated EPDM Polymer-O layer 3 and Polymer-I layer 9 respectively as was the case with the springs, and this embodiment is shown as FIG. 16B(1) as snubber 186, with dock line tie holes 187A and 187B at each end, with the dock end of the dock line (not shown) wrapped first around the upper tie hole 187A, then around the central section 187C, and then around the lower tie hole 187B before proceeding to the boat. When the rocking motion pulls the boat away from the dock, the snubber stretches stretching the line wrapped around it, absorbing the rocking motion away from the dock and decreasing its amplitude.

The stretchable anchor line 186 is shown in its stretched state in FIG. 16B(2) and in its contracted state in FIG. 16B(3). Anchor line 186 is coated with or impregnated with a bilaminar EPDM biocide-impregnated coating having outer biostatic EPDM polymer coating, Polymer-O 183(3), that covers an inner biocidal EPDM polymer coating, Polymer-O 182(9) containing the same biocide structural composition as the spring in FIG. 16A. Anchor line 186 is composed of a stretchable woven fiber matrix 185A and 185B.

FIG. 16B(2) shows the anchor line stretched by wave action or the tidal elevation as it is normally connected between the boat and the anchor, which is fixed in position at the seabed or riverbed. The woven fabric fiber strands 185A is stretched apart as compared to the woven fabric fibers 185B that are now significantly closer as the passage of the wave or the tidal elevation allows the restoring force of the stretched EPDM polymer layers to restore the anchor line 186 to its passive rest position shown in FIG. 16B(3).

When the stretchable anchor line is in its stretched state in FIG. 16B(2), the weavings of the woven fabric fibers are shown stretched and separated as fibers 185A. When the anchor line is in its contracted resting state, the woven fabric fibers are shown closer together as fibers 185B. Hence the bilaminar EPDM layer not only provides the anti-fouling properties to the anchor line, but it acts like a stretched spring that releases its energy as a restoring force to return the anchor line to its rest length. The fiber provides the tensile strength to the line, and the anti-fouling bilaminar EPDM coating provides the stretching and restoring force to the anchor line. When the bungee cord or anchor line is in its stretched position, the space between the crisscrossed fibers of the anchor line's core are expanded, and when the anchor line is in its rest relaxed state, the space between the crisscrossed fibers of the anchor line's core is compressed.

The anchor line can be extended to at twice its rest length but safely less than three times its rest length because of the presence of the bilaminar EPDM coating having an elongation modulus of about 200% to about 300%. The Polymer-I EPDM layer fully saturates the inner woven fiber network 185. Without its presence, while the inner woven fiber network can be stretched as a result of a wave, there would be no restoring force to bring the anchor line back to its rest state. The anchor line can also be considered to be a combination of long rubber band and a rope, where the rubber band possesses the anti-fouling properties that keep the anchor line from assembling a bio-mass of barnacles or mussels.

Furthermore, when the anchor line 186 is constructed in conformance with the specifications of this invention, the central woven fiber network cannot only be made out of typical rope fiber strands like polyethylene, polystyrene, or nylon, but it can also be made out of woven aramide fiber, high molecular weight polyethylene (HMWPE), carbon fiber, stainless steel fiber, and other extremely high tensile strength materials giving these anchor "bungee" lines tremendous tensile strength before breaking. This in turn allows these anchor lines to be quite long, with a length up to many meters. The advantages to the leisure boating industry are significant and three-fold: biofouling of anchor lines is eliminated, the need to replace anchor lines yearly is also eliminated, and boats can be secured over wide ranges of changes in water levels including what is observed in storm surges and hurricanes.

Figure 17A:
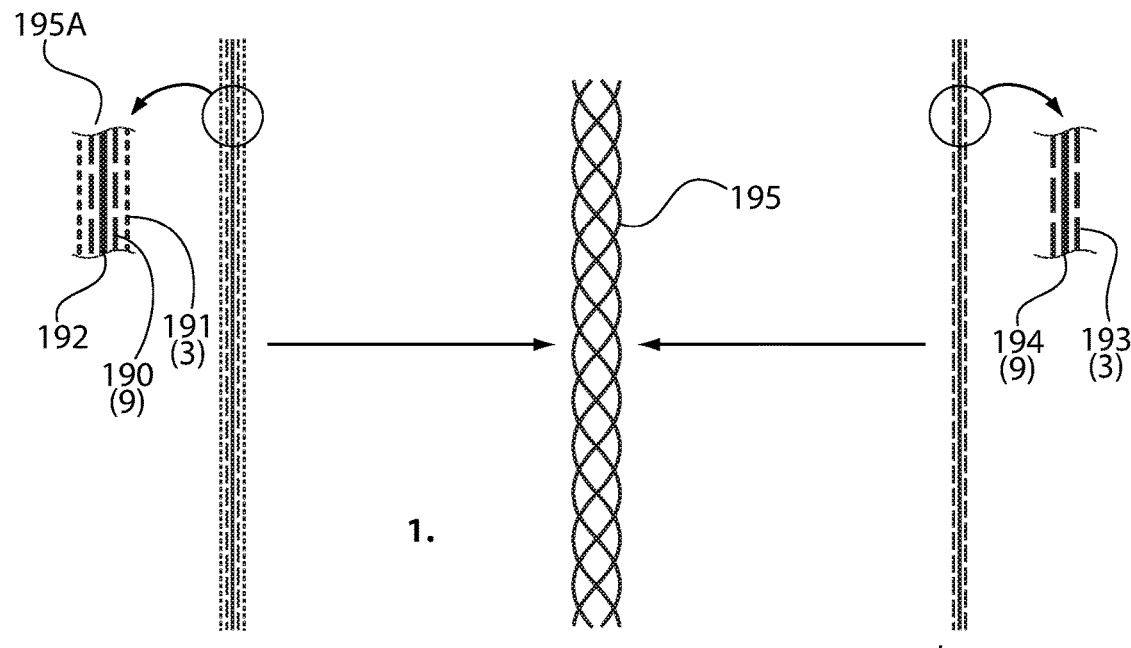
FIG. 17A depicts a fiber coated with an inner biocidal polymer layer and an outer biostatic polymer layer, a fiber impregnated with a biocide to function as an inner biocidal polymer layer, a rope made with such fiber that would be protected from invertebrate biofouling attachment.

FIG. 17A depicts another application of the anti-fouling coating of this invention which is a generalization of the application of FIG. 16B that gives any rope or cable, stretchable or not, anti-fouling properties. FIG. 17A(1) shows a twisted rope composed of strands of fiber of metal, aramide fiber, carbon fiber, or plastic such as nylon, polyethylene, polypropylene, or HMWPE as well as natural fiber like hemp, wool, or cotton, as well as natural polymers such as rubber that are twisted together to form a rope.

If they the rope is of a non-plastic material, as is depicted in FIG. 17A(2) where in the inset picture, rope fiber strand 195A is covered and impregnated first with an outer stretchable EPDM biostatic Polymer-O layer 191 (3) if the rope is stretchable, or with a non-stretchable fluoropolymer polymer or other plastic polymer with a non-stretchable rope. In either case, the polymer of the Polymer-O layer is impregnated with a relatively high concentration of biostatic biocide and a relatively low concentration of biocidal biocide.

Polymer-O is covers a Polymer-I biocidal layer 190 (9) composed of a stretchable EPDM biocidal layer if the rope is stretchable or with a non-stretchable fluoropolymer or other plastic polymer with a non-stretchable rope. In either case, Polymer-I is impregnated with a relatively high concentration of biocidal biocide and a relatively low concentration of biostatic polymer.

If the rope is stretchable, the rope fibers would have to be comprised of a stretchable polymer such as a rubber polymer, or the rope fibers would have to be woven in a crisscross manner as depicted in FIG. 16B allowing such stretch with applied tension. The spacing between the crisscrossed strands of the stretchable rope would alternately expand and contract, but this does not happen for a non-stretchable rope. FIG. 17A(3) depicts another rope where the inner biocidal Polymer-I layer, labeled 194 (9), is the rope fiber itself. If the rope fiber is a plastic polymer, then at the time of manufacture, it can be impregnated with a relatively high concentration of biocidal biocide and a relatively low concentration of biostatic biocide. In turn it is covered by a biostatic Polymer-O 193 (3) layer comprised of a stretchable rubber polymer such as EPDM if the rope is stretchable or a non-stretchable fluoropolymer or other plastic polymer with a non-stretchable rope. In either case Polymer-O is impregnated with a high relative concentration of biostatic biocide and a low relative concentration of biocidal biocide.

Again if the rope is stretchable, the rope fibers' plastic polymer would have to be stretchable or the rope fibers would have to be woven in a crisscross manner as depicted in FIG. 16B, allowing such stretch with applied tension. It is clearly evident that such single-plastic polymer fibers, impregnated with biocides so that the fibers themselves are biocidal to biofouling organisms, constitute the inner Polymer-I layer and can be coated with a biostatic outer polymer layer. If the fibers themselves are not impregnated with biocides so that the fiber is coated by both the inner biocidal Polymer-I and outer biostatic Polymer-O coatings, in either case, they can be woven into thin threads, which can in turn be woven into biofouling resistant fabrics and fine netting materials or they can be woven into complex and thick ropes and cables, which in turn can be woven into coarse nets and other flexible structures.

In all of the present embodiments, any structure that has a dual function of also being a Polymer-O outer biostatic polymer anti-fouling layer will be labeled with a second (3) label in addition to the primary structure label, and any structure that has a dual function of also being a Polymer-I inner biocidal polymer anti-fouling layer will be labeled with a second (9) label in addition to the primary structure label. It is also to be pointed out that the plastic polymer, such as the preferred fluoropolymer including flouroure-thanes and FEVE and related fluoropolymers, as well as non-fluorinated plastic polymers, may be interchanged with EPDM and similar stretchable and flexible non-plastic rubber polymers. It is also to be noted that the use of EPDM coatings gives the anti-fouling coating an extended multiple year operating life that would be as long as 5 years and more probable in excess of 10 years, which is similar to the extended operating life afforded to the anti-fouling coating of this invention by the use of fluoropolymers such as flourourethanes, FEVE, and similar such fluorinated compounds.

Figure 17B:
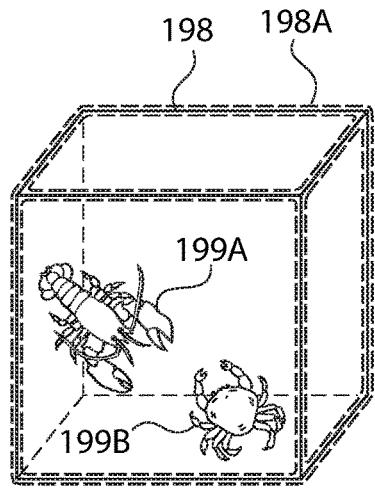
FIG. 17B depicts a lobster trap coated with an antifouling coating comprised of an inner biocidal polymer layer and an outer biostatic polymer layer.

FIG. 17B depicts a lobster or crab trap 198 with a lobster 199A or crab 199B contained within it. Trap 198 is coated with an inner Polymer-I biocidal polymer layer and an outer Polymer-O biostatic polymer layer as previously described for FIG. 17A. The combined bilaminar polymer layer comprising Polymer-I and Polymer-O is labeled as 198A. As in the case of the rope of FIG. 17A, if the lobster or crab trap 198, which is considered to be a rigid or semi-rigid structure with the possibility of some inherent flexibility in its structure, is comprised of plastic, that plastic can be impregnated with the biocides in a mixture so that its composition is that for a Polymer-I layer, and thus the lobster or crab trap itself with function as a biocidal Polymer-I layer.

Because structure 198 is either rigid or semi-rigid, any of the polymers mentioned in this disclosure, whether the polymer is stretchable such as the preferred stretchable polymer EPDM or not such as the preferred fluorinated polymers, would be useful in the anti-fouling coating for this structure specified by this invention. The present embodiments thus prevent damage to the traps from biofouling. Further, because crabs, lobsters, and shrimps are also crustaceans, it is important that the more potent biocidal biocides are water insoluble and contained within the inner biocidal layer so that these more potentially hazardous biocides do not affect the lobsters or crabs within the traps, either by killing them or by allowing these biocides to enter the human food chain when these crustaceans are eaten by humans.

The benefits of this application embodiment can be extended to the large polygonal frame-like structures used in aquacultural fish farms, another type of submerged structure plagued by barnacle and mussel biofouling, of which the only practical solution was to have their frames painted with copper based paints or the frames made out of pure copper that are not environmentally friendly to the fish inside the aquafarming structures and in the case of the pure copper, quite costly, or have the frames made out of cupro-nickel alloy which would again be quite costly. The netting strung around the frames that confine the fish in aquafarming structures can thereby also be given antifouling properties by this invention.

Figure 17C:
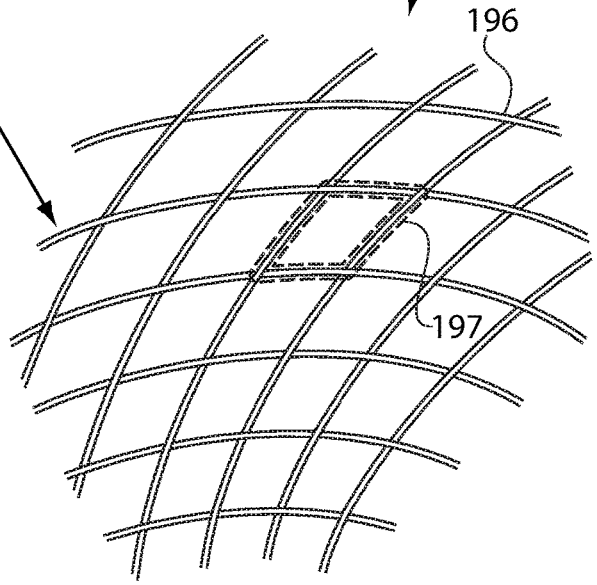
FIG. 17C depicts a fishnet coated with an antifouling coating comprised of an inner biocidal polymer layer and an outer biostatic layer or if the fiber is impregnated with a biocide functioning as an inner biocidal polymer layer, it is then coated with just an outer biocidal polymer layer.

FIG. 17C extends the benefits of the anti-fouling coating of this invention just enumerated for lobster and crab traps to the submerged structural surface known as fish nets. Fish net 196 is shown, and this structure is considered to be highly flexible and requires some degree of being able to be stretched. It is shown coated with the same bilaminar anti-fouling coating of the current invention as described in FIGS. 17A and B. The fishnet can be made out of any of the fibers listed under the structural application for anti-fouling coated rope described in FIG. 17A. If the fishnet is composed of a plastic or non-plastic polymer, the biocidal composition of Polymer-I can be impregnated into the polymer comprising the fish net at the time of manufacture so that the fishnet itself becomes Polymer-I and would then have the biocidal and polymer composition of Polymer-O applied to the fishnet to complete the anti-fouling coating of this invention.

Since the stretching capability of a fishnet would not be needed to be nearly as much as a stretchable rope or anchor line, any reasonably flexible polymer, plastic or non-plastic, would be useable in this application. In some cases, "fishnet"-like structures may be completely rigid, such as intake grates and filters for power inlet pipes for power, water, and desalinization plants, or for sea water intake strainers on boats and ships to filter sea water for the vessel's plumbing and engine cooling system and such structures would find benefit having the anti-fouling coating of the present invention applied to them. Flexible polymer anti-fouling versions of the present embodiments, however, would not be needed for these rigid porous structures. This embodiment of the invention comprising fish nets with intrinsic antifouling properties would be most useful for large commercially deployed fishnets with extended periods of biofouling exposure and for aquaculture polygonal containment structures.

Figure 17D:
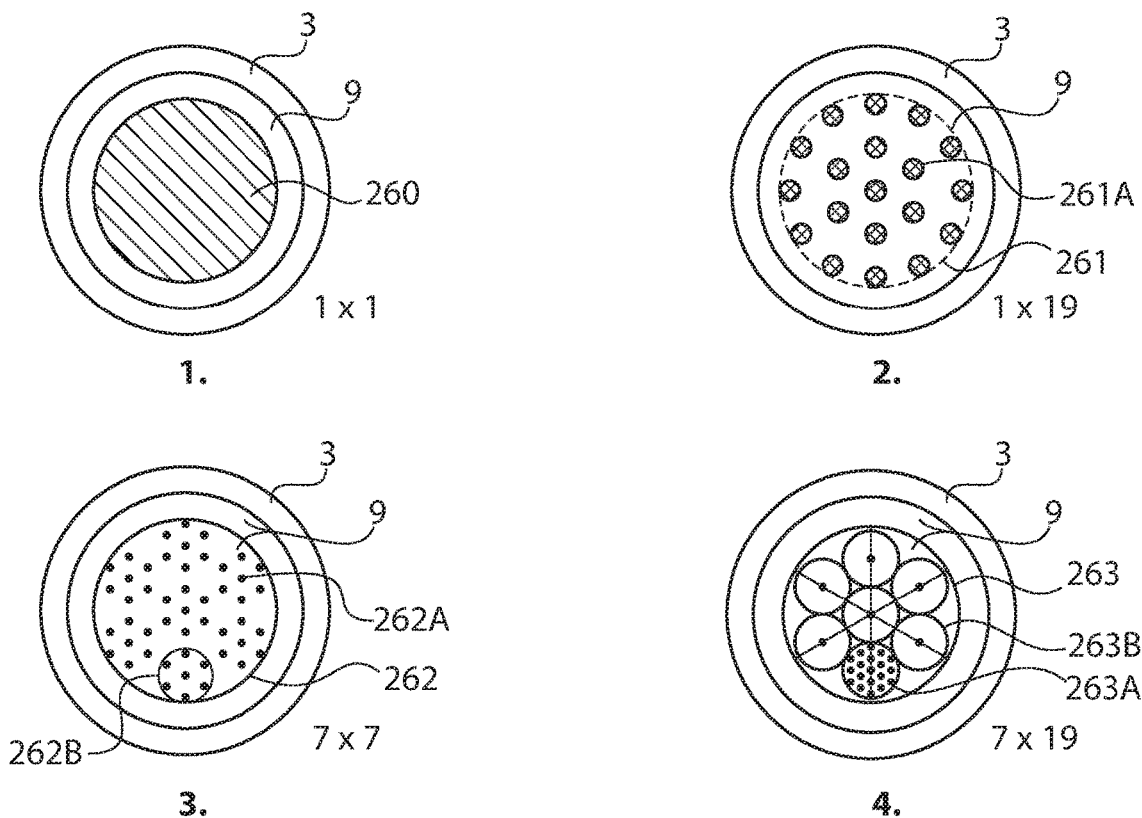
FIG. 17D depicts rigid stainless steel cable with various woven cable configurations within a polymer jacket including a 1×1 central metal cable, a 1×19 woven central metal cable, a 7×7 woven central metal cable, and a 7×19 woven central metal cable, each surrounded by and impregnated with an inner biocidal polymer layer that contains biocides relevant to this invention incorporated into the polymer at the time of manufacture, and this inner biocidal polymer layer in turn is covered by an outer biostatic polymer layer.

FIGS. 17D (1)-(4) show additional modifications of cables, this time rigid cables, to protect such cable structures against deposition of biofouling organisms. FIG. 17D(1) depicts a cross-section of a single metal cable 260 (in a 1×1 woven configuration) covered by an inner biocidal Polymer-I layer 9, which in turn is covered by an outer biostatic Polymer-O layer 3.

FIG. 17D(2) depicts a cross-section of a cable whose internal metal structure 261 is woven into a bundle of 19 single strand cables 261A, which is a standard 1×19 cable configuration, and this central woven bundle of single strand cables is surrounded by and impregnated with an inner biocidal Polymer-I layer 9 which is in turn covered by an outer biostatic Polymer-O layer 3.

FIG. 17D(3) depicts a cross-section of a cable whose internal metal structure 262 is woven into a bundle of 7 sub-bundles 262B, each having 7 metal strands 262A, a standard 7×7 cable configuration, and this central woven bundle of single strand cables is surrounded by and impregnated with an inner biocidal Polymer-I layer 9, which is in turn covered by an outer biostatic Polymer-O layer 3.

FIG. 17D(4) depicts a cross-section of a cable whose internal metal structure 263 is woven into a bundle of 7 sub-bundles 263B, each having 19 metal strands 263A, a standard 7×19 cable configuration, and this central woven bundle is surrounded by and impregnated with an inner biocidal Polymer-I layer 9, which is in turn covered by an outer biostatic Polymer-O layer 3.

The biocidal biocides can be introduced into the polymer surrounding and infiltrating the metal strands at the time of cable manufacture so that the inner biocidal Polymer-I layer is an integral part of the cable which is then subsequently coated with an outer Polymer-O coating as shown on FIG. 17D(2)-(4), or the cable can be manufactured, jacketed in and impregnated by a polymer without biocides, and then subsequently coated first with an inner biocidal Polymer-I layer and then coated with an outer biostatic Polymer-O layer.

Alternatively, the cable may be manufactured as is more customary as an uncoated metal cable, to which first a Polymer-I layer and then a Polymer-O layer may be applied. The stainless steel inner cable core can be substituted with any other metal of high tensile strength. As a representative very common commercially available example of such a cable is a polyvinyl chloride polymer (PVC) coated and impregnated 316 stainless steel cable in a 7×7 or 7×19 configuration. This PVC coating can be impregnated with biocides to give it a biocidal nature at the time of manufacture and then subsequently the cable is coated with an outer Polymer-O layer of a biostatic nature, or the PVC may not have any biocides added to it at the time of manufacture, and a Polymer-I and then a Polymer-O layer may then subsequently in turn coated onto the cable.

Figure 17E:
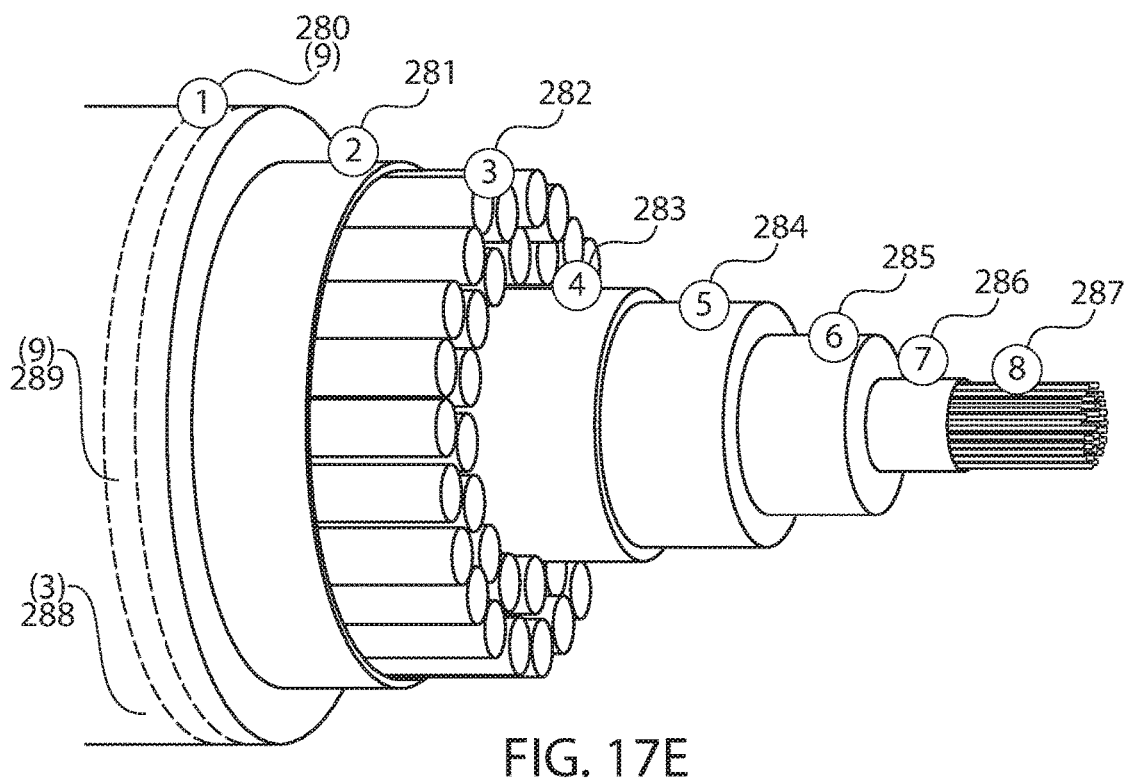
FIG. 17E depicts an undersea submarine cable jacketed by multiple structural layers around the central information-carrying optical cables, with an outer jacket of polyethylene which can be impregnated with an inner biocidal polymer layer and in turn covered by an outer biocidal layer at the time of manufacture.

In any of these configurations, the outer cable surface will remain free of barnacle or invasive mussel attachment by the outer Polymer-O biostatic layer, and if an occasional biofouling organism manages to attach, as soon as the inner Polymer-I layer is breached, the organism will be killed on contact maintaining the integrity of and the tensile strength of the metal cable core itself. Another extremely useful embodiment of such an anti-fouling cable would use a Primer-I zinc-rich polymer primer on the surface of a single strand or woven stainless steel cable, such as in FIGS. 17D(1) and 17D(2)-(4) respectively, rather than impregnating the steel cable core with the Polymer-I biocidal layer. Instead, the zinc rich polymer primer would permeate the steel cable core and would provide extreme adhesion for the inner Polymer-I layer placed on top of it, followed by the Polymer-O layer, to produce a biocide impregnated fouling protected coating and cable of extreme strength and durability. If the polymer of the Polymer-O and Polymer-I layers both were comprised of a low friction fluoropolymer such as PFTE, flourourethane, FEVE, silicone or other low friction polymer, one would have a cable possessing extremely low frictional resistance, extremely long term anti-fouling resistance, and if fluoropolymers are used, UV resistance and exceptional durability and protection from cable failure even in sea water that can last many years FIG. 17E shows yet another cable embodiment of the present invention. Depicted in cross-section is a typical undersea submarine cable used for transmitting data signals via optical fibers (shown) or electricity via copper or aluminum cables (not shown). When these cables travel along the ocean or a large deep lake floor, the distance beneath the water is so great that there is very little plankton at these levels because of the lack of sunlight and photosynthesis, and for that reason barnacles and mussels that require plankton for nutrition are not seen at these depths. However, as these cables begin to come ashore, beginning at about 500 feet for *quagga* mussels in fresh water and at lesser depths for barnacles in salt water and zebra mussels in freshwater, biofouling of these cables endangers cable integrity, and loss of cable integrity has catastrophic implications.

Starting from the center of the cable, optical fibers 287 (or electric cables), petroleum jelly barrier 286, copper or aluminum tube 285, polycarbonate tube 284, aluminum water barrier 283, stranded steel wires 282, Mylar tape 281, and finally outer polyethylene sheathing 280(9) are shown. It is outer polyethylene sheathing 280(9) that can be impregnated with biocides at the time of manufacture to give this sheathing the characteristics of an inner biocidal Polymer-I coating representative of the current invention, which can then be coated with an outer biostatic Polymer-O coating 288(3).

Alternatively, outer polyethylene sheathing 280(9) can be placed onto the surface of the cable in the conventional way without impregnated biocides, and then the Polymer-I layer 289(9) can be deposited on top of the polyethylene layer, and the Polymer-O layer 288(3) can be placed on top of the Polymer-I layer as specified by this invention. The double labeling of polyethylene sheathing 280(9), inner Polymer-I layer 289(9), and outer Polymer-O layer 288(3) indicate the dual roles of these structures within the cable, both as structural components of the cable, as well as functional biocide impregnated layers composing the present invention coated onto the cable, with the designation (3) referring to the outer bio static Polymer-O function of structure 288, and with the designation (9) referring to the biocidal Polymer-I function of either the biocide impregnated polyethylene sheathing 280 if used, or the inner Polymer-I layer 289 that is used if the polyethylene sheathing is not impregnated with biocides. In all of these possible configurations, attachment of biofouling organisms by the Polymer-O layer is again inhibited, and if a few do managed to attach, they are killed on contact upon piercing the boundary of the Polymer-I layer keeping the integrity of the undersea cable intact.

Figure 18A:
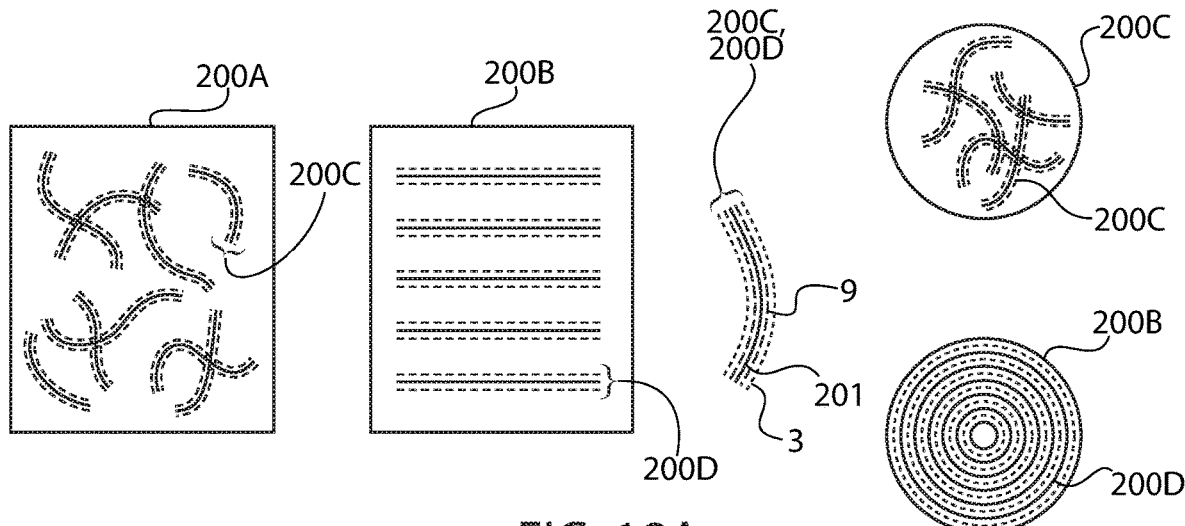
FIG. 18A depicts side-view and cross-sectional cut-away of both a honey comb and a linear sleeve filter whose filter media is coated with an antifouling coating comprised of an inner biocidal polymer layer and outer biostatic polymer layer.

The use of the current invention for rigid "fish-net" like structures can be extended even further to the enablement of special-purpose filters with anti-fouling properties. FIG. 18A extends the use of the anti-fouling coating of this invention to enable the construction of anti-fouling filters as depicted cut-away side views of filter structure 200A, showing a honeycombed biocide polymer coated lattice filter media network 200C, and also of with filter structure 200B, showing a longitudinal slot-like biocide polymer-coated lattice filter network 200D such as used in accordion-like filters.

Filters 200A and 200B are also shown in cross-sectional view as well along with an enlarged view of the coated filter matrix labeled as 200C, 200D. 200C and 200D represent the filter matrix of the honeycomb filter and the longitudinal slot filter respectively that are coated with the inner biocidal Polymer-I 9 layer and the outer biostatic Polymer-O 3 layer. The filter matrix substrate 201 in each case can be made up of matrix materials including ceramics, metal, plastics, cellulose and various forms of fiber and would be coated with a biocidal Polymer-I 9 inner polymer that would coat the filter matrix elements and in turn, be coated with a biostatic Polymer-O 3 outer polymer layer according to the specifications for the Polymer-I and Polymer-O layers delineated repeatedly to this point.

The filter is placed where it can easily be changed for simple maintenance. While a filter without an anti-fouling mechanism incorporated within it may mechanically remove larvae from the water passing through, once lodged in the filter, within 3 weeks the barnacles and mussels will have grown and quickly begin to biofoul the filter, eventually rendering it non-functional and clogging the fluid flow channel that is being filtered. If the filter matrix is a polymer, it may incorporate the biocides required for functioning as a Polymer-I layer which would be added at the time of manufacture and the filter matrix would then only need to be coated with the Polymer-O layer.

Figures 18B, 18C:
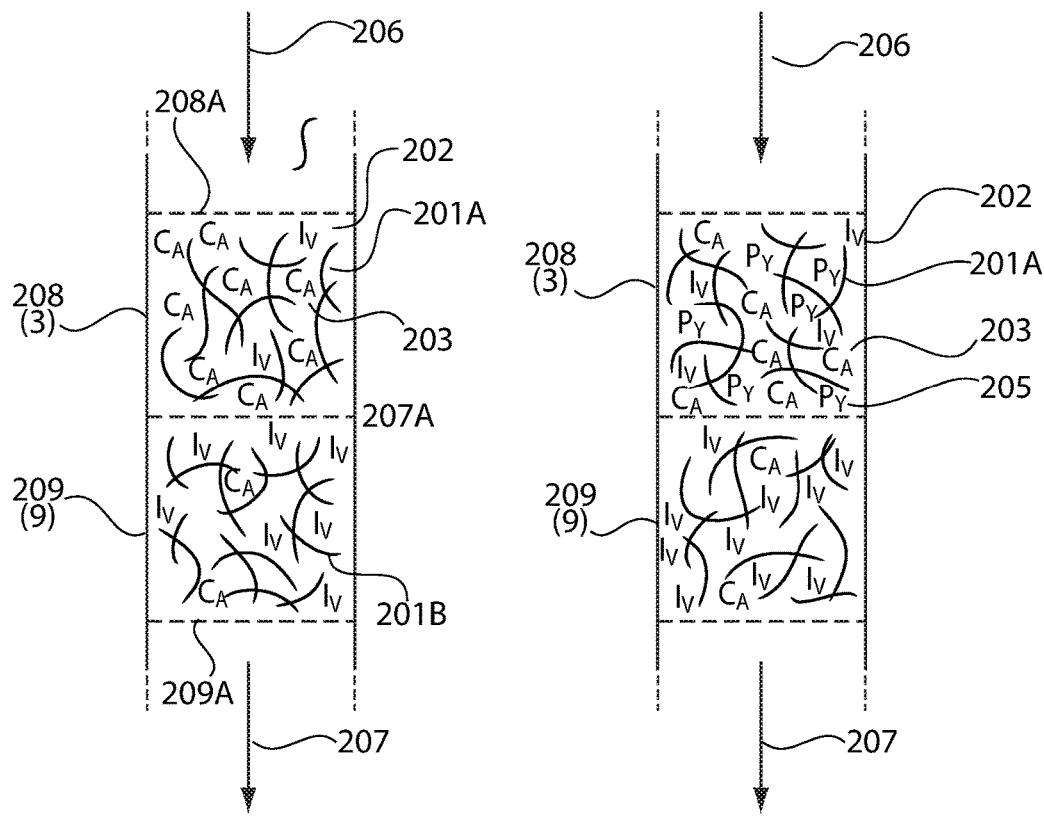
FIG. 18B depicts a side view of a two layer filter having an upper first layer of filter media coated with an outer biostatic polymer layer containing a high concentration of the biostatic biocide capsaicin and a low concentration of the biocidal biocide ivermectin and into which water contaminated with biofouling larvae flows and which overlies a lower second layer of filter media coated with an inner biocidal polymer layer containing a high concentration of the biocidal biocide, ivermectin, and a low concentration of the biostatic biocide, capsaicin, and out of which water flows filtered free of biofouling larval forms.
FIG. 18C depicts a side view of the two layer filter depicted in FIG. 18B but with the first layer of filter media being coated with an outer biostatic polymer coating which is also impregnated with an additional biocide, a herbicide comprising a pyrithione metal salt that serves as an algaecide, fungicide, and bactericide.

FIG. 18B shows a variation of an anti-fouling filter that has a two-component or two-stage filter, where the upper-stage half-section of the filter 208 (3), with biostatic filter matrix substrate 201A that has water with veliger or cyprid larval forms flowing into it that is biostatic in nature because its filter media matrix substrate 201A is coated with a Polymer-O biostatic polymer layer 3 that has a high relative concentration of biostatic biocide, capsaicin (CA) 203, and a low relative concentration of a biocidal biocide, ivermectin (IV) 202. Thus in effect the upper-stage filter half 208 (3) with filter matrix substrate 201A functions as the Polymer-O layer 3, and for that reason it is double labelled.

Likewise, the lower-stage half-section of the filter 209 (9) with filter matrix substrate 201B that has water without veliger or cyprid larval forms that were either repelled from the filter because of attachment inhibition in the upper biostatic half section of the filter, or killed and filtered out by the lower biocidal half section of the filter. The lower-half portion of the filter 209 (9) is coated with a Polymer-I biocidal polymer layer 9 that has a high relative concentration of biocidal biocide, ivermectin (IV) 202, and a low relative concentration of biostatic biocide, capsaicin (CA) 203. Thus in effect the lower-stage filter half 209 (9), with filter matrix substrate 201B, functions as the Polymer-I layer 9, and for that reason it is double-labelled.

208A is the perforated upper boundary of upper half filter section 208 (3), into which water with larval biofouling forms flow in the direction of arrow 206, 209A is the perforated lower boundary of lower half filter section 209 (9) out of which water without larval biofoulings form flow in the direction of arrow 207, and 207A is the perforated boundary between upper filter section 208 (3) and lower filter section 209 (9).

This biofouling protected filter filters out larval forms by inhibiting attachment or killing them to prevent biofouling biomasses from forming on pipes downstream from the filter. It prevents larval forms from spreading downstream to contaminate other bodies of water, especially important for *quagga* and zebra mussel infestations of lakes and rivers. The larval forms are either killed outright in the lower half of the filter or gradually die in the upper half of the filter, and in any event the larvae never mature into adults, preserving the filtering ability and greatly extending the filter's operating life. The filter is easily replaceable, so that if the filter is eventually clogged with dead larval and juvenile invertebrate biofouling organisms, it can be simply replaced with an easy maintenance procedure instead of a laborious and expense periodic scraping of mussels or barnacles off the downstream pipes of power, water, and desalinization plants on a large scale, and plumbing systems of boats and ships on a small scale.

FIG. 18C is the exact same biofouling filter with the addition of an anti-algaecide function to the upper half filter section 208 (3), for example with a metal salt mixture of pyrithione (PY) 205. Capsaicin (CA) 203 and ivermectin (IV) are present as previously. The filter is capable of filtering out one-cell, primitive algal organisms before they can also proliferate. Although such organisms do not directly cause corrosive action on the downstream pipes, they encourage barnacles and mussels to settle by decreasing water flow velocity. Furthermore, large masses of algae can certainly obstruct pipes downstream from the filter. It is highly advisable to use a large pore pre-filter upstream from the main filter, as will be shown in FIG. 20A, to intercept large mechanical objects, particulates, and algae plants to prevent the main filter from getting quickly clogged from such objects. The pre-filter is also easily replaced as needed, and it too should be coated with the biofouling coating of this invention as should any piping leading to the filter.

In recent years, zinc pyrithione, the ingredient in numerous human anti-dandruff shampoos, has been used as an anti-algaecide component in bottom anti-fouling paints for boats. It is highly water insoluble (12 mg/L). The pyrithione moiety is not toxic to animal life, especially with the low water solubility and the inherent bio-specific lethality limited to plants, algae, fungi, and bacteria. The amount of zinc ion released, which is toxic to barnacles and mussels as well as to benign and beneficial life forms in the aquatic environment in the same manner that copper ions are, is very minimal. For that reason it cannot be used as a biocide for mussels and barnacles or other calcareous biofouling organisms. However, the zinc pyrithione does leach out gradually, putting a limitation on how long the anti-algae effect is maintained, and gradually biofilms, bioslime, and algae over the course of several years will eventually begin to accumulate. For that reason it should be present in the biofouling coating in fairly high concentrations by weight, between 1 and 10% with a preferential range of 4 to 7%. This requirement also applies for its inclusion into the outer Polymer-O coating of the current invention and applies to any appropriate pyrithione metal salt that may be used instead of zinc pyrithione.

The particles of the pyrithone salts should be as small as possible to increase the total surface area of these particles. Nanoparticle sized particles would be most beneficial. Many metal salts of pyrithione have been prepared, including the most common, zinc, but also silver, barium, strontium, titanium, copper (also used for algae control), calcium, and magnesium as well as others. The following process is provided to make the particles as small as possible.

The object is to prepare a mixture of pyrithione metal salts by precipitating them out of solution simultaneously. Of particular interest is the mixture of barium pyrithione (water solubility of about 77 mg per L) and zinc pyrithione (water solubility of about 12 mg per L) to which a small amount of silver pyrithione (water solubility of about 37 per L) is optionally added for additional biocidal (as an algaecide, fungicide, or bactericide) effect. Normally, when one metal pyrithione precipitates out, the precipitated particle size is decreased by decreasing the concentration of the metal soluble salt, agitating the solution with mechanical mixing, or decreasing the time the developing pyrithione salt crystal has in contact with the precipitating solution of sodium pyrithione. Solutions may be highly agitated with ultrasonic sound waves that produce high pressure cavitation bubbles that can break apart the developing crystals of precipitating solutions. Sharp transition changes from warm to cold will accomplish the same effect. But most importantly, a means has been developed to produce smaller metal pyrithione crystals by exploiting the presence of point substitutions of very large barium +2 ions for the very small zinc +2 ions in the zinc pyrithione crystal lattice.

When this occurs, an off-center ion defect has been produced which produces a repulsive ion charge asymmetry, repelling neighboring ions in the crystal lattice away. At the point where charge dislocations occur, a developing crystal is more likely to fracture and stop growing. Stress fractures are likely to occur where a low concentration of very large metal atoms with large atomic and ionic crystal radii is precipitated out into a crystal anion cation lattice at the same time that a more highly concentrated metal atom, with a much smaller atomic and ionic crystal radius, is precipitated out into the same crystalline lattice. The crystalline lattice fractures because of the charge distortions produced by the very large metal atom among the smaller surrounding metal atoms.

Barium has the second largest atomic and crystal ionic radius of any heavy or transitional metal (only cesium has a larger atomic radius) and zinc has the smallest atomic and crystal ionic radius of these two groups of metal ions. Hence these two salts are used together to produce virtually the largest possible off-center ion crystal lattice defect possible, thus allowing the crystal to more likely to fracture into smaller pieces by disruption of their crystallization planes as they crystallize during the precipitation process. Small quantities of silver pyrithione, with a similar effect to that of zinc because of the silver atom's similarly small size and atomic and crystal ionic radius, are optionally added because small quantities of silver ions will especially enhance the algaecide effect.

The specially prepared mixed barium zinc silver (silver is optional) is produced by the following process. One unit (e.g., 1 liter) of distilled water is prepared. Additional distilled water to dilute 0.05 units of pure 40% aqueous Na Pyrithione down to 0.4 units of 5% with solution three serial dilutions. A dilute 0.01 molar solution of 0.25 units of approximately 0.01 molar solution of AgF is prepared. The AgF solution is placed into a flask and place it into an ultrasonic cleaner with water. Alternatively, an ultrasonic sonicator probe is introduced into the AgF.

With the ultrasound turned on, the 5% Na Pyrithione is slowly added while the ultrasonic water cavitation process is being applied to the AgF solution. This is continued until no more precipitate of silver pyrithione forms. The ultrasonic sound is stopped and the supernatant fluid is filtered out. 50 g of BaCl2 powder and 250 g of ZnCl2 powder are added to make a solution that will not be supersaturated with respect to the BaCl2 to cause it to precipitate out. The silver pyrithione is added to the solution of BaCl2 and ZnCl2 and turn on the acoustical energy source. 0.1 units of 40% Na Pyrithione solution are prepared and place into a spray model with a nozzle. While stirring constantly if using the ultrasound cleaner, or while using the ultrasonic sonicator, keeping the spray nozzle close to the surface of the BaCl2/ZnCl2 solution, the 40% solution of Na Pyrithione is sprayed through a nozzle spray bottle with force onto the surface of the BaCl2 and continued until no further precipitate forms. The precipitate will contain Zn Pyrithione and Ba Pyrithione in a molar ratio of 5 to 1 and Ag Pyrithione will be in the precipitate in trace amounts. The supernatant fluid is poured off and filtered, the precipitate is allowed to dry, and then the precipitate is crushed with a motor and pestle. Any enhancement of this process by a commercial process would be considered to be within the scope of the current disclosure.

The filter application embodiment of the present invention can be extended further to filters employing activated carbon (AC) and graphene nano-platelets (GNP) as their filter matrix. Consistent with the definition of discrete molecular structures (monomers) arranged into repeating one- and two- and three-dimensional long chain molecules as the working definition of polymers, the three-dimensional, multi-layer graphite repeating hexagonal carbon structure (and its two dimensional single layer analogue, the graphene repeating hexagonal carbon structure) may be viewed as polymers as previously defined with respect to this invention.

These two substances may be considered to be special type of polymers where the repeating polymer unit is the 6 carbon hexagonal unit, hexene. In the case of activated carbon, that substance is equivalent to porous graphite in 3 dimensions, and in the case of the graphene nano-platelets, that substance is equivalent to pieces of single layer graphite or graphene. Both have a huge desirable surface area to volume ratio, desirable for an adsorptive type of filter for chemical substances, with the GNP capability exceeding that of AC, but both having the capability of not only filtering particulate matter very well and also the ability to adsorb chemical compounds extremely efficiently. This allows filters with efficient anti-fouling properties to be constructed.

Whereas in the usual surface polymer, a solid mixture or suspension of the biocide molecules is intercalated between the polymer molecular structures and are mechanically held there in a cage by the long molecules of polymers, with AC or GNP the biocide molecules are adsorbed into the innumerable crevices making up the huge surface area of AC or GNP and are held there by Van De Waal's intermolecular electrostatic forces rather than the mechanical forces of more conventional polymers molecular matrices. The effect regarding the biocide impregnated polymer coatings constituting the present invention is essentially the same in both cases.

In the same manner as with filters using discrete filter matrix structures can be structured with a two-layer arrangement, with the first, upper layer being biostatic and coated with polymers that have biocides impregnated into them, and whose second lower layer is biocidal and coated with polymers that have biocides impregnated into them, the same structural arrangement can be done with filters having AC or GNP or both. A quantity of AC may be mixed with a relatively larger quantity of biocidal biocide particles and a relatively smaller quantity of biostatic biocide particles and then introduced into a container to form a first biocidal layer. Then a quantity of AC may be mixed with a relatively larger quantity of biostatic biocide particles and a relatively smaller quantity of biocidal biocide particles and then that is introduced into a container to form a second biostatic layer on top of the first biocidal layer. Fluid flow is into the second or upper biostatic layer, out of that layer, and into the first or lower biocidal layer, and then out of the filter.

It is also possible to introduce additional layers in such a manner on top of the other two layers containing additional biocides, including algaecides. While these filters generally use AC, because they can be large and AC is inexpensive as compared to GNP, the latter can be used for small-dimensioned filters with the advantage that the latter has an even higher surface area than does AC. GNP can be added to the AC as a mixture or the AC can be used alone. Cyprids and veliger biofouling larval forms get trapped in the first biocidal layer of the filter, but because of the biostatic layer inhibiting attachment, they get either trapped and die, move in random directions and die, or the few that make it to the second biocidal layer of the filter, die. The water that comes out of the filter is decontaminated to the structures and bodies of water downstream.

Figure 19A:
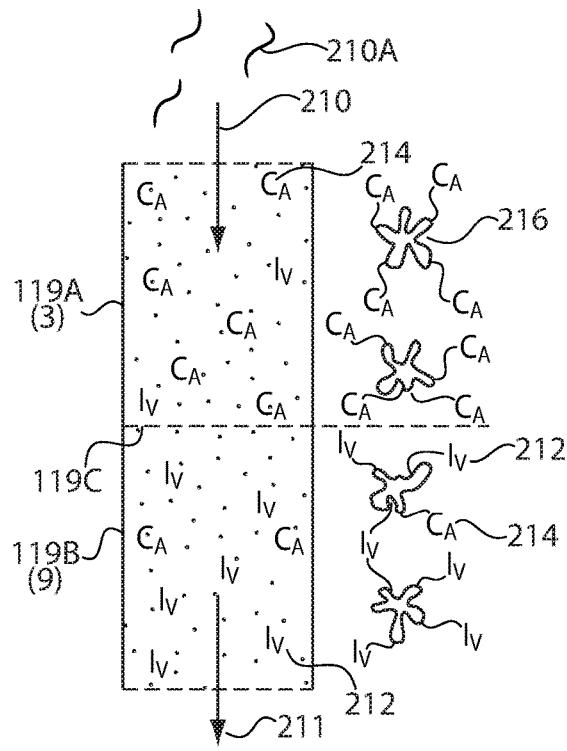
FIG. 19A depicts a side view of a filter with filter polymer media comprising either activated charcoal (AC), or graphene nano-platelets (GNP) or both, impregnated with biocides in such a manner so as to produce an upper outer biostatic polymer layer with a high concentration of the biostatic biocide, capsaicin, and a low concentration of the biocidal biocide, ivermectin, into which water contaminated with biofouling larvae flows, and a lower inner biostatic polymer layer with a high concentration of the biocidal biocide, ivermectin, and a low concentration of a biostatic biocide, capsaicin, and out of which water flows filtered free of biofouling larvae.

FIG. 19A shows water containing larval forms 210A in the form of veligers and cyprids flowing into the upper half 119A (3) of filter 119 that contains AC, GNP, or a mixture of the two. Also mixed in with the filter matrix is a high relative concentration of particles of capsaicin biocide (CA) 214 and a low relative concentration of particles of ivermectin biocide (IV) 212 that was mixed and impregnated into and adsorbed onto the filter matrix prior to it being placed into the filter.

The biocides are strongly adsorbed onto the AC filter matrix surface and it stays relatively permanently there. Thus the upper half of filter 119A (3) is essentially functioning as the outer biostatic Polymer-O 3 layer within the filter providing for the necessity of the double labelling. The microscopic larval forms 210A in the water, going into the filter as shown by arrow 210, are inhibited from attaching to the AC filter matrix because of the biocides, and they will either stay in that part of the filter adsorbed onto the filter and eventually die, or some will make it through boundary 119C and get swept into the lower half and biocidal part of the filter, where they will all die.

In the lower half of filter 119B (9), the filter matrix is again AC (or GNP, or a mixture of the two) that was previously was mixed and impregnated with and adsorbed onto a high relative concentration of particles of ivermectin (IV) 212 and a low relative concentration of particles of capsaicin (CA) 214 and these two biocides which are again strongly adsorbed to the filter matrix, where it remains essentially permanently, allowing the lower half of filter 119B to function as Polymer-I 9. The Polymer-I layer 9 is introduced first into the container housing the filter comprised by structures 119A(3) and 119B(9), followed by Polymer-O 3 being introduced into that container above the Polymer-I layer 9.

Particles of capsaicin and ivermectin are shown schematically being attached by the process of adsorption to particles of AC 216 along the side of the diagram depicting the filter. Water flowing out of the lower half of the filter 119B has been cleansed of larval forms and the water is sterile with respect to calcium forming invertebrate biofouling species. This antifouling filter performs at least two functions. Barnacle and mussel growth is prevented in vital structures downstream from the filter such as water intake pipes and vents for power plants, water plants, and desalinization plants that would cause severe maintenance issues with such structures and the spread of biofouling contamination downstream is prevented. These filters, conveniently located, can be replaced simply and much more easily than scraping shelled biofouling organisms off these structures. A large-bore mechanical pre-filter, preferably coated with an antifouling coating comprising the present invention, should be placed upstream to filter out larger mechanical objects that could prematurely clog up the main filter. Filters such as this, placed on the plumbing and bilge chambers of boats and ships, will help prevent spread of mussels, especially by the leisure boating industry.

Figure 19B:
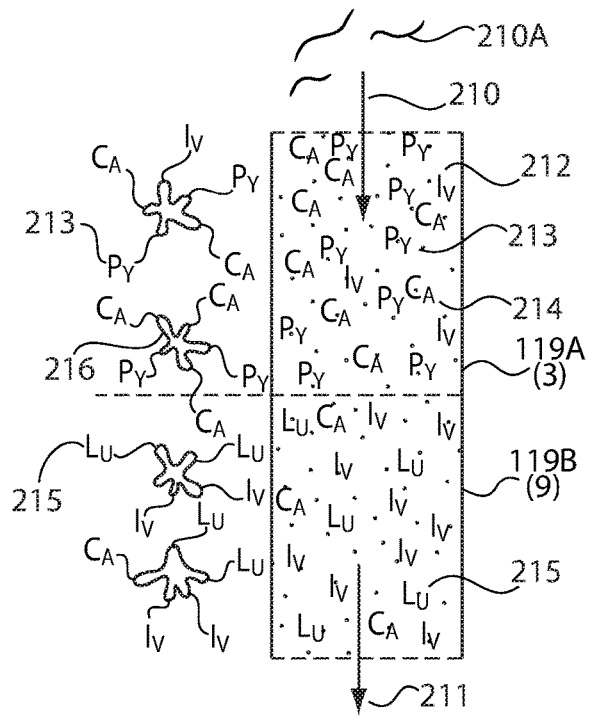
FIG. 19B depicts a side view of a filter with the same two polymer layer structure comprising AC, GNP, or both and containing the biocides capsaicin and ivermectin, but in addition, a second biocidal biocide, lufenuron, in high concentration in the second lower inner biocidal polymer layer, and in addition, the algaecide, a metallic salt of pyrithione, is also added to and impregnating the upper outer biostatic polymer layer.

FIG. 19B represents exactly the same AC filter (or GNP or a mixture of the two) application embodiment of the present invention as FIG. 19A except that a second biocidal biocide, lufenuron (LU) 215, was added to the ivermectin (IV) 212 and the capsaicin (CA) 214 to enhance the biocidal killing feature of the lower half of the filter 119 (9) and a second biostatic biocide, a pyrethrin type of compound 213 at a biostatic low concentration level, was added to enhance the biostatic biocidal effect of the upper half of the filter 119B (3). AC particles 216 are again shown with the biocides absorbed to their surfaces.

Figure 19C:
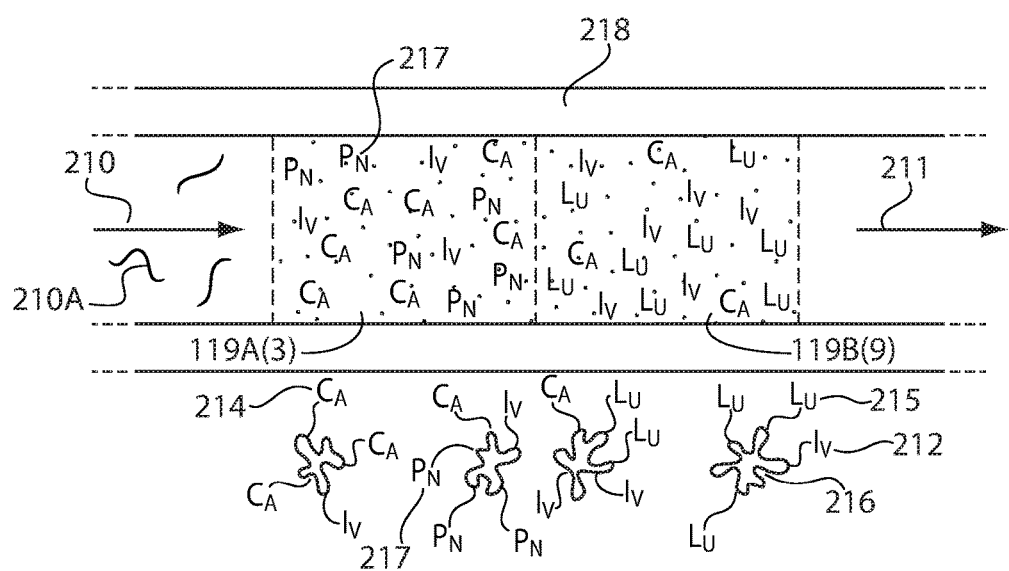
FIG. 19C depicts a cut-away view of a two polymer layer structured filter in a pipe comprised of AC, GNP, or both and in which the upper outer biostatic polymer layer into which water contaminated with biofouling larvae flows and which is impregnated with a high concentration of the biostatic biocide, capsaicin, a low concentration of the biocidal biocide, ivermectin, and a low biostatic concentration of the biocide pyrethrin and a lower inner biocidal polymer layer out of which water filtered free of biofouling larvae flows and which is impregnated with a high concentration of the biocidal biocide, ivermectin, a high concentration of the biocidal biocide, lufenuron, and a low concentration of the biostatic biocide capsaicin.

FIG. 19C depicts the same type of filter as was shown in FIGS. 19A and 19B, but the filter is shown within a pipe 218 with water containing larval forms 210A flowing into the filter indicated by arrow 210, but none being found in the water flowing out 211. Instead of a second biostatic biocide, pyrethrin (PY) 213, an algaecide, zinc pyrithione (PN) 217 or the mixed metal pyrithione whose formulation was just described, was added.

FIG. 20A represents the structural embodiment of a real world apparatus including a wave energy converter (WEC) electrical generator powering a sea water electrolysis unit. Such an apparatus could never be functional for more than one year after deployment in the ocean without antifouling, because of barnacle fouling. Unlike a boat or a ship, this kind of apparatus cannot simply be scraped clean of barnacles without doing significant damage to the surface of the apparatus, and removing it from the ocean would be a far more formidable and lengthy task than dry-docking a boat for several days.

In depicting the generator 230 of FIG. 20A, which is structurally similar in part to the WEC depicted in FIG. 13C, the structures (labels will have an asterisk) that must be protected from barnacles to allow feasible operation of the apparatus are shown. These parts, also seen on FIG. 13C, include the linear electric generator itself 157A*, the buoy portion 148 of the WEC, the metal enclosure 152* of the generator, power takeoff and transmission cable 150* (to which the coating application embodiment of FIG. 17A is applicable), sliding bearing surface 158*, and spring 154* (to which the coating application embodiment of FIG. 16A is applicable). WEC ballast counter mass 157C* and heave plates 157D* were not seen on FIG. 13C. All of these parts must be coated with the anti-fouling coating of the present invention.

Now moving onto the seawater electrolysis unit 242, the structures that are required to be coated with the anti-fouling coating of the present invention are outlined in dotted lines and the antifouling coating is labeled 238 wherever it is applied on the electrolysis unit. These structures include: seawater intake filter and inlet 239, water inlet pipe 231 coated on the outside and the inside with the antifouling coating 238 in the manner of the application embodiment of FIG. 14A (3), the underneath surface of the electrolysis buoy floatation collar 237, the electrolysis cell metal chamber 243, and exit pipe 238A (in the manner of application embodiment of FIG. 14A (2)) which only needs the antifouling coating on the outside because its interior carries seawater from which cyprid barnacle larvae forms were eliminated by anti-fouling filter 240 including a Polymer-O biostatic first half of the filter 3, through which water enters with cyprid larvae and in which these larvae are either inhibited from attaching, trapped within this portion of the filter, or they make it through along with the water to the Polymer-I biocidal second half of the filter 9 where they are killed as in the application embodiment of this coating seen in FIG. 18B and other figures and the water output from the filter 240, now free of any cyprids, now is able to enter the electrolysis cell through pipe or tubing 238A coated on the outside by antifouling coating 238 without the problem of cyprids entering the electrolysis chamber and biofouling it to a non-functional state.

A large pore pre-filter 232 is designed to filter out large particular matter and floating algae plants with a collection chamber 233 in front of it. Water exits filter 240 and larvae-free water is pumped by water pump 233A into ingress hole 235 and out egress hole 244 of water pump 233A. The possibility of barnacles rendering the water pump non-functional has been eliminated. Other structures on the electrolysis buoy 242 include a removable lid 236A held on to water flow path cover 236 by two latches 245 and a cleaning hole 232A adjacent to pre-filter 232 that allows removal of debris before it gets to the anti-fouling filter. Removal of removable lid 236A allows maintenance servicing access to the entire filtering chamber.

Sea water, which includes algae and barnacle cyprid larvae, is pumped in by water pump 233A through ingress hole 239, proceeds through intake pipe 231, and flows into filter chamber 233 through ingress hole 246. Heavy debris, including algae plants and so forth, are filtered by pre-filter 232 and debris piles up behind it, which can be periodically be cleaned out via hole 232A. All of these structures are coated with an anti-fouling coating 238.

Debris free water, but still contaminated by one-cell algae organisms and barnacle cyprids, flows next into another chamber where antifouling filter 240 is present. Water first flows into the first half of filter 240, labeled as 3 consistent with the biostatic biocide action of a Polymer-O layer as previously described. Here the water is also subject to algaecide treatment with an algaecide present in the Polymer-O 3 first half of the filter. At this point the cyprids are inhibited from attaching, so they either float aimlessly or get trapped in the first half of the filter and eventually die since they cannot attach. Those that make it out through the boundary between the first half biostatic part of the filter and into the biocidal second half of the filter 9 consistent with the Polymer-I layer die on contact with the biocidal biocides there. The filter 240 may include any filter of the types shown in FIG. 18A-C and FIG. 19A-C.

By the time the water leaves the anti-fouling filter, the water is rid of all biofouling organisms and the biofouling free water enters pump 233A through inlet 235. Water is subsequently pumped out by pump 233A through outlet 244. This arrangement allows the pump to pump water free of any organisms that can biofoul the pump, thereby maximizing the pump's life. Power for the pump comes from WEC 230 via cable 244. The water gets pumped into return plastic pipe or tube 238A, covered with an antifouling coating on the outside, and brings biofouling organism-free water into the electrolysis unit 243, where the water is split into hydrogen and chlorine (or oxygen in one type of sea water electrolysis unit) by cathode 240 and anodes 241, powered by electricity from the WEC sent to the electrolysis unit by cables 244.

Note that the anti-fouling filter and the pre-filter can easily be changed out for new filters and the water filter chamber can be easily vacuumed and cleaned of debris. Thus, this apparatus, in order to work properly over extended periods of time in the ocean, uses various embodiments of the anti-fouling coating comprising this invention throughout this apparatus, both for the WEC portion and the electrolysis unit portion.

Figure 20B:
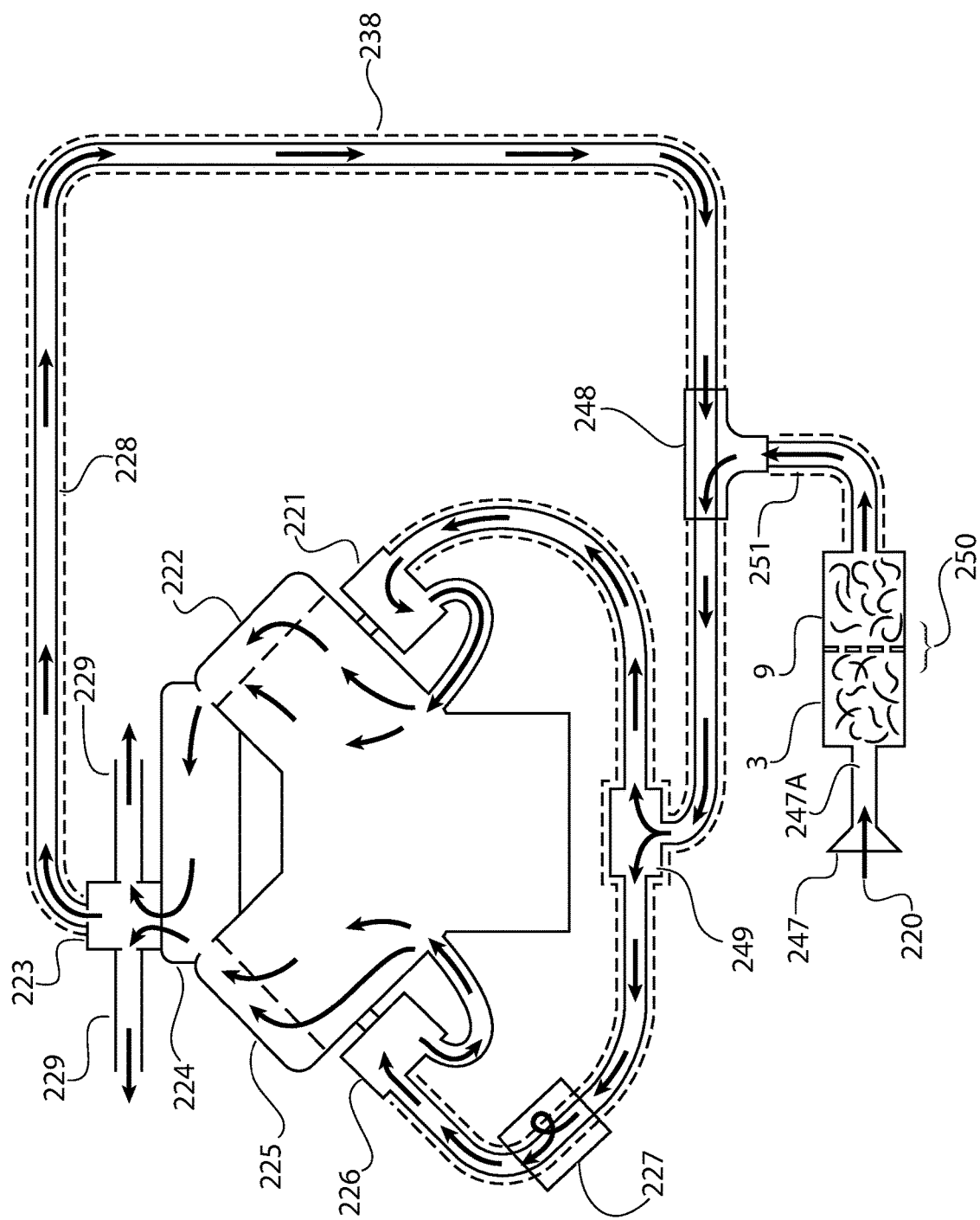
FIG. 20B depicts a schematic diagram of a raw water engine cooling system protected from internal biofouling by a water intake filter having a first outer biostatic layer of filter media coated with a polymer impregnated with a biostatic biocide and a second inner biocidal layer of filter media coated with a polymer impregnated with a biocidal biocide.

FIG. 20B shows a raw water engine-cooling system for boats and ships. One of the most common causes of premature engine failure is biofouling and clogging of the internal water path of such a cooling system. Such failures can be prevented by the features of this invention, and following the water path will reveal the resulting benefits.

Water flows in through a sea strainer 247 coated with the anti-fouling coating 238 comprising the present invention, through antifouling filter 250 and first biostatic filter section 3 then through second biocidal filter section 9, and then is pumped into intake valve 248 via water inlet pipe 251. Next the water, now veliger- and cyprid-free, is pumped into the engine cooling system by water pump 249. From there it is pumped to the oil cooler 227, then to the exhaust manifolds 221 and 226, then to the cylinder heads 222 and 225, then to the intake manifold 224.

Part of the water goes to the overboard hot engine water exhaust pipes 229 and back into the lake, river, or ocean. The rest of the water leaves the engine area through outtake valve 223 where the thermostat housing (not shown) is located and through the cold engine water bypass pipe 228 to recirculate back to the water intake valve 248 to start the cycle again. Whatever portion of pipe is exposed to the external environment and water is coated on the outside with the anti-fouling coating 238. No biofouling occurs internally in the engine because of the removal of the larval cyprid or veliger organisms by intake antifouling filter 250.

As a second safety precaution, the piping internal to the boat comprising the engine cooling system can also be coated by the anti-fouling coating on the interior of the piping in case any larval forms made it past filter 250. Such antifouling coating is indicated by dotted lines and it would lie on the inside surface of the piping internal to the engine (though on diagram for spatial reasons it is shown solely on the outside of the piping). It is not necessary to do this for the part of the circulatory path where the water temperature is very hot, such as the overboard engine exhaust water tubes 229 or the manifolds 221 and 226, and cylinder heads 222 and 225 or the intake manifold 224, as the temperatures are far too high to allow barnacles and mussels to grow here.

The net result of this is four-fold: 1) there is no biofouling in and around the engine; 2) engine life is improved; 3) water contaminated with biofouling organisms goes into the boat engine plumbing and comes out cleansed of contamination; and 4) the oil heat cooler (heat exchanger), the most frequent target for barnacles and mussels leading to the most frequent cause of heat exchanger failure and subsequent engine failure, is now protected from bio-corrosion that causes mechanical heat exchanger failure and biofouling which prevents proper water flow and heat exchange causing engine overheating failure.

Valuable and essential sources of biocides of beneficial use for this invention are the plant alkaloids. Although the main emphasis in the disclosure has been on capsaicin as a preferred member of this class, the use of capsaicin is to be considered representative of a wide range of natural plant alkaloids that show anti-arthropod properties. Capsaicin, a preferred plant alkaloid and biocide for the purposes of this invention discussed already in great detail, has long been used in Chinese herbal medicine, has been approved by the Environmental Protection Agency as an insecticide, and is one of the very few pesticides that have no known toxicity to beneficial aquatic lifeforms. Pyrethrum, the alkaloid extract of the *chrysanthemum*, an extract long used in Chinese herbal medicine, was also described in detail with respect to its chemically synthesized related compounds, the pyrethrins and pyrethroids and their use as biocides in this invention. Many of these compounds have not been studied to the extent that every physical property such as the diffusion constant, D, or the release rate constant, Kh, (using Higuchi Model notation) or the adsorption coefficient, KOC, are known. However, in general, virtually all of them are water insoluble, or nearly so, are characterized by large molecular volumes and weights, would be impregnated in an extremely stable manner into polymers of low porosity (e, using the Higuchi Model notation), and thus would be expected to have a very low D, a very high KOC, and thus an extremely low Kh, and thus a very miniscule chemical leaching rate out of the polymer matrix into the surrounding aqueous environment, and thus duplicate the physical behavior of capsaicin. Furthermore, the mode of action of these compounds is generally to either hyperpolarize or depolarize in an irreversible manner the cellular membranes of the central nervous system of the targeted organism, thereby paralyzing it and killing it.

The use of large molecule biocides also has two other very important advantages. First, the porosity of the outer biostatic polymer-O layer, e in the Higuchi Model, can be reduced by the intercalation of large molecules into the pores between long polymer molecules, further reducing the e porosity factor even more thereby helping to reduce further the chemical leaching rate. Second, it has been well described that biofouling due to barnacles, mussels, and other biofoulants is increased when the microstructure of the protected surface shows increase roughness, ridging, crevices, and pores (such a micro-relief structure decreases washing away, effects of predators, and overall mortality of the settled organisms). Thus, by filling in the pores of the polymer, the large molecules of the biocide make it more difficult for the organisms to attach helping the outer biostatic repelling Polymer-O layer repel the organisms and prevent attachment.

Another example of the group of natural plant alkaloid anti-arthropod Chinese herbal insecticides that would be beneficially useful for the purposes of the present embodiments is the extract of the thunder god vine. In particular, it is noted that the extract of *Triptergium wilfordii* (thunder god vine) contains multiple plant alkaloids with anti-arthropod properties. At least three of them are insecticides that have been investigated for their biocidal properties—celastrol (tripterine), triptolide, and wilforine. Celastrol is a large molecule, $C_{29}H_{38}O_4$ with a large molecular weight of 450.61 g/mol and a water solubility of less than about 1 mg/L. Triptolide, another large molecule, $C_{20}H_{24}O_6$, with a large molecular weight of 360.41 g/mol and a water solubility of only 0.017 mg/L. Wilforine is a very large molecule, one of the largest natural non-protein, non-nucleic acid proteins found in nature, $C_{43}H_{49}NO_{18}$, with an molecular weight of 867.9 and a water solubility that is unmeasurably low, much less than about 1 mg/L. Wilforine's mechanism of action is to inhibit irreversibly the cellular $Na^+$- $K^+$-ATPase membrane transport system, thus irreversibly depolarizing the cell membrane and paralyzing the nervous system of the arthropod.

All 3 drugs are safe enough to have been used in human medicine, will target arthropods, do not have any chlorinated moieties in their molecules, and are available at low cost in large commercial quantities. Thus, this molecular anti-arthropod natural plant three-component biocide alkaloid is excellent for use for the purposes of the present embodiments. As noted below, these compounds would be expected to also possess anti-fouling activity against invasive mussels as well.

The list of plant alkaloids and Chinese herbal extracts showing anti-arthropod activity that is useful for and part of this invention is a subset of all known members of this class of compounds. There are many plant alkaloid extracts with that do not meet the specific criteria and requirements of this invention and therefore are not useful for the present embodiments.

It is further to be noted that the scope of biocides applicable to this invention may be further enlarged using known taxonomic and physiological relationships that extend between different taxonomic animal groups. It is to be noted that barnacles are crustaceans, and crustaceans are arthropods. Insects, mites (and sea lice), parasitic worms, arachnids, and multi-legged worm like creatures (centipedes, millipedes etc.) are all arthropods, and biocides developed against any one class of arthropods have been shown or can be shown to be active against any other class of arthropods, with allowance for different degrees of efficacy. Many experimental studies confirm this cross-therapeutic phenomenon. Thus, any member of the class of insecticides listed in the table of FIG. 21A, mitocides listed in the table of FIG. 21B, plant alkaloids possessing insecticide properties listed in the table of FIG. 21D, whose molecules possess the required molecular structure, physical properties, and chemical properties delineated in detail within this disclosure would fall under the scope of this invention when they are used as biocides against barnacles in the compositions so specified in this invention. This suitability as a biocide against barnacles would also extend to any member of the class of Chinese natural herbal insecticides possessing the necessary physical and chemical properties stated above. Furthermore, invasive shrimp and crab species, especially of the type noted to biofoul oil platforms, because they too are crustaceans, would be successful targets of any arthropod biocides that are effective against barnacles.

Furthermore, it is seen that because the taxonomic relationship between barnacles and invasive mussels and shipworms is so close, though the former organism is a member of the animal phylum Arthropoda, and the latter two types of organisms are members of the slightly more primitive phylum Mollusca, organisms of the two phyla possess so many physiological, chemical, structural, and cellular and especially neuronal cellular membrane processes in common that a biocide effective against barnacles will be effective against invasive mussels and shipworms, and a biocide effective against invasive mussels and shipworms will be effective against barnacles. This phenomenon has been shown to be operative in almost all instances by the present and past use of available biocides against barnacles and invasive mussels. This phenomenon is also the basis of the statement that members of the desired class of Chinese herbal insecticides possessing the desired properties described as being beneficial to this invention, and that are active against insects, and therefore, would be active against barnacles, also would be active against invasive mussels. However, this invention is the first process that fully employs this phenomenon based on known taxonomic biological principles and processes listed above to greatly enlarge the use of available biocides for anti-fouling purposes using the process, structure, and compositions of the anti-fouling coating defined and described in the present invention.

The use of biostatic herbicides with fungicide and bactericide properties, such as the pyrithione metal salts, are of further significance in terms of enhancement to the functioning of the anti-invertebrate biofouling of this invention. It is well known that the formation of a biofilm microfouling including bacteria, fungi, and one cell algae such as diatoms enhances the colonization of surfaces by the macrofouling organisms that are the principle focus of this invention. If one has a mass settlement of cyprid or veliger larvae on a surface toxic to them, the result will be a layer of dead juvenile barnacles or mussels which have just completed metamorphosis upon attachment with their small shells, forming a neutral interlayer of increase micro-relief structure and roughness as well as shielding later arriving larvae forms from being exposed to contact with the toxic surface, both of which creates favorable conditions for development of other barnacles and mussels upon the dead layer. The addition of an herbicide to the outer biostatic Polymer-O layer greatly helps to mitigate against that undesirable process, first by making the surface less hospital from the biofilm to the arriving larval forms, and then having a fewer number of them having the need to be repelled from the surface by the biostatic outer polymer layer.

Note that zinc oxide is also algaecidal but is not preferred for use as the zinc oxide is converted to zinc oxychloride, which is the same mechanism as its anti-barnacle and mussel effect, and it is toxic to the aquatic environment much in the same way as copper based coatings are. On the other hand, zinc pyrithione exerts its phytotoxic and algaecidal effect through the pyrithione moiety rather than the zinc moiety, with no environmental harm, a process that is safe enough for humans to use as a dandruff shampoo. Furthermore, zinc pyrithione is beneficially less soluble in water, about 12 mg/L as opposed to zinc oxide, about 16 mg/L (pure water, but considerably more in sea water because of conversion of zinc oxide to zinc oxychloride by the chloride ions in the water).

Embodiments of the present invention have tested for their effectiveness. Panels of fiberglass were placed in the water in the temperate climate of New York and were coated with various biostatic and biostatic biocides in the manner of the present embodiments. The outer biostatic layer of the coating of some treated panels was also impregnated with the algaecide, zinc pyrithione (ZPT). Each biostatic and biocidal biocide tested had a panel with and without the algaecide. The panels with the ZPT were more effective at inhibiting surviving barnacles than the panels just with the biostatic and biocidal biocides alone, owing to the fact that an algae coating would partially shield the barnacle larvae from the outer biostatic biocide polymer layer, allowing more of them to get a foothold.

Sea Grapes (Moluga manhattansis) and Golden Heart (Botryllus schlosseri) were found during the test. These organisms displayed such voracious growth, many times more rapid then the barnacle populations, that on the panels without the algaecide, the Sea Grapes within two weeks coated the panels with a biomass weighing at least 25 kg and 3 inches thick on a 12 inch by 24 inch fiberglass panel, almost causing the panel to crack and splinter apart as well as potentially rupturing the suspending cables. The Golden Hearts grew somewhat less rapidly, but nevertheless formed thick circular colonies on the panels intermingled with the Sea Grapes. The barnacles that initially survived because of the algae layer on the non-algaecide panels, were smothered and killed by these two more aggressive organisms. However, on the panels that were treated with the ZPT algaecide and the biostatic/biocidal biocides, there were no barnacles, no Sea Grapes, and insignificant amounts of Golden Heart and algae.

Tests thus showed not only a synergistic effect from the ZPT and the biostatic/biocidal biocides against barnacle growth and formation due to algae growth inhibition, but also showed a total eradication of the two tunicates. The magnitude of this effect during testing was unanticipated given that, for both of these biofouling invading organisms, there were no known practical treatment strategies that were both effective and safe for the aquatic environment.

One mechanism for this effectiveness appears to be potentiation of the biostatic and biocidal biocides by the ZPT. A second mechanism may be that the presence of the animal biofouling biocides that are used within the scope of this invention also extends the biocidal activity of the ZPT so that it includes lower-order invertebrate animal organisms. Both mechanisms may be operative.

It is hypothesized that the highly efficient tunicate sexual reproductive mode of ova and sperm that result in egg and subsequent larvae formation, settling, and attachment is interfered with by the combination of the multiple biofouling invertebrate biocides employed in the embodiments of this invention and the algaecide. The other, less efficient, asexual methods of tunicate reproduction, including budding and colony fragmentation, are incapable of compensating for this inhibition of sexual tunicate reproduction. It has been noted that the presence of zinc in a surface coating can inhibit the maturation of eggs, and reproduction by egg formation is much more critical to the tunicate proliferation, short range settling, and distribution then it is to barnacles and invasive mussels that primarily rely on cypriad and veliger larvae, respectively. Note that zinc is a component of the ZPT molecule. Thus, the embodiments of this invention that employ the use of an algaecide that is a member of the group of zinc and other heavy metal pyrithione salts are not only more effective against barnacles, invasive mussels, and other calcareous biofoulers, but also they represent the first completely effective, practical, and environmentally safe treatment of the virulent non-calcareous tunicate biofoulers.

Those skilled in the art would be able to determine other such embodiments that would all still fall under the art represented by the current invention. Likewise, the theoretical number of application embodiments encompassing various yet to be determined applications of this invention in the field of biofouling prevention, when they would in the future become apparent to those skilled in the art that encompasses this invention, would be expected to be large, but this broad universe of applications would be embodiments that would fall within the scope of the current invention.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. Additional information is provided in Appendix A to the application. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention.

The invention claimed is:

1. A multi-layer anti-fouling coating comprising:
    a first biocidal layer formed on a surface, the first biocidal layer comprising at least one biocidal biocide that kills biofouling organisms on contact with the first biocidal layer; and
    a first biostatic layer formed between the first biocidal layer and an external environment, the first biostatic layer comprising at least one biostatic biocide that inhibits biofouling organisms from attaching to the first biostatic layer and does not kill biofouling organisms on contact with the first biostatic layer, wherein the first biocidal layer further comprises the at least one biostatic biocide and the first biostatic layer further comprises the at least one biocidal biocide, wherein the concentration of the at least one biocidal biocide in the first biocidal layer is higher than the concentration of the at least one biocidal biocide in the first biostatic layer, and wherein the concentration of the at least one biostatic biocide in the first biostatic layer is higher than the concentration of the at least one biostatic biocide in the first biocidal layer.

2. The multi-layer anti-fouling coating of claim 1, further comprising a first primer layer between the first biocidal layer and the surface.

3. The multi-layer anti-fouling coating of claim 2, wherein the first primer layer comprises a biocidal biocide that kills biofouling organisms on contact with the first primer layer.

4. The multi-layer anti-fouling coating of claim 2, wherein the first primer layer comprises an epoxy primer comprising aluminum.

5. The multi-layer anti-fouling coating of claim 2, wherein the first primer layer comprises an epoxy primer comprising zinc.

6. The multi-layer anti-fouling coating of claim 1, further comprising a second primer layer between the first biocidal layer and the first biostatic layer.

7. The multi-layer anti-fouling coating of claim 6, wherein the second primer layer comprises a biocide selected from the group consisting of a biocidal biocide and a biostatic biocide, wherein the biocidal biocide kills biofouling organisms on contact with the second primer layer, and wherein the biostatic biocide inhibits biofouling organisms from attaching to the second primer layer and does not kill biofouling organisms on contact with the second primer layer.

8. The multi-layer anti-fouling coating of claim 6, wherein the second primer layer comprises an epoxy primer comprising aluminum.

9. The multi-layer anti-fouling coating of claim 6, wherein the second primer layer comprises an epoxy primer comprising zinc.

10. The multi-layer anti-fouling coating of claim 1, wherein the at least one biostatic biocide in the first biocidal layer is present in a concentration below a concentration of the at least one biocidal biocide in the first biocidal layer and wherein the at least one biocidal biocide in the first biostatic layer is present in a concentration below a concentration of the at least one biostatic biocide in the first biostatic layer.

11. The multi-layer anti-fouling coating of claim 1, wherein the first biocidal layer further comprises a first polymer matrix, wherein the first biostatic layer further comprises a second polymer matrix, and wherein the first and second polymer matrices are each selected from the group consisting of polyvinyl chlorides, polyurethanes, polystyrenes, celluloses, polyethylenes, acrylics, nylons, polysulphones, liquid crystals, fluoropolymers, epoxies, and resins.

12. The multi-layer anti-fouling coating of claim 1, wherein the first biostatic layer and the first biocidal layer together form a fused multi-coating polymer layer.

13. The multi-layer anti-fouling coating of claim 1, wherein the first biostatic layer further comprises an additive selected from the group consisting of carbon fiber, aramide fiber, silicon dioxide, fluorspar, stainless steel, boron carbide, cubic boron nitride, silicon carbide, carborundum, metal carbides, sand, and industrial diamond.

14. The multi-layer anti-fouling coating of claim 1, wherein the first biostatic layer further comprises an additive selected from the group consisting of silicone powder, molybdenum disulfide powder, PTFE powder, graphite powder or flakes, non-cubic boron nitride, graphene nanoplatelets, graphene oxide, and fluorinated graphene powder.

15. The multi-layer anti-fouling coating of claim 1, wherein the first biostatic layer further comprises an algaecide.

16. The multi-layer anti-fouling coating of claim 15, wherein the algaecide includes zinc pyrithione.

\* \* \* \* \*